United States Patent
Shen et al.

(10) Patent No.: US 10,787,422 B2
(45) Date of Patent: *Sep. 29, 2020

(54) PYRIMIDONE COMPOUNDS USED AS LP-PLA₂ INHIBITORS AND PHARMACEUTICAL COMPOSITIONS THEREOF

(71) Applicant: Shanghai Institute of Materia Medica, Chinese Academy of Sciences, Shanghai (CN)

(72) Inventors: Jianhua Shen, Shanghai (CN); Yiping Wang, Shanghai (CN); Xinde Chen, Shanghai (CN); Wenwei Xu, Shanghai (CN); Kai Wang, Shanghai (CN)

(73) Assignee: Shanghai Institute of Materia Medica, Chinese Academy of Sciences, Shanghai (CN)

(*) Notice: Subject to any disclaimer, the term of this patent is extended or adjusted under 35 U.S.C. 154(b) by 0 days.

This patent is subject to a terminal disclaimer.

(21) Appl. No.: 16/299,636

(22) Filed: Mar. 12, 2019

(65) Prior Publication Data

US 2019/0248751 A1  Aug. 15, 2019

Related U.S. Application Data

(63) Continuation of application No. 15/540,025, filed as application No. PCT/CN2015/099252 on Dec. 28, 2015, now Pat. No. 10,280,146.

(30) Foreign Application Priority Data

Dec. 26, 2014 (CN) .......................... 2014 1 0855183

(51) Int. Cl.
| | |
|---|---|
| A61K 31/513 | (2006.01) |
| C07D 239/54 | (2006.01) |
| A61K 31/541 | (2006.01) |
| C07D 401/04 | (2006.01) |
| C07D 403/04 | (2006.01) |
| C07D 239/48 | (2006.01) |
| C07D 409/04 | (2006.01) |
| C07D 239/52 | (2006.01) |
| C07D 239/545 | (2006.01) |
| C07D 239/56 | (2006.01) |
| C07D 401/12 | (2006.01) |
| C07D 403/06 | (2006.01) |
| C07D 413/04 | (2006.01) |

(52) U.S. Cl.
CPC .......... *C07D 239/54* (2013.01); *A61K 31/513* (2013.01); *A61K 31/541* (2013.01); *C07D 239/48* (2013.01); *C07D 239/52* (2013.01); *C07D 239/545* (2013.01); *C07D 239/56* (2013.01); *C07D 401/04* (2013.01); *C07D 401/12* (2013.01); *C07D 403/04* (2013.01); *C07D 403/06* (2013.01); *C07D 409/04* (2013.01); *C07D 413/04* (2013.01)

(58) Field of Classification Search
CPC .. A61K 31/513; C07D 417/04; C07D 413/04; C07D 403/04
USPC .......................................... 514/317; 544/274
See application file for complete search history.

(56) References Cited

U.S. PATENT DOCUMENTS

| | | | |
|---|---|---|---|
| 4,608,383 A | 8/1986 | Wiedemann et al. | |
| 10,280,146 B2 * | 5/2019 | Shen ................... | A61K 31/513 |

FOREIGN PATENT DOCUMENTS

| | | |
|---|---|---|
| JP | 2005-350363 A | 12/2005 |
| JP | 2012-006869 A | 1/2012 |
| WO | WO 2003/042206 A1 | 5/2003 |
| WO | WO 2004/014868 A3 | 5/2003 |
| WO | WO 2004/014868 A2 | 2/2004 |

OTHER PUBLICATIONS

Japanese Office Action, dated Apr. 27, 2018, in counterpart Japanese Application No. 2017534564 and Partial English Machine Translation (9 pages).
European Patent Office Extended Search Report, dated Jun. 11, 2018, in counterpart European Application No. 15871995.5 (15 pages).
Zav'yalov et al., "Synthesis of Cytosine Derivatives from 1-Substituted Uracils," Russian Chemical Bulletin, 11, pp. 2530-2533 (1972) (1 page Abstract Only); Accession No. 1973:72056—XP-002781280.
Zhang et al., "Design and Synthesis of Pyrimidone and Pyrimidinedione Inhibitors of Dipeptidyl Peptidase IV," Journal of Medicinal Chemistry, 52(2), pp. 510-524 (2011) (1 page Abstract Only) Accession No. 2010:1613600—XP-002781282.

(Continued)

*Primary Examiner* — Jeffrey H Murray
(74) *Attorney, Agent, or Firm* — Calderone Bullock LLC

(57) ABSTRACT

The present invention relates to pyrimidone compounds used as Lp-PLA₂ inhibitors and pharmaceutical compositions thereof. The structure of the pyrimidone compounds is represented by general formula (I), wherein $R_1$, $R_2$, $R_3$, X, Ar, Y and n are defined as in the specification and claims. The compounds of general formula (I) in the present invention, stereoisomers and pharmaceutically acceptable salts thereof can be used as Lp-PLA₂ inhibitors for preventing, treating and/or ameliorating diseases associated with the activity of Lp-PLA₂ enzyme.

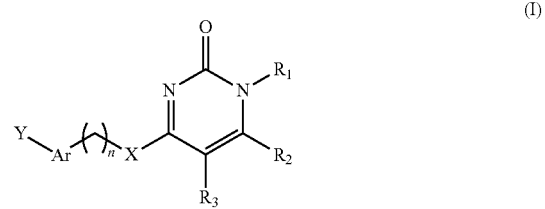

(I)

8 Claims, 7 Drawing Sheets

(56) References Cited

OTHER PUBLICATIONS

Wamhoff et al., Heterocyclic Beta-Enamino Esters. 13. Halogenation and Rearrangement of Furo[2,3-d]pyrimidines, Chemische Berichte, 107(7), pp. 2265-2273 (1974) (1 page Abstract Only) Accession No. 1974:491471—XP-002781283.
Reznik et al., "Synthesis and Properties of Pyrimidinylaklphosphonic Acids, 10. Chemical Transfromations of Isomeric Uracilphosphates," Russian Chemical Bulletin, 6, pp. 1401-1405 (1975) (1 page Abstract Only) Accession No. 1975:564298—XP-002781284.
Nagamatsu et al., "Isolation of New Chlorinated Regioisomers of Mono N-Substituted Uracil Derivatives and Synthesis of 3-Substituted 8-Phenylprimido[5,4-e]-1,2,4-triazine-5,7(6H,8H)-diones," Heterocycles, 37(2), pp. 1147-1164 (1994) (1 page Abstract Only) Accession No. 1994:409349—XP-002781285.

\* cited by examiner

PYRIMIDONE COMPOUNDS USED AS LP-PLA$_2$ INHIBITORS AND PHARMACEUTICAL COMPOSITIONS THEREOF

CROSS-REFERENCE TO RELATED APPLICATIONS SECTION

This patent application is a continuation of pending U.S. patent application Ser. No. 15/540,025, filed Jun. 26, 2017, entitled Pyrimidone Compounds Used As Lp-PLA2 inhibitors and Pharmaceutical Compositions," the entire disclosure of which is incorporated herein by reference.

BACKGROUND OF THE INVENTION

Field of the Invention

The present invention relates to the field of pharmaceutical chemistry, and more particularly to novel pyrimidone compounds and preparation method, pharmaceutical compositions containing such compounds as active ingredients, and use thereof in the manufacture of medicaments for the treatment of diseases associated with Lp-PLA$_2$ enzyme activity.

Description of Related Art

Lipoprotein-associated phospholipase A$_2$ (Lp-PLA$_2$), also known as platelet activating factor acetylhydrolase (PAF-AH), contains 441 amino acids with a relative molecular mass of 45 kD. 70% of Lp-PLA$_2$ in human plasma binds to low density lipoprotein (LDL) and 30% of Lp-PLA$_2$ binds to high density lipoprotein (HDL). Lp-PLA$_2$ can rapidly hydrolyze oxidized phosphatidylcholine into lysophophotidylcholine (lyso-PC) and oxidized non-esterified fatty acids (ox-NEFA), while both lyso-PC and ox-NEFA have a strong proinflammation effect and can initiate inflammation/immune response of a variety of cells including endothelial cells, smooth muscle cells, monocytes/macrophages, T cells and neutrophils.

Lp-PLA$_2$ inhibitors can be generally applicable to any condition involving the hydrolysis of oxidized lipids into the two inflammatory substances in the participation of Lp-PLA$_2$. This includes atherosclerosis, diabetes, diabetic eye diseases, hypertension, angina, rheumatoid arthritis, stroke, myocardial infarction, post ischemia-and-reperfusion conditions, psoriasis, brain inflammatory diseases (e.g., Alzheimer's disease), various neuropsychiatric disorders (e.g., schizophrenia), ischemia-reperfusion injury, sepsis, acute and chronic inflammatory diseases.

Atherosclerosis is not only related to abnormal levels of blood lipids, but also an inflammation-related disease. It is a new way to treat the disease by inhibiting inflammatory factors of atherosclerosis. Studies have shown that lyso-PC can promote the development of atherosclerotic plaques and eventually form necrotic cores. Experiments on the diabetic hypercholesterolemic pig model have demonstrated that Lp-PLA$_2$ inhibitors can affect the volume, composition and gene expression of atherosclerotic plaques in diabetic/hypercholesterolemic pig and can effectively inhibit the continued growth of atherosclerotic plaques.

Studies have shown that all neurodegenerative diseases, such as multiple sclerosis, Parkinson's disease, Alzheimer's disease and the like, demonstrate neuroinflammation. Lyso-PC, as a proinflammatory factor, can induce the release of a variety of cytotoxic inflammatory cytokines, while Lp-PLA$_2$ inhibitors can attenuate the inflammatory response by inhibiting the production of lyso-PC.

In addition, the brain of patients with Alzheimer's disease (AD) showed significant neuroinflammation, and a number of cytotoxic inflammatory cytokines were up-regulated. Experiments on the diabetic/hypercholesterolemic pig model showed that Lp-PLA$_2$ inhibitors are able to improve function of the blood brain barrier (BBB), reduce permeability of the blood-brain barrier (BBB), and reduce precipitation of the beta-like protein in the brain. These research results suggested that Lp-PLA$_2$ inhibitors may be useful in the treatment of Alzheimer's disease.

Because lyso-PC is involved in leukocyte activation, induces apoptosis and can mediate endothelial dysfunction, and diabetes can cause persistent vascular inflammation and increase the production of reactive oxygen, it is generally believed that Lp-PLA$_2$ inhibitors can be used in the treatment of diabetes-related tissue damage by inhibiting the production of lyso-PC. Considering that local inflammatory response plays an important role in the development and progression of diabetic retinopathy, it is speculated that Lp-PLA$_2$ inhibitors can be used in the treatment of diabetic eye disease.

In addition, the destruction of the blood retinal barrier (BRB) is a common pathological feature of diabetic macular edema (DME) patients. Under normal circumstances, BRB can prevent the free flow of plasma components into the retina through active and passive transport, thereby maintaining the self-stability of the receptor cells in the retina. Once BRB is destroyed, it cannot strictly control the water and protein in plasma from entering into the retinal parenchymal layer, leading to significant expansion of retinal extracellular space which exhibits as macular edema in the macular area. Animal experiments on streptozotocin (STZ)-induced SD rat and brown Norwegian rat models showed that Lp-PLA$_2$ inhibitors are able to reduce BRB permeability and the research results showed that Lp-PLA$_2$ inhibitors might be useful in the treatment of diabetic macular edema.

Both glaucoma and age-related macular degeneration (AMD) are retinal neurodegenerative diseases. Studies have shown that inflammatory response, including TNF-α signaling pathway, may play an important role in these two diseases. Considering that Lp-PLA$_2$ inhibitors can block the release of inflammatory cytokines, it is speculated that Lp-PLA$_2$ inhibitors can be used in the treatment of glaucoma and AMD.

GlaxoSmithKline has developed a class of potent reversible inhibitors of Lp-PLA$_2$ (WO 99/24420, WO 01/60805, WO 02/30911, WO 03/016287, WO 03/042179, WO 03/042206, WO 08/048867, and etc.), characterized by pyrimidone or pyridone groups contained in the structure. The representative compounds darapladib and rilapladib are currently in clinical research.

GlaxoSmithKline also developed another class of Lp-PLA$_2$ inhibitors (US 2012/0142717, WO 2012/075917, WO 2012/037782, WO 2013/013503, WO 2013/014185, WO 2014/114248, WO 2014/114249, WO 2014/114694). The structure thereof is also characterized by pyrimidone group, but this class of inhibitors differs from the previous class of reversible inhibitors in that they have a linear structure and their molecular weight is also relatively small.

There is still a need for further research and development of Lp-PLA$_2$ inhibitors in this field.

BRIEF SUMMARY OF THE INVENTION

The object of the present invention is to provide a pyrimidone compound used as a Lp-PLA$_2$ inhibitor and a pharmaceutical composition thereof.

In the first aspect of the present invention there is provided a compound of general formula I, a stereoisomer, a deuterated form or a pharmaceutically acceptable salt thereof:

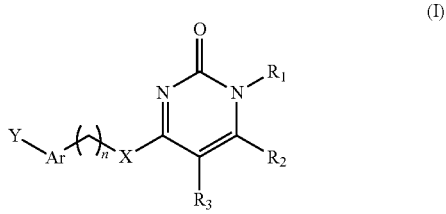

wherein, $R_1$ and $R_3$ are independently selected from the group consisting of H, $C_1$-$C_6$ alkyl, $C_3$-$C_8$ cycloalkyl, $C_6$-$C_{10}$ aryl, —$(CH_2)_q$-(3-8 membered heteroaryl);

$R_2$ is $C_1$-$C_6$ alkyl, $C_2$-$C_6$ alkenyl, $C_2$-$C_6$ alkynyl, $C_3$-$C_8$ cycloalkyl, 3-8 membered heterocyclic radical, —O-(3-8 membered heterocyclic radical), $C_3$-$C_8$ cycloalkenyl, $C_1$-$C_6$ alkoxy, $C_3$-$C_8$ cycloalkyloxy, $C_6$-$C_{10}$ aryl, —O—($C_6$-$C_{10}$ aryl), —OH, —CN, halogen, —$(CH_2)$m-(3-8 membered heteroaryl) or —$NR_4R_5$;

X is O, S, —$(CH_2)$m- or —$N(R_4)$—;

n is 0, 1, 2, 3 or 4;

Ar is $C_6$-$C_{10}$ aryl or 3-8 membered heteroaryl;

Y is absent, -A-($C_6$-$C_{10}$ aryl) or -A-(3-8 membered heteroaryl), wherein, A is O, S, —$(CH_2)$m- or —$N(R_4)$—, wherein, said $C_1$-$C_6$ alkyl, $C_2$-$C_6$ alkenyl, $C_2$-$C_6$ alkynyl, $C_1$-$C_6$ alkoxy, $C_3$-$C_8$ cycloalkyl, $C_3$-$C_8$ cycloalkenyl, 3-8 membered heteroaryl, —$(CH_2)_q$-(3-8 membered heteroaryl), 3-8 membered heterocyclic radical, and $C_6$-$C_{10}$ aryl are optionally substituted with a group selected from the group consisting of —OH, —CN, =O, $C_1$-$C_6$ alkyl, $C_6$-$C_{10}$ aryl, $C_1$-$C_6$ alkoxy, $C_1$-$C_6$ alkoxyacyl, $C_1$-$C_6$ alkanoyl, $C_1$-$C_6$ alkanoyloxy, $C_3$-$C_8$ cycloalkyl, 3-8 membered heterocyclic radical, —C(O)-3-8 membered heterocyclic radical, carboxyl, halogen, halo-$C_1$-$C_6$ alkyl, —$S(O)R_4$, —$SO_2R_4$, —$NO_2$, —$NR_4R_5$;

each $R_4$ and each $R_5$ are independently selected from the group consisting of H, $C_1$-$C_6$ alkyl, $C_1$-$C_6$ alkanoyl, —$(CH_2)_m$—($C_1$-$C_6$ alkoxy), $C_3$-$C_8$ cycloalkyl, $C_2$-$C_6$ alkenyl, $C_2$-$C_6$ alkynyl, 3-8 membered heterocyclic radical, $C_3$-$C_8$ cycloalkenyl and $C_6$-$C_{10}$ aryl;

each m is independently 0, 1, 2, 3 or 4.

q is independently 1, 2, 3 or 4.

In the present invention, the substitution is mono- or poly-substitution. In another preferred embodiment, the substitution is mono-substitution, di-substitution, tri-substitution or tetra-substitution. In another preferred embodiment, the polysubstitution means comprising a plurality of identical or different groups, such as two, three, or four groups.

In another preferred embodiment, said general formula I compounds have one or more of the following features:

(1) $R_1$ is H, $C_1$-$C_6$ alkyl or —$(CH_2)_q$-(3-8 membered heteroaryl), wherein, q is 1, 2 or 3; said $C_1$-$C_6$ alkyl, —$(CH_2)_q$-(3-8 membered heteroaryl) are optionally substituted with a group selected from the group consisting of $C_1$-$C_4$ alkyl, $C_6$-$C_{10}$ aryl, $C_1$-$C_4$ alkoxy, halogen, halo-$C_1$-$C_4$ alkyl;

(2) $R_3$ is H or $C_1$-$C_6$ alkyl; preferably, $R_3$ is H or $C_1$-$C_4$ alkyl; most preferably, $R_3$ is H;

(3) n is 1 or 2, (4) X is O, S, or —$N(R_4)$—, wherein, $R_4$ is H, $C_1$-$C_6$ alkyl, In a preferred embodiment, X is O, S, or —$N(R_4)$—, wherein $R_4$ is H, $C_1$-$C_4$ alkyl;

In another preferred embodiment, X is O, S, —NH, —$N(CH_3)$ or —$N(CH_2CH_3)$.

In another preferred embodiment, $R_1$ is $C_1$-$C_4$ alkyl or —$(CH_2)_q$-(3-6 membered heteroaryl), wherein q is 1 or 2; said —$(CH_2)_q$-(3-6 membered heteroaryl) are optionally substituted with a group selected from the group consisting of $C_1$-$C_4$ alkyl, $C_1$-$C_4$ alkoxy, halogen, halo-$C_1$-$C_4$ alkyl.

In another preferred embodiment, $R_1$ is methyl, ethyl, propyl, —$CH_2$-pyridyl or —$CH_2$-pyrazolyl, said pyridyl or pyrazolyl are optionally substituted with a group selected from the group consisting of methyl, ethyl, methoxy, ethoxy, fluoro, chloro, bromo, trifluoromethyl.

In another preferred embodiment, $R_2$ is $C_1$-$C_6$ alkyl, $C_3$-$C_8$ cycloalkyl, 3-8 membered heterocyclic radical, $C_1$-$C_6$ alkoxy, $C_6$-$C_{10}$ aryl, —$(CH_2)_m$-(3-8 membered heteroaryl) or —$NR_4R_5$, wherein, said 3-8 membered heterocyclic radical, $C_6$-$C_{10}$ aryl, —$(CH_2)_m$-(3-8 membered heteroaryl) are optionally substituted with a group selected from the group consisting of =O, $C_1$-$C_6$ alkyl, $C_6$-$C_{10}$ aryl, $C_1$-$C_6$ alkoxy, $C_3$-$C_8$ cycloalkyl, halogen, halo-$C_1$-$C_6$ alkyl;

$R_4$ and $R_5$ are independently selected from the group consisting of H, $C_1$-$C_6$ alkyl, —$(CH_2)_m$—($C_1$-$C_6$ alkoxy), $C_3$-$C_8$ cycloalkyl;

m is 0, 1, 2 or 3.

In another preferred embodiment, $R_2$ is $C_1$-$C_4$ alkyl, $C_3$-$C_6$ cycloalkyl, 5-6 membered heterocyclic radical, $C_1$-$C_4$ alkoxy, $C_6$-$C_{10}$ aryl, —$(CH_2)_m$-(5-6 membered heteroaryl) or —$NR_4R_5$, wherein, said 5-6 membered heterocyclic radical, $C_6$-$C_{10}$ aryl, —$(CH_2)_m$-(5-6 membered heteroaryl) are optionally substituted with a group selected from the group consisting of =O, $C_1$-$C_4$ alkyl, $C_6$-$C_{10}$ aryl, $C_1$-$C_4$ alkoxy, $C_3$-$C_6$ cycloalkyl, halogen, halo-$C_1$-$C_4$ alkyl; $R_4$ and $R_5$ are independently selected from the group consisting of H, $C_1$-$C_4$ alkyl, —$(CH_2)_m$—($C_1$-$C_4$ alkoxy), $C_3$-$C_6$ cycloalkyl; m is 0, 1 or 2.

In another preferred embodiment, $R_2$ is $C_1$-$C_4$ alkyl, 5-6 membered heterocyclic radical, $C_1$-$C_4$ alkoxy, $C_6$-$C_{10}$ aryl, -(5-6 membered heteroaryl) or —$NR_4R_5$, wherein, said 5-6 membered heterocyclic radical, $C_6$-$C_{10}$ aryl, -(5-6 membered heteroaryl) are optionally substituted with a group selected from the group consisting of =O, $C_1$-$C_4$ alkyl, phenyl, $C_1$-$C_4$ alkoxy, $C_3$-$C_6$ cycloalkyl, halogen, fluoro-$C_1$-$C_4$ alkyl; $R_4$ and $R_5$ are independently selected from the group consisting of $C_1$-$C_4$ alkyl, —$(CH_2)_2$—($C_1$-$C_4$ alkoxy), $C_3$-$C_6$ cycloalkyl.

In another preferred embodiment, $R_2$ is methyl, ethyl, propyl, methoxy, ethoxy, propoxy, pyrrolidinyl, piperidinyl, piperazinyl, thiomorpholinyl, morpholinyl, phenyl, naphthyl, thienyl, furyl, imidazolyl, thiazolyl, oxazolyl, pyridyl, pyrazolyl, pyrimidinyl or —$NR_4R_5$, wherein the pyrrolidinyl, piperidinyl, piperazinyl, thiomorpholinyl, morpholinyl, phenyl, naphthyl, thienyl, furyl, imidazolyl, thiazolyl, oxazolyl, pyridyl, pyrazolyl or pyrimidinyl are optionally substituted with a group selected from the group consisting of =O, methyl, ethyl, phenyl, methoxy, ethoxy, cyclopropyl, fluoro, chloro, bromo, trifluoromethyl;

$R_4$ and $R_5$ are independently selected from the group consisting of methyl, ethyl, propyl, —$(CH_2)_2OCH_3$ or cyclopropyl.

In another preferred embodiment, said general formula I compounds have one or two of the following features:

(1) Ar is substituted or unsubstituted phenyl, substituted or unsubstituted naphthyl, substituted or unsubstituted 5-6 membered heteroaryl, wherein said substitution means that the phenyl, naphthyl or 5-6 membered heteroaryl has 1-4 substituents selected from the group consisting of —CN, $C_1$-$C_6$ alkyl, $C_1$-$C_6$ alkoxy, halogen, hydroxyl, halo-$C_1$-$C_6$ alkyl, halo-$C_1$-$C_6$ alkoxy;

(2) Y is absent, -A-($C_6$-$C_{10}$ aryl) or -A-(5-6 membered heteroaryl), wherein, A is O or S; said $C_6$-$C_{10}$ aryl, or 5-6 membered heteroaryl optionally has 1-3 substituents selected from the group consisting of $C_1$-$C_4$ alkyl, —CN, halogen, halo-$C_1$-$C_6$ alkyl.

In another preferred embodiment, Ar is substituted or unsubstituted phenyl, substituted or unsubstituted 5-6 membered heteroaryl, wherein said substitution means that the phenyl or 5-6 membered heteroaryl has 1-3 substituents selected from the group consisting of —CN, $C_1$-$C_4$ alkyl, $C_1$-$C_4$ alkoxy, halogen, hydroxyl, halo-$C_1$-$C_4$ alkyl, halo-$C_1$-$C_4$ alkoxy.

In another preferred embodiment, Ar is substituted or unsubstituted phenyl, wherein said substitution means that the phenyl has 1-3 substituents selected from the group consisting of —CN, F, Cl, Br, trifluoromethyl, methyl, ethyl or propyl.

In another preferred embodiment, A is O. In another preferred embodiment, said $C_6$-$C_{10}$ aryl or 5-6 membered heteroaryl optionally has 1-3 substituents selected from the group consisting of —CN, F, Cl, $CF_3$.

In another preferred embodiment, said compound has a structure represented by formula (IA):

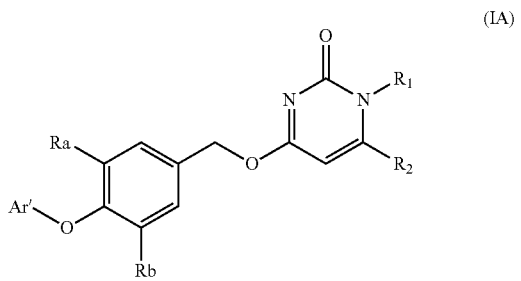

(IA)

wherein, Ra and Rb each independently are H, halogen, —CN or methyl;
$R_1$ is methyl, ethyl, propyl, —$CH_2$-pyridyl or —$CH_2$-pyrazolyl;
$R_2$ is methyl, methoxy, pyrrolidinyl, piperidinyl, piperazinyl, thiomorpholinyl, morpholinyl, phenyl, thienyl, pyridyl, pyrazolyl, pyrimidinyl or —$NR_4R_5$, wherein said pyrrolidinyl, piperidinyl, piperazinyl, thiomorpholinyl, morpholinyl, phenyl, thienyl, pyridyl, pyrazolyl or pyrimidinyl optionally is substituted with one or more, the same or different groups selected from the following group consisting of =O, methyl, phenyl, methoxy, F, trifluoromethyl;
$R_4$ and $R_5$ are independently selected from the group consisting of methyl, ethyl, —$(CH_2)_2OCH_3$ or cyclopropyl;
Ar' is phenyl, pyridyl, pyrimidinyl, wherein, said phenyl, pyridyl, pyrimidinyl optionally is substituted with one or more, the same or different groups selected from the following group consisting of trifluoromethyl, F, Cl, cyano, methyl.

In another preferred embodiment, said general formula I compound is any one of the compounds prepared in Example 1 to Example 83.

In another preferred embodiment, said pharmaceutically acceptable salt is hydrochloride, hydrobromide, sulfate, nitrate, phosphate, citrate, methanesulfonate, trifluoroacetate, acetate, oxalate, succinate, malate, tosylate, tartrate, fumarate, glutamate, glucuronate, lactate, glutarate, arginine salt or maleate.

In the second aspect of the present invention there is provided a preparation method of the compound of general formula I, stereoisomer, deuterated form or pharmaceutically acceptable salt thereof according to the first aspect, comprising the following steps:

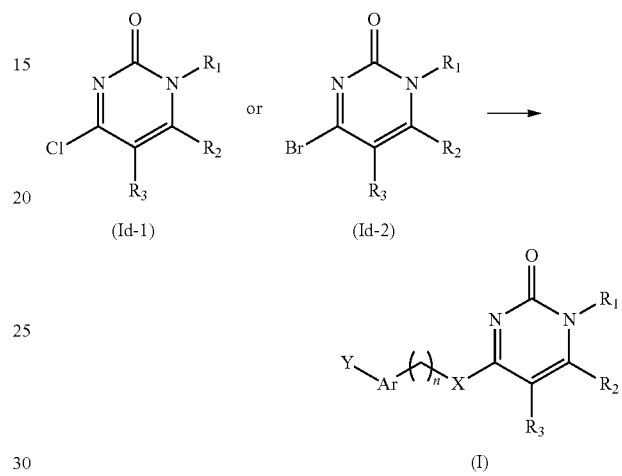

reacting a formula Id-1 compound or formula Id-2 compound with Y—Ar—$(CH_2)_n$XH to obtain said general formula I compound;

or said preparation method comprises the following steps:

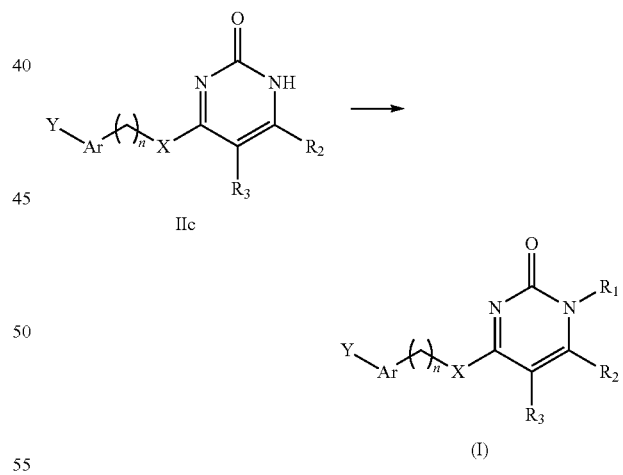

reacting a formula IIc compound with $R_1Z$ to obtain said general formula I compound,
wherein, Z is F, Cl, Br or I,
wherein, $R_1$, $R_2$, $R_3$, Y, Ar, n, and X are defined as in the first aspect.

In the third aspect of the present invention there is provided a pharmaceutical composition comprising the compound of general formula I, a stereoisomer, a deuterated form or a pharmaceutically acceptable salt thereof according to the first aspect; and
a pharmaceutically acceptable carrier.

In the fourth aspect of the present invention there is provided a use of the compound of general formula I, a stereoisomer, a deuterated form or a pharmaceutically acceptable salt thereof according to the first aspect or a use of the pharmaceutical composition according to the third aspect, wherein the use is in:

(1) the manufacture of a medicament for inhibiting Lp-PLA$_2$;

(2) the manufacture of a medicament for preventing and/or treating and/or alleviating a disease associated with the Lp-PLA$_2$ enzyme activity;

(3) the manufacture of a medicament for reducing glycosylated hemoglobin level and/or up-regulating insulin level;

(4) the manufacture of a medicament for down-regulating triglyceride level or low-density lipoprotein level; and/or (5) the manufacture of a medicament for down-regulating urinary albumin level in urine.

In another preferred embodiment, said disease associated with the Lp-PLA$_2$ enzyme activity is atherosclerosis, diabetes, diabetic eye diseases, diabetic macular edema, kidney diseases, diabetic nephropathy, hypertension, angina, rheumatoid arthritis, stroke, myocardial infarction, post ischemia-and-reperfusion conditions, psoriasis, brain inflammatory diseases, Alzheimer's disease, various neuropsychiatric disorders, schizophrenia, ischemia-reperfusion injury, sepsis, acute inflammatory diseases, chronic inflammatory diseases, neurodegenerative diseases, glaucoma macular degeneration or Alzheimer's disease.

In another preferred embodiment, the diseases associated with the Lp-PLA$_2$ enzyme activity include atherosclerosis, diabetes, diabetic eye diseases, kidney diseases, diabetic nephropathy.

In another preferred embodiment, the disease associated with the Lp-PLA$_2$ enzyme activity is atherosclerosis, diabetes, diabetic macular edema, or Alzheimer's disease.

In the fifth aspect of the present invention there is provided an intermediate of said general formula I compound, which has the structure:

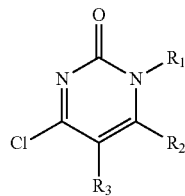

(Id-1)

wherein, $R_1$, $R_2$, and $R_3$ are defined as in the first aspect.

In another preferred embodiment, $R_3$ is H, $C_1$-$C_6$ alkyl, $C_3$-$C_8$ cycloalkyl, $C_6$-$C_{10}$ aryl or —(CH$_2$)$_q$-(3-8 membered heteroaryl), preferably $R_3$ is H or $C_1$-$C_6$ alkyl, more preferably, $R_3$ is H or $C_1$-$C_4$ alkyl, most preferably, $R_3$ is H; $R_1$ is H, $C_1$-$C_6$ alkyl, —(CH$_2$)$_q$-(3-8 membered heteroaryl); q is independently 1, 2, 3 or 4; $R_2$ is $C_1$-$C_6$ alkyl, $C_2$-$C_6$ alkenyl, $C_2$-$C_6$ alkynyl, $C_3$-$C_8$ cycloalkyl, 3-8 membered heterocyclic radical, —O-(3-8 membered heterocyclic radical), $C_3$-$C_8$ cycloalkenyl, $C_1$-$C_6$ alkoxy, $C_3$-$C_8$ cycloalkyloxy, $C_6$-$C_{10}$ aryl, —O—($C_6$-$C_{10}$ aryl), —OH, —CN, halogen, —(CH$_2$)$_m$-(3-8 membered heteroaryl) or —NR$_4$R$_5$; preferably is $C_1$-$C_6$ alkyl, $C_3$-$C_8$ cycloalkyl, 3-8 membered heterocyclic radical, $C_1$-$C_6$ alkoxy, $C_6$-$C_{10}$ aryl, —(CH$_2$)$_m$-(3-8 membered heteroaryl) or —NR$_4$R$_5$, said 3-8 membered heterocyclic radical, $C_6$-$C_{10}$ aryl, —(CH$_2$)$_m$-(3-8 membered heteroaryl) are optionally substituted with a group selected from the group consisting of =O, $C_1$-$C_6$ alkyl, $C_6$-$C_{10}$ aryl, $C_1$-$C_6$ alkoxy, $C_3$-$C_8$ cycloalkyl, halogen, halo-$C_1$-$C_6$ alkyl; each m is independently 0, 1, 2, 3 or 4; with the proviso that $R_1$ and $R_2$ are not both methyl and even not both $C_1$-$C_6$ alkyl at the same time.

In the sixth aspect of the present invention there is provided an intermediate of said general formula I compound, which has the structure:

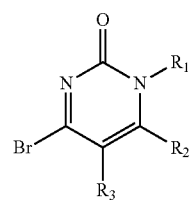

(Id-2)

wherein, $R_1$, $R_2$, and $R_3$ are defined as in the first aspect.

In the seventh aspect of the present invention there is provided an intermediate of said general formula I compound, which has the structure:

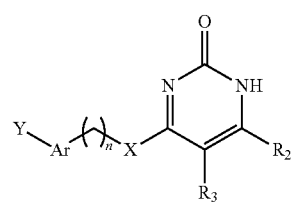

(IIc)

wherein, $R_2$, $R_3$, Y, Ar, n, and X are defined as in the first aspect.

In another preferred embodiment, Y is -A-($C_6$-$C_{10}$ aryl) or -A-(3-8 membered heteroaryl), wherein the definition is the same as described above.

In the eighth aspect of the present invention, there is provided a method for inhibiting Lp-PLA$_2$, which comprises administering a safe and effective amount of said general formula I compound to a subject in need or to the environment.

In the ninth aspect of the present invention, there is provided a method for treating a disease associated with the Lp-PLA$_2$ enzyme activity, which comprises administering a safe and effective amount of said general formula I compound to a subject in need.

In another preferred embodiment, the subject in need includes in vitro cultured cells, human or non-human mammals, preferably human, mouse or rat.

In the present invention, "a safe and effective amount" means that the amount of the active ingredient (said general formula I compound) is sufficient to significantly improve the condition of disease without causing serious side effects.

It is to be understood that within the scope of the present invention, each foregoing technical feature of the present invention and each technical feature described in detail below (e.g., examples) may be combined with each other to constitute a new or preferred technical solution which needs not be described one by one herein due to the space limitation of the specification.

DETAILED DESCRIPTION OF THE INVENTION

Figure 1:
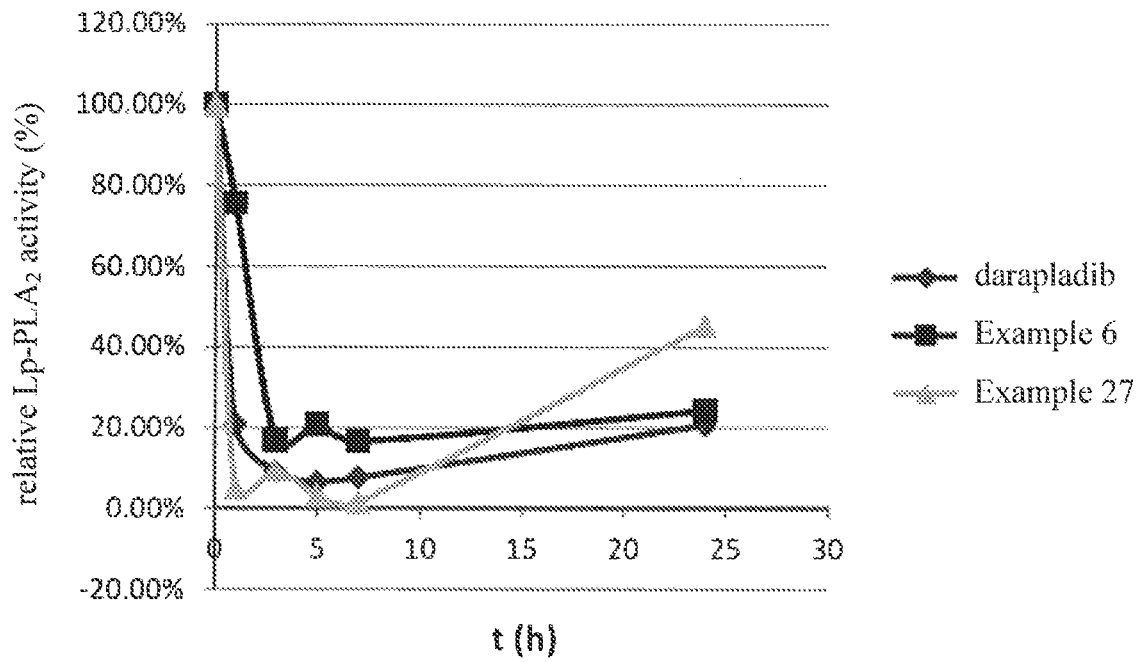
FIG. 1 shows the activity of Lp-PLA$_2$ in the serum of SD rats after single administration.

Based on a long-term and in-depth study, the inventors have developed for the first time a structurally novel pyrimidone compound which can be used as a Lp-PLA$_2$ inhibitor for preventing and/or treating and/or alleviating a disease associated with the Lp-PLA$_2$ enzyme activity. On such basis, the present invention has been completed.

Terms

In the present invention, the term "$C_1$-$C_6$ alkyl" refers to a straight or branched chain alkyl having 1 to 6 carbon atoms, and includes, without limitation, methyl, ethyl, propyl, isopropyl, butyl and the like; and the term "$C_1$-$C_4$ alkyl" has a similar meaning. The term "$C_2$-$C_6$ alkenyl" refers to a straight or branched alkenyl containing one double bond and having 2 to 6 carbon atoms, and includes, without limitation, vinyl, propenyl, butenyl, isobutenyl, pentenyl and hexenyl. The term "$C_2$-$C_6$ alkynyl" refers to a straight or branched alkynyl containing one triple bond and having 2 to 6 carbon atoms, and includes without limitation ethynyl, propynyl, butynyl, isobutynyl, pentynyl and hexynyl. The term "halo-$C_1$-$C_6$ alkyl" refers to an alkyl substituted with one or more halogen atoms, such as —$CH_2F$, —$CF_3$, —$CH_2CHF_3$ and the like.

In the present invention, the term "$C_1$-$C_6$ alkoxy" means a straight or branched chain alkoxy group having 1 to 6 carbon atoms, and includes, without limitation, methoxy, ethoxy, propoxy, isopropoxy and butoxy, and the like; the term "$C_1$-$C_4$ alkoxy" has a similar meaning.

In the present invention, the term "$C_3$-$C_8$ cycloalkyl" refers to a cyclic alkyl having 3 to 8 carbon atoms on the ring, and includes, without limitation, cyclopropyl, cyclobutyl, cyclopentyl, cyclohexyl, cycloheptyl, and the like; the term "$C_3$-$C_6$ cycloalkyl" has a similar meaning. The term "$C_3$-$C_8$ cycloalkenyl" refers to a cyclic alkenyl having 3 to 8 carbon atoms on the ring, and includes, without limitation, cyclopropenyl, cyclobutenyl, cyclopentenyl, cyclohexenyl and the like.

In the present invention, the term "aryl" means a hydrocarbyl containing one or more aromatic rings, such as phenyl or naphthyl. The term "heteroaryl" refers to an aromatic ring group containing 1 to 4 heteroatoms selected from N, O, and S and includes, without limitation, pyrazolyl, thienyl, pyridyl, pyrimidinyl, pyrazinyl, pyridazinyl, furyl, pyrrolyl, oxazolyl, isoxazolyl, imidazolyl, thiazolyl, isothiazolyl, quinazolinyl, quinolyl, isoquinolyl and indolyl.

In the present invention, the term "heterocyclic radical" refers to a cycloalkyl containing 1 to 4 heteroatoms selected from N, O, and S, and includes, without limitation, pyrrolidinyl, morpholinyl, piperidinyl, thiomorpholinyl, piperazinyl, tetrahydrofuryl, tetrahydropyranyl, tetrahydrothienyl, tetrahydrothiazolyl.

Compound of the Present Invention

As used herein, the term "compound of the invention" refers to the compound of formula I, a stereoisomer thereof, or a pharmaceutically acceptable salt thereof. In addition, the term also includes the partial or totally deuterated form of the compound of formula I or a pharmaceutically acceptable salt thereof.

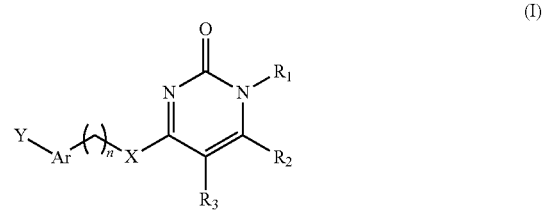

(I)

wherein, $R_1$, $R_2$, $R_3$, X, Y and Ar are defined as above.

As used herein, the term "pharmaceutically acceptable salt" refers to a salt suitable for use as a medicament formed by a compound of the invention with an acid or base. Pharmaceutically acceptable salt includes inorganic salts and organic salts. Suitable acids for forming salts include, but are not limited to, inorganic acids such as hydrochloric acid, hydrobromic acid, hydrofluoric acid, sulfuric acid, nitric acid, phosphoric acid and the like; organic acids such as formic acid, acetic acid, propionic acid, oxalic acid, malonic acid, succinic acid, fumaric acid, maleic acid, lactic acid, malic acid, tartaric acid, citric acid, picric acid, methanesulfonic acid, benzenemethane sulfonic acid, benzenesulfonic acid and the like; and acidic amino acids such as aspartic acid and glutamic acid. Suitable bases for forming salts include, but are not limited to, alkali metal hydroxides (such as lithium hydroxide, sodium hydroxide, potassium hydroxide and the like).

Preparation Method

The compound of formula I, stereoisomer, deuterated form or pharmaceutically acceptable salt thereof can be prepared by the following method:

Route 1

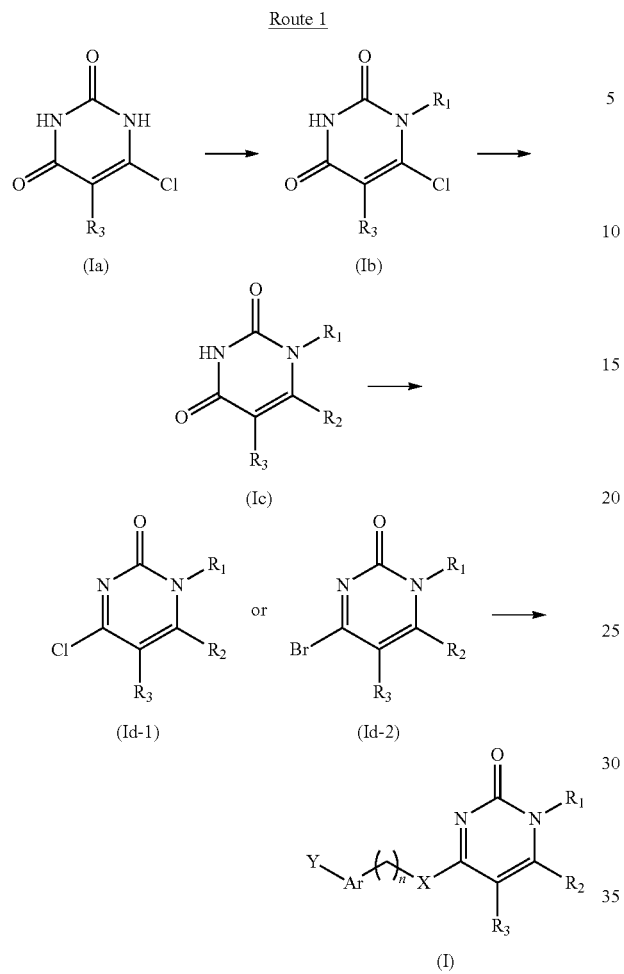

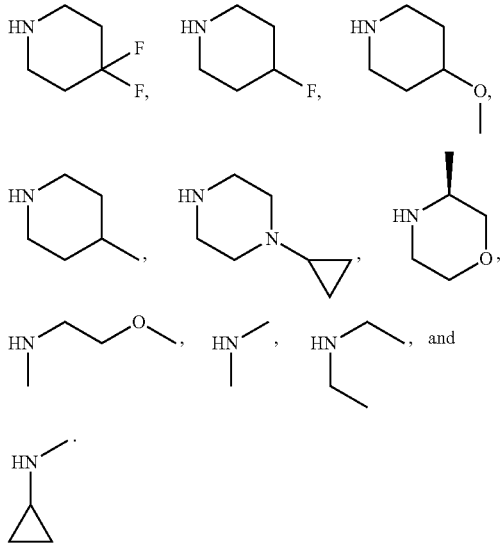

(a) reacting a formula Ia compound with R₁Z in the presence of a base to give a formula Ib compound;

(b) reacting the formula Ib compound with a corresponding nucleophile through nucleophilic substitution, or with a corresponding boronic acid or boronate through Suzuki coupling reaction, to give a formula Ic compound;

(c) reacting the formula Ic compound with phosphorus oxychloride to give a formula Id-1 compound, or reacting the formula Ic compound with phosphorus tribromide to give a formula Id-2 compound;

(d) reacting the formula Id-1 compound or formula Id-2 compound with Y—Ar—(CH₂)ₙXH in the presence of a base to give the formula I compound.

In another preferred embodiment, said nucleophile is R₂H, R₂ is defined as above. Preferably, R₂H is selected from

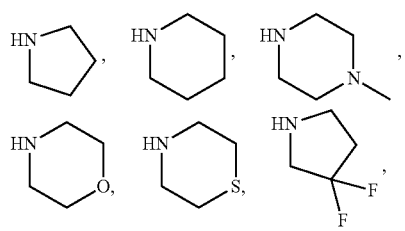

In another preferred embodiment, said boronic acid or boronate is selected from

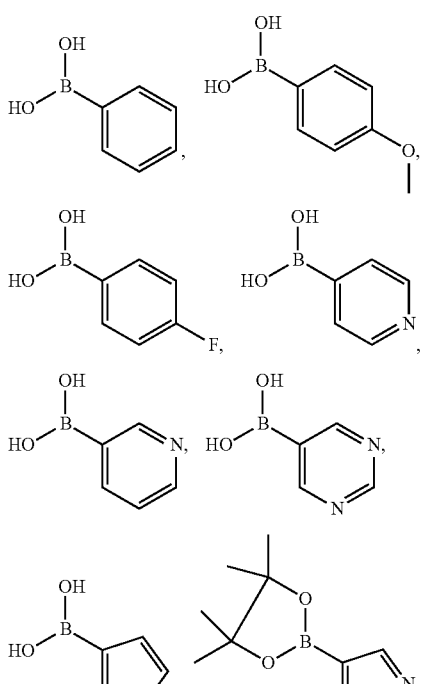

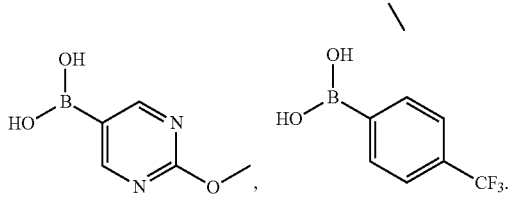

Route 2:

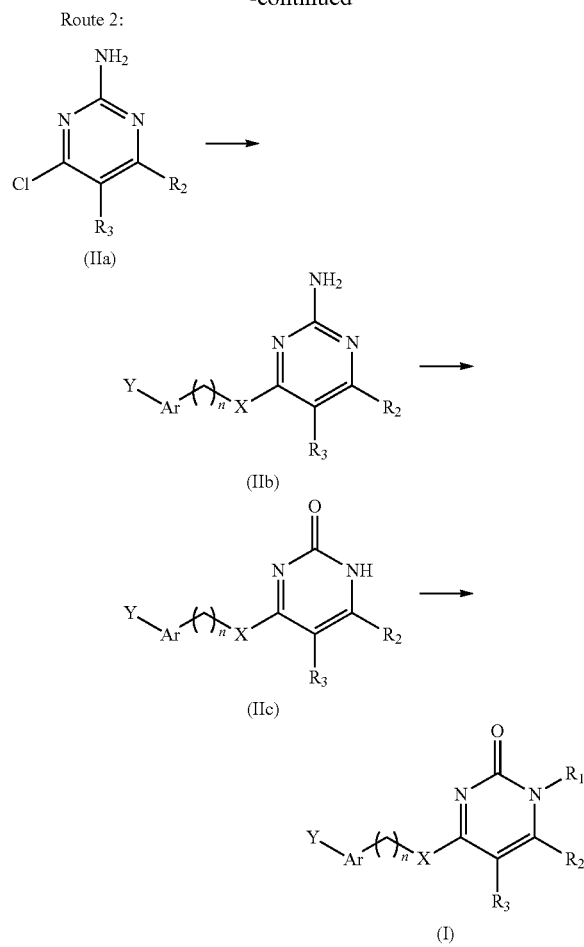

(i) reacting a formula IIa compound with Y—Ar—(CH$_2$)$_n$XH in the presence of a base to give a formula IIb compound;

(ii) dissolving the III) compound in acetic acid and adding NaNO$_2$ to give a formula IIc compound;

(iii) reacting the formula IIc compound with R$_1$Z in the presence of a base to give formula I compound, wherein, Z is F, Cl, Br or I; R$_1$, R$_2$, R$_3$, Y, Ar, n, and X are defined as above.

The base in step (a), (d), (i) or (iii) is selected from the group consisting of inorganic base, organic base and combinations thereof; preferably, the inorganic base is selected from the group consisting of sodium hydroxide, potassium hydroxide, strontium hydroxide, lithium hydroxide, barium hydroxide, calcium hydroxide, cesium hydroxide, sodium bicarbonate, potassium bicarbonate, potassium carbonate, sodium carbonate, strontium carbonate, cesium carbonate, sodium sulfide, sodium hydrogen and combinations thereof. The organic base is selected from the group consisting of sodium alkoxide, potassium alkoxide, butyllithium, 1,8-diazacyclo[5,4,0]undecene-7, pyridine, piperidine, pyrrolidine, morpholine, N-methylmorpholine, quinoline, 4-dimethylaminopyridine, triethylamine, diethylamine, tri-n-butylamine, tripropylamine, diisopropylamine, diisopropylethylamine and combinations thereof; more preferably, the base is selected from the group consisting of sodium hydroxide, potassium hydroxide, lithium hydroxide, sodium bicarbonate, potassium bicarbonate, potassium carbonate, sodium carbonate, cesium carbonate, sodium hydrogen, sodium methoxide, sodium ethoxide, potassium tert-butoxide, pyridine, piperidine, pyrrolidine, morpholine, N-methylmorpholine, triethylamine, diethylamine, diisopropylamine, diisopropylethylamine and combinations thereof. The reaction solvent of the reaction is selected from the group consisting of aromatic hydrocarbon solvent, ether solvent, halogenated hydrocarbon solvent and other solvent; preferably, the aromatic hydrocarbon solvent is selected from the group consisting of benzene, toluene, xylene, chlorobenzene, nitrobenzene and combinations thereof; the ether solvent is selected from the group consisting of tetrahydrofuran, diethyl ether, glycol dimethyl ether, diethylene glycol dimethyl ether, diethylene glycol monomethyl ether, dioxane and combinations thereof; the halogenated hydrocarbon solvent is selected from the group consisting of dichloromethane, chloroform, carbon tetrachloride, dichloroethane and combinations thereof; said other solvent is selected from the group consisting of N,N-dimethylformamide, N,N-dimethyl acetamide, dimethylsulfoxide, N-methylpyrrolidone, hexamethylphosphoramide, acetone, acetonitrile, ethyl acetate and combinations thereof. Preferably, the reaction temperature of the reaction is from −30° C. to 300° C., more preferably from −10° C. to 150° C.; preferably, the reaction time of the reaction is 0.5 to 12 hours.

Use

The compounds of the present invention are Lp-PLA$_2$ inhibitors. Therefore, these compounds can be useful for treatment, for example, for the treatment of conditions associated with the activity of Lp-PLA$_2$. Accordingly, another aspect of the present invention relates to the treatment of a condition associated with the activity of Lp-PLA$_2$. It will be understood by those skilled in the art that a particular disorder or its treatment may involve one or more underlying mechanisms associated with Lp-PLA$_2$ activity, including one or more of the mechanisms described herein.

In an embodiment, the compounds of the present invention can be used in the treatment of any disease involving endothelium dysfunction, such as atherosclerosis, diabetes, hypertension, angina and conditions after ischemia and reperfusion.

In an embodiment, the compounds of the present invention can be used in the treatment of any disease involving lipid oxidation associated with enzymatic activity, for example, other conditions in addition to such as atherosclerosis, diabetes and the like, such as rheumatoid arthritis, stroke, brain inflammatory conditions such as Alzheimer's disease, various neuropsychiatric disorders such as schizophrenia, myocardial infarction, ischemia, reperfusion injury, sepsis, as well as acute and chronic inflammation.

In an embodiment, the compounds of the present invention can be used in the treatment of diseases involving activated monocytes, macrophages or lymphocytes, since all of these cell species express Lp-PLA$_2$, including diseases involving activated macrophages, typical disorders include but not limited to psoriasis, rheumatoid arthritis, wound healing, chronic obstructive pulmonary disease, cirrhosis, atopic dermatitis, emphysema, chronic pancreatitis, chronic gastritis, aortic aneurysm, atherosclerosis, multiple sclerosis, Alzheimer's disease and autoimmune diseases such as lupus.

In an embodiment, the present invention provides a method of treating a disease associated with the Lp-PLA$_2$ activity comprising treating a subject in need of treatment with an effective amount of an Lp-PLA$_2$ inhibitor. The disease may be associated with increased involvement of monocytes, macrophages or lymphocytes; associated with the formation of lysophosphatidylcholine and oxidized free fatty acids; associated with lipid oxidation involving the Lp-PLA$_2$ activity; or associated with endothelial dysfunction.

In other embodiments, the compounds of the present invention may be used for primary or secondary prophylaxis of acute coronary events, used in a combined therapy for the prophylaxis of restenosis, or used for delaying the development of diabetes or hypertensive renal insufficiency. prophylaxis includes treating a subject at risk of having such a condition.

In some embodiments, the compounds of the present invention can be used in combination with anti-hyperlipidemia agents, anti-atherosclerotic agents, anti-diabetic agents, anti-angina agents or anti-hypertensive agents or agents for lowering lipoprotein a to treat the diseases described in the present invention. Examples of such agents include, but are not limited to, cholesterol synthesis inhibitors such as statins; antioxidants such as probucol; insulin sensitizers; calcium channel antagonists and antiinflammatory agents such as nonsteroidal antiinflammatory drugs.

In one embodiment, the compounds of the present invention can be used in the treatment of a neurodegenerative disease in a subject. The method comprises administering a pharmaceutical composition comprising a drug that can inhibit the Lp-PLA$_2$ activity to a subject in need of such treatment. Exemplary neurodegenerative diseases include, but are not limited to, Alzheimer's disease; vascular dementia, Parkinson's disease and Huntington's chorea. In an embodiment, the neurodegenerative disease of the present invention is associated with an abnormal blood-brain barrier. In an embodiment, the subject administered with an agent that can inhibit the Lp-PLA$_2$ activity is human.

In one embodiment, the present invention provides a method of treating a subject suffering from vascular dementia or having a risk of vascular dementia. Said method comprises administering a pharmaceutical composition comprising an effective amount of the compound of the invention to a subject. In an embodiment, the vascular dementia is associated with Alzheimer's disease.

In an embodiment, the present invention provides a method of treating a neurological disorder associated with abnormal function of blood brain barrier, inflammation, or microglia activation in a subject in need of treatment. Said method comprises administering an effective amount of a compound of the invention to the subject. In another embodiment, the abnormal blood-brain barrier is a permeable blood-brain barrier. In another embodiment, the disease is a neurodegenerative disease. Such neurodegenerative disease is such as, but not limited to, vascular dementia, Alzheimer's disease, Parkinson's disease, and Huntington's disease. In one embodiment, the present invention provides a method of treating a disease associated with blood-brain barrier leakage in a subject. Exemplary diseases include, but are not limited to, cerebral hemorrhage, cerebral amyloid angiopathy. In one embodiment, the neurodegenerative disease is Alzheimer's disease. In one embodiment, the neurodegenerative disease is vascular dementia. In one embodiment, the neurodegenerative disease is multiple sclerosis.

In an embodiment, the present invention provides a method of reducing the accumulation of beta amyloid protein in the brain of a subject. Said method comprises administering to a subject in need of treatment a pharmaceutical composition comprising an effective amount of a compound of the invention. In another embodiment, the beta amyloid protein is Aβ-42.

In an embodiment, when the subject is administered an effective amount of a compound of the invention, the method may further comprise administering to the subject another therapeutic agent for treating a neurodegenerative disease or a complication of the subject undergoing treatment. For example, when the neurodegenerative disease is similar to Alzheimer's disease, the subject may be treated with other agents targeted to Alzheimer's disease, such as donepezil, tacrine, rivastigmine, galanthamine, anti-amyloid protein vaccine, Aβ reduction therapy, thinking practice or stimulation.

In an embodiment, the present invention relates to a method of treating metabolic bone disease by administering an effective amount of a compound of the invention to a subject in need of treatment. Exemplary metabolic bone diseases include diseases associated with loss of bone mass and bone density, including but not limited to osteoporosis and osteopenia-related diseases. Exemplary osteoporosis and osteopenia-related diseases include, but are not limited to, bone marrow abnormalities, dyslipidemia, Paget's disease, type II diabetes, metabolic syndrome, insulin resistance, hyperparathyroidism and related diseases. In another embodiment, the subject in need of treatment is human.

It is contemplated that methods of preventing osteoporosis and/or osteopenia disorders described herein may be affected by inhibition of Lp-PLA$_2$ expression and/or inhibition of Lp-PLA$_2$ protein activity. Thus, some embodiments of the present invention provide methods of blocking enzyme activity to inhibit Lp-PLA$_2$. In another embodiment, a method of inhibiting Lp-PLA$_2$ by reducing and/or down-regulating the expression of Lp-PLA$_2$ RNA is provided. In another embodiment, the prevention and/or reduction of loss of bone mass and/or loss of bone density results in the prevention or reduction of symptoms associated with metabolic bone diseases such as osteoporosis and/or osteopenia disease.

In an embodiment, the method further comprises administering to the subject in need of treatment other therapeutic agent(s) for the treatment of metabolic bone diseases. For example, when the metabolic bone disease is osteoporosis, other therapeutic agent(s), such as bisphosphonates, may be used.

One aspect of the present invention provides a method of treating an eye disease by administering an effective amount of a compound of the invention. The eye disease to which the present invention is applicable may be related to the destruction of the blood-retina barrier. Exemplary eye diseases involve diabetic eye diseases and include the disorders such as macular edema, diabetic retinopathy, and the like. In addition, in one embodiment, the present invention relates to a method of treating an eye disease by administering a compound of the invention to inhibit Lp-PLA$_2$. Exemplary eye diseases include, but are not limited to, central retinal vein occlusion, retinal branch vein occlusion, irvine-gass syndrome, pigmented retinitis, flat inflammation, birdshot retino choroidopathy, retinal outer membrane, choroidal tumors, cystic macular edema, parafoveal telangiectasis, traction macular disease, vitreous macular traction syndrome, retinal detachment, optic nerve retinitis, idiopathic macular edema and the like.

In addition, some embodiments of the present invention provide methods for treating diabetic macular edema in a subject. Said method comprises administering an effective amount of a compound of the invention to a subject in need of treatment. In an embodiment, the present invention provides a method for treating a subject suffering from macular edema or having a risk of macular edema. Said method comprises administering an effective amount of a compound of the invention to the subject. In another embodiment, the macular edema is associated with a diabetic eye disease, such as diabetic retinopathy. In another embodiment, the macular edema is associated with posterior uveitis.

In an embodiment, the present invention provides a method of treating glaucoma or macular degeneration. Said method comprises administering an effective amount of a compound of the invention to a subject.

In one embodiment, the present invention provides a method of treating a disease associated with the destruction of the blood-retina barrier in a subject in need of treatment. Said method comprises administering an effective amount of a compound of the invention to the subject.

In one embodiment, a systemic inflammatory disease, such as adolescent rheumatoid arthritis, inflammatory bowel disease, Kawasaki disease, multiple sclerosis, sarcoidosis, polyarteritis, psoriatic arthritis, reactive arthritis, systemic lupus erythematosus, Vogt-Koyanagi-Harada syndrome, lyme disease, Behcet's disease, ankylosing spondylitis, inflammatory granulomatous disease, enthesitis, may be the underlying cause of the posterior uveitis of retina and it can cause macular edema. The present invention relates to a method of treating posterior uveitis or anyone of these systemic inflammatory diseases by administering an effective amount of a compound of the present invention.

In one embodiment, the compounds of the present invention can significantly reduce the blood glucose level of spontaneous type 2 diabetes, significantly lower the level of glycosylated hemoglobin, and upregulate the level of insulin, thereby having a promising prospect to be used in the treatment of diabetes.

In one embodiment, the compounds of the present invention can significantly downregulate the triglyceride level and low density lipoprotein level in spontaneous type 2 diabetes, whereas have no significant effect on high density lipoproteins, thereby having a promising prospect to be used against dyslipidemia diseases, such as atherosclerosis.

In one embodiment, the compounds of the present invention can significantly downregulate the urinary albumin level in the urine of spontaneous type 2 diabetes, thereby having a promising prospect to be used against kidney diseases, such as diabetic nephropathy.

Method of Use

The compounds and pharmaceutical compositions provided by the present invention may be in a variety of forms such as tablets, capsules, powders, syrups, solutions, suspensions, aerosols and the like, and may be present in a suitable solid or liquid carrier or dilution. The pharmaceutical composition of the present invention may also be stored in a suitable sterilized utensil for injection or infusion. The pharmaceutical composition may also contain odorants, flavoring agents and the like.

In the present invention, the pharmaceutical composition contains a compound represented by formula (I) or a pharmaceutically acceptable salt thereof in a safe and effective amount (e.g., 0.1 to 99.9 parts by weight, preferably 1 to 90 parts by weight), and a residual amount of a pharmaceutically acceptable excipient, wherein the total weight of the composition is 100 parts by weight. Alternatively, the pharmaceutical composition according to the present invention contains a compound represented by formula (I) or a pharmaceutically acceptable salt thereof in an amount of 0.1 to 99.9% by weight on the basis of the total weight, preferably 1 to 90% by weight on the basis of the total weight, and a residual amount of a pharmaceutically acceptable excipient, wherein the total weight of the composition is 100 parts by weight.

The preferred ratio of the compound of formula (I) to the pharmaceutically acceptable carrier, excipient or sustained release agent is that the formula (I) compound as active ingredient accounts for more than 60% of the total weight, and the remainder accounts for 0 to 40% of the total weight. Preferably 1 to 20%, most preferably 1 to 10%.

The compound of formula (I) or the pharmaceutical composition containing the compound of formula (I) according to the present invention may be clinically administered to a mammal, including human and animal, and the route of administration may include oral, nasal inhalation, transdermal absorption, pulmonary or gastrointestinal tract administration, and the like. The preferred route of administration is oral. Preferably, it is in a unit dosage form, and each dosage contains an active ingredient of 0.01 mg to 200 mg, preferably 0.5 mg to 100 mg, administered in one or more times. Regardless of the method of administration, the optimal dose of an individual should be adjusted based on the specific treatment. Normally, starting from a small dose, the dose is gradually increased until the most appropriate dose is found.

The pharmaceutical compositions of the present invention can be administered by oral and intravenous, intramuscular or subcutaneous routes. Preferred pharmaceutical compositions are solid compositions, particularly tablets and solid filled or liquid filled capsules, from the standpoint of ease of preparation and administration. Oral administration of pharmaceutical compositions is preferred.

The features mentioned above, or the features mentioned in the examples, may be combined in any manner. All features disclosed in this specification may be used in conjunction with any form of the composition, and each of the features disclosed in the specification may be substituted by any alternative feature that can achieve the same, equal or similar purpose. Thus, unless otherwise specified, the features disclosed are only general examples of equal or similar features.

The present invention will be further described with reference to specific examples. It is to be understood that these examples are merely illustrative of the invention and are not intended to limit the scope of the invention. The experimental methods not specifically specified in the following examples are generally carried out according to conventional conditions such as those described in Sambrook et al., Molecular Cloning: Laboratory Manual (New York: Cold Spring Harbor Laboratory Press, 1989), or in accordance with the conditions recommended by the manufacturers. Unless otherwise stated, the percentages and parts are by weight.

Unless otherwise defined, all professional and scientific terms used herein are of the same meaning as those skilled in the art are familiar with. In addition, any method and material similar to or equivalent to the contents described may be applied to the method of the present invention. The preferred embodiments and materials described herein are for exemplary purposes only.

PREPARATION EXAMPLES

Intermediate 1—6-chloro-1methylpyrimidine-2,4(1H,3H)-dione

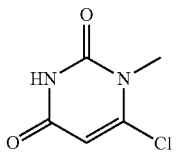

6-chloro-uracil (7 g, 1 eq.), methyl iodide (8.9 ml, 3 eq.) and anhydrous potassium carbonate (3.36 g, 0.5 eq.) were stirred in 30 ml of dimethylsulfoxide at room temperature for 3 h, then 38 ml of water was added and stirred in ice bath for 2 h. A white solid precipitated and the precipitate was collected by filtration and dried to give 5.12 g of a solid. MS (ESI): 161(M+H)

Intermediate 2—6-chloro-1ethylpyrimidine-2,4(1H,3H)-dione

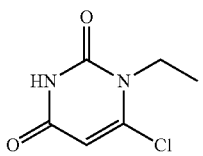

6-chloro-uracil (100 mg, 1 eq.), ethyl iodide (165 ul, 3 eq.) and anhydrous potassium carbonate (47 mg, 0.5 eq.) were stirred in 2 ml of dimethylsulfoxide at room temperature for 3 h, and then 3 ml of water was added. The mixture was extracted with ethyl acetate twice, rinsed three times with saturated brine, dried over magnesium sulfate, filtered and separated by column chromatograph to give 130 mg of a white solid. MS (ESI): 175(M+H).

Intermediate 3—6-chloro-1propylpyrimidine-2,4(1H,3H)-dione

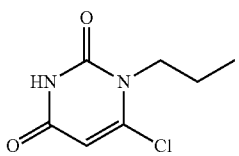

6-chloro-uracil (300 mg, 1 eq.), bromopropane (560 ul, 3 eq.) and anhydrous potassium carbonate (141 mg, 0.5 eq.) were stirred in 6 ml of dimethylsulfoxide at room temperature for 3 h, and then 8 ml of water was added. The mixture was extracted with ethyl acetate twice, rinsed three times with saturated brine, dried over magnesium sulfate, filtered and separated by column chromatograph to give 220 mg solid. MS (ESI): 189(M+H).

Intermediate 4—4-chloro-1-methyl-6-(pyrrolidinyl)pyrimidin-2(1H)-one

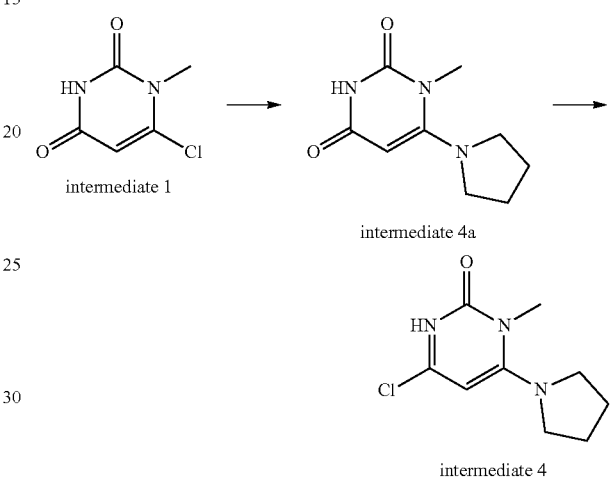

Intermediate 1 (300 mg, 1 eq.) and tetrahydropyrrole (930 ul, 6 eq.) were dissolved in 5 ml of absolute ethanol and stirred at 70° C. for 0.5 h. After the mixture was cooled, the ethanol was distilled off and water was added. The mixture was extracted twice with dichloromethane, rinsed once with saturated brine, dried over magnesium sulfate, filtered and the solvent was evaporated to give 310 mg of intermediate 4a. MS (ESI): 196 (M+H).

The intermediate 4a (100 mg) was dissolved in phosphorus oxychloride (5 ml), stirred at 90° C. for 4 h, cooled, evaporated to remove phosphorus oxychloride, adjusted with 1N NaOH to neutral pH, extracted three times with methylene chloride, dried over sodium sulfate, separated by column chromatography to give 90 mg of intermediate 4. MS (ESI): 214 (M+H).

The following intermediates were prepared by referring to the preparation method of intermediate 4.

| number | intermediate name | structural formula | raw materials |
|---|---|---|---|
| 5 | 4-chloro-1-methyl-6-morpholinopyrimidin-2(1H)-one | 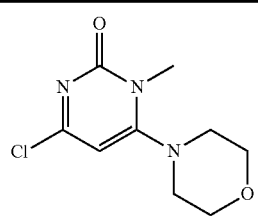 | intermediate 1, morpholine, phosphorus oxychloride |

-continued

| number | intermediate name | structural formula | raw materials |
|---|---|---|---|
| 6 | 4-chloro-1-ethyl-6-morpholinopyrimidin-2(1H)-one | | intermediate 2, morpholine, phosphorus oxychloride |
| 7 | 4-chloro-1-propyl-6-morpholinopyrimidin-2(1H)-one | | intermediate 3, morpholine, phosphorus oxychloride |
| 8 | 4-chloro-1-methyl-6-(piperidyl)pyrimidin-2(1H)-one | | intermediate 1, piperidine, phosphorus oxychloride |
| 9 | 4-chloro-1-methyl-6-thiomorpholinopyrimidin-2(1H)-one | | intermediate 1, thiomorpholine, phosphorus oxychloride |
| 10 | 4-chloro-6-(4-methoxypiperidyl)-1-methylpyrimidin-2(1H)-one | | intermediate 1, 4-methoxypiperidine, phosphorus oxychloride |
| 11 | 4-chloro-6-(cyclopropyl(methyl)amino)-1-methylpyrimidin-2(1H)-one | | intermediate 1, N-methylcyclopropylamine, phosphorus oxychloride |
| 12 | 4-chloro-6-(cyclopropyl(methyl)amino)-1-methylpyrimidin-2(1H)-one | | intermediate 1, dimethylamine, phosphorus oxychloride |

-continued

| number | intermediate name | structural formula | raw materials |
|---|---|---|---|
| 13 | 4-chloro-6-(diethylamino)-1-methylpyrimidin-2(1H)-one | | intermediate 1, diethylamine, phosphorus oxychloride |
| 14 | 4-chloro-1-methyl-6-(4-phenylpiperazinyl)pyrimidin-2(1H)-one | | intermediate 1, N-phenylpiperazine, phosphorus oxychloride |
| 15 | 4-chloro-1-methyl-6-(4-methylpiperidyl)pyrimidin-2(1H)-one | | intermediate 1, 4-methylpiperidine, phosphorus oxychloride |
| 16 | 4-chloro-1-methyl-6-(4-methylpiperazinyl)pyrimidin-2(1H)-one | | intermediate 1, N-methylpiperazine, phosphorus oxychloride |
| 17 | 4-chloro-6-(4-cyclopropylpiperazin-1-yl)-1-methylpyrimidin-2(1H)-one | | intermediate 1, N-cyclopropylpiperazine, phosphorus oxychloride |
| 18 | 4-chloro-6-(3,3-difluoropyrrolidinyl)-1-methylpyrimidin-2(1H)-one | | intermediate 1, 3,3-difluoropyrrolidine, phosphorus oxychloride |

| number | intermediate name | structural formula | raw materials |
|---|---|---|---|
| 19 | 4-chloro-6-(4,4-difluoropiperidin)-1-methylpyrimidin-2(1H)-one | | intermediate 1, 4,4-difluoropiperidine, phosphorus oxychloride |
| 20 | 4-chloro-6-((2-methoxyethyl)(methyl)amino)-1-methylpyrimidin-2(1H)-one | | intermediate 1, 2-methoxy-N-methylethyl-1-amine, phosphorus oxychloride |
| 21 | (S)-4-chloro-1-methyl-6-(3-methylmorpholino)pyrimidin-2(1H)-one | | intermediate 1, (S)-2-methylmorpholine, phosphorus oxychloride |
| 22 | 4-chloro-6-(4-fluoropiperid-1-yl)1-methylpyrimidin-2-2(1H)-one | | intermediate 1,4-fluoropiperidine, phosphorus oxychloride |

Intermediate 23—4-chloro-1-methyl-6-phenylpyrimidin-2(1H)-one

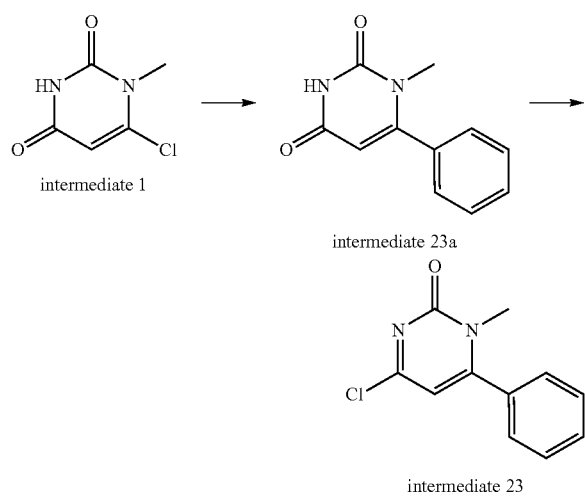

Intermediate 1 (300 mg, 1 eq.), phenylboronic acid (296 mg, 1.3 eq.), tetrakis(triphenylphosphine)palladium (108 mg, 0.05 eq.) and 2N aqueous sodium carbonate solution (654 ul, 3 eq.) were mixed in 5 ml of glycol dimethyl ether and reacted under microwave at 120° C. for 50 min. The mixture was cooled and evaporated to remove solvent. Water was added and the mixture was extracted with dichloromethane twice, rinsed with saturated brine once, dried over sodium sulfate, filtered, and evaporated to remove solvent to give 310 mg of intermediate 23a. MS (ESI) 203(M+H).

Intermediate (100 mg) was dissolved in phosphorus oxychloride (5 ml), stirred at 90° C. for 4 h, cooled, evaporated to remove phosphorus oxychloride, adjusted with 1N NaOH to neutral PH, extracted three times with dichloromethane, dried over sodium sulfate, and separated by column chromatography to give 90 mg of intermediate 23. MS (ESI): 221(M+H).

The following intermediates were prepared by referring to the preparation method of intermediate 23.

| number | intermediate name | structural formula | raw materials |
|---|---|---|---|
| 24 | 4-chloro-6-(4-methoxyphenyl)-1-methylpyrimidin-2(1H)-one | | intermediate 1,<br>p-methoxyphenylboronic acid,<br>tetrakis(triphenylphosphine)palladium,<br>2N aqueous sodium carbonate solution,<br>phosphorus oxychloride |
| 25 | 4-chloro-1-methyl-6-(1-methyl-1H-pyrazolyl-4)pyrimidin-2(1H)-one | | intermediate 1,<br>(1-methyl-1H-pyrazolyl-4)boronic acid,<br>tetrakis(triphenylphosphine)palladium,<br>2N aqueous sodium carbonate solution,<br>phosphorus oxychloride |
| 26 | 4-chloro-1-methyl-6-(thien-3-yl)pyrimidin-2(1H)-one | | intermediate 1,<br>thvenyl-3-boronic acid,<br>tetrakis(triphenylphosphine)palladium,<br>2N aqueous sodium carbonate solution,<br>phosphorous oxychloride |
| 27 | 4-chloro-1-methyl-6-(pyridine-4-yl)pyrimidin-2(1H)-one | | intermediate 1,<br>4-pyridineboronic acid,<br>tetrakis(triphenylphosphine)palladium,<br>2N aqueous sodium carbonate solution,<br>phosphorus oxychloride |
| 28 | 4-chloro-1-methyl-6-(pyridine-3-yl)pyrimidin-2(1H)-one | | intermediate 1,<br>3-pyridineboronic acid,<br>tetrakis(triphenylphosphine)palladium,<br>2N aqueous sodium carbonate solution,<br>phosphorus oxychloride |
| 29 | 6-chloro-3-methyl-[4,5'-dipyrimidin]-2(3H)-one | | intermediate 1,<br>pyrimidine-5-boronic acid,<br>tetakis(triphenylphosphine)paliadium,<br>2N aqueous sodium carbonate solution,<br>phosphorus oxychloride |
| 30 | 6-chloro-2'-methoxy-3-methyl-[4,5'-pyrimidin]-2(3H)-one | | intermediate 1,<br>(2-methoxy-5-yl)boronic acid,<br>tetrakis(triphenylphosphine)palladium,<br>2N aqueous sodium carbonate solution,<br>phosphorus oxychloride |

| number | intermediate name | structural formula | raw materials |
|---|---|---|---|
| 31 | 4-chloro-6-(4-fluorophenyl)-1-methylpyrimidin-2(1H)-one | | intermediate 1, p-fluorophenylboronic acid, tetakis(triphenylphosphine)palladium, 2N aqueous sodium carbonate solution, phosphorus oxychloride |
| 32 | 4-chloro-1-methyl-6-(4-(trifluoromethyl)phenyl)pyrimidin-2(1H)-one | | intermediate 1, p-trifluoromethylphenylbronic acid, tetrakis(triphenylphosphine)palladium, 2N aqueous sodium carbonate solution, phosphorus oxychloride |

Intermediate 33—1-(4-(4-chloro-3-(trifluoromethyl)phenoxy)phenyl)-N-methylmethylamine

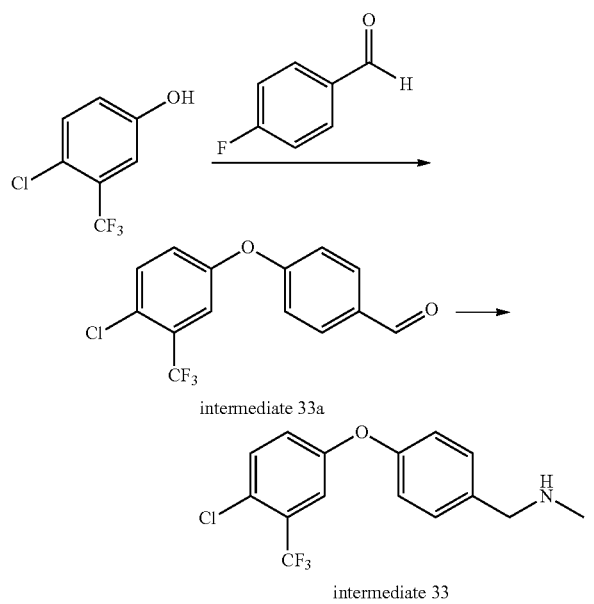

intermediate 33a intermediate 33

4-chloro-3-(trifluoromethyl)phenol (6.5 g, 1 eq.), p-fluorobenzaldehyde (3.9 ml, 1.1 eq.) and anhydrous potassium carbonate (6 g, 1.3 eq.) were dissolved in 30 ml of DMF, under nitrogen, and stirred at 120° C. for 2 h and cooled. Water was added and the mixture was extracted with ethyl acetate twice, rinsed three times with aqueous brine, dried over sodium sulfate, filtered, and evaporated to remove solvent to give 11 g of intermediate 33a. MS (ESI): 301(M+H).

Intermediate 33a (200 mg, 1 eq.) and methylamine alcohol solution (2 ml) were mixed in 4 ml of methanol and a certain amount of 4 A molecular sieve was added and placed at room temperature for 1 h. Sodium borohydride (24 mg, 1 eq.) was added and the reaction bottle was shaken and placed at room temperature for 1 h. The mixture was filtered, evaporated to dryness and aqueous ammonium chloride solution was added. The mixture was extracted three times with ethyl acetate, dried over anhydrous sodium sulfate, filtered and evaporated to dryness. The product was directly used in the next step. MS (ESI): 316(M+H).

Intermediate 34—(4-(4-chloro-3-(trifluoromethyl)phenoxy)phenyl)methanol

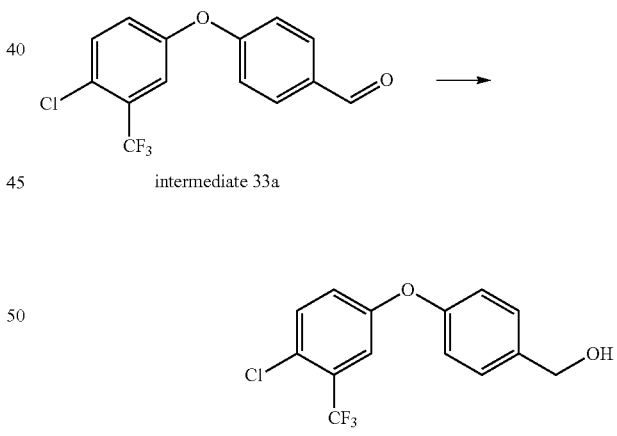

intermediate 33a intermediate 34

Intermediate 33a (4 g, 1 eq.) was dissolved in 50 ml of anhydrous ethanol, and sodium borohydride (493 mg, 1 eq.) was added under ice bath and then stirred at room temperature for 1 h. Aqueous ammonium chloride solution was added to quench the reaction, and evaporated to remove ethanol. Water was added and the mixture was extracted with ethyl acetate twice, rinsed with saturated brine once, dried over anhydrous sodium sulfate, and separated by column chromatography to give 4 g of intermediate 34. MS (ESI): 285(M-17).

Intermediate 35—(4-(4-chloro-3-(trifluoromethyl) phenoxy)phenyl)methylamine

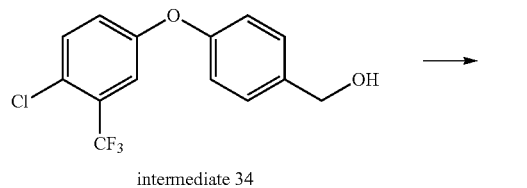

intermediate 34

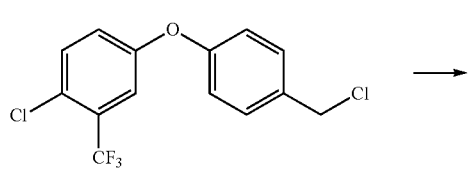

intermediate 35a

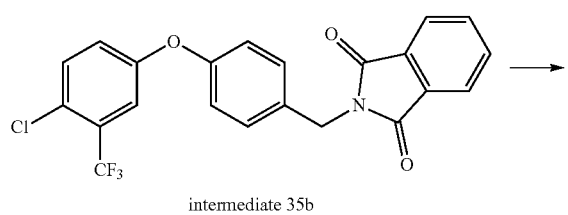

intermediate 35b

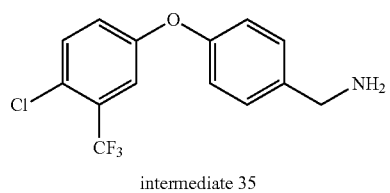

intermediate 35

Intermediate 34 (1 g, 1 eq.) was dissolved in re-distilled dichloromethane and dichlorosulfoxide (480 ul, 2 eq.) was added dropwise under ice bath. After the addition was complete, the mixture was stirred at room temperature for 2 h, then evaporated to remove solvent and dichlorosulfoxide to give 1.05 g of intermediate 35a which was directly used in the next step without purification.

Intermediate 35a (1 g, 1 eq.), phthalimide potassium salt (2.3 g, 2 eq.) and 18-crown-6 (165 mg, 0.1 eq.) were mixed in tetrahydrofuran, and the mixture was reacted under nitrogen at 65° C. overnight, then evaporated to remove solvent, added with water, extracted with dichloromethane three times, rinsed with saturated brine once, dried over anhydrous sodium sulfate, filtered, evaporated to dryness, and separated by column chromatography to give 1.63 g of intermediate 35b.

Intermediate 35b (1.63 g, 1 eq.) and hydrazine hydrate (4.5 ml, 80%, 20 eq.) were mixed in ethanol, stirred at room temperature for 1 h, evaporated to remove partial solvent, stirred at room temperature for a period of time, and filtered to remove solid. The filtrate was evaporated to dryness, and separated by column (aluminum oxide) chromatography to give 0.9 g of intermediate 35. MS (ESI): 302(M+H).

Intermediate 36—(4-(4-chloro-3-(trifluoromethyl) phenoxy)phenyl)methanthiol

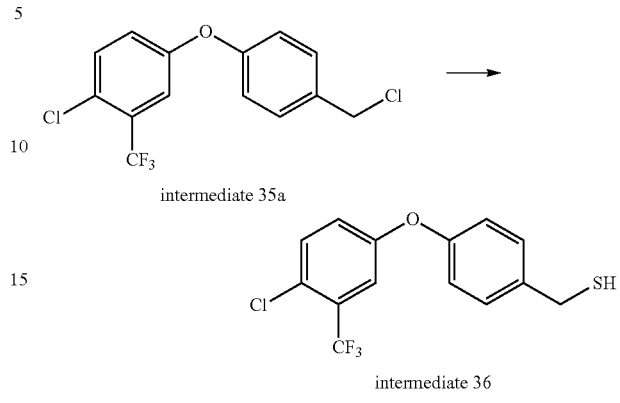

intermediate 35a intermediate 36

Intermediate 35a (210 mg, 1 eq.) and thiourea (70 mg, 1.4 eq.) were mixed in 2 ml of anhydrous ethanol, refluxed for 4 h, and cooled to room temperature. 10 N aqueous sodium hydroxide solution (2 ml) was added, refluxed for 3 h, and cooled to room temperature. 4N aqueous hydrochloric acid solution was added to adjust pH to 5, extracted with ethyl acetate three times, rinsed with saturated brine once, dried over anhydrous sodium sulfate, filtered, and evaporated to dryness. The product was directly used in the next step without purification. MS (ESI): 285(M-33).

Intermediate 37—(4-(4-chloro-3-(trifluoromethyl) phenoxy)-3,5-difluorophenyl)methanol

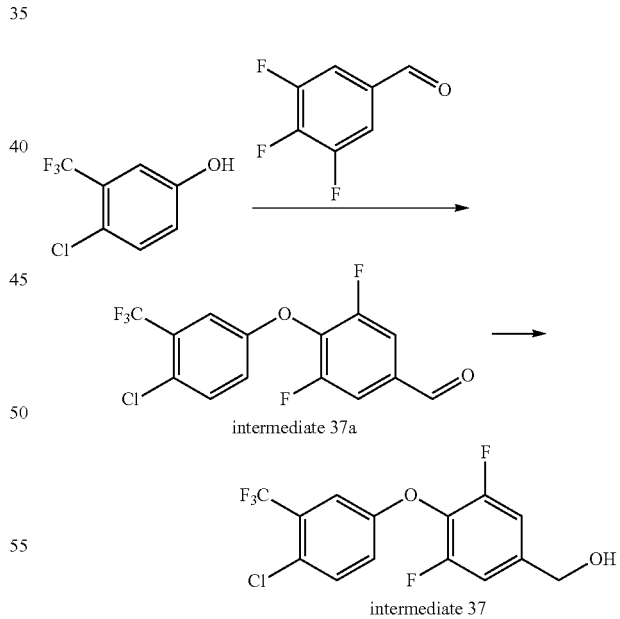

intermediate 37a intermediate 37

4-chloro-3-(trifluoromethyl)phenol (4.67 g, 1 eq.), 3,4,5-trifluorobenzaldehyde (4 g, 1.05 eq.) and anhydrous potassium carbonate (4.27 g, 1.3 eq.) were dissolved in DMF, under nitrogen, stirred at 120° C. for 2 h, cooled, added with water, extracted with ethyl acetate twice, rinsed with aqueous brine three times, dried over sodium sulfate, filtered, and evaporated to remove solvent to give 8 g of intermediate 37a. MS (ESI): 337(M+H).

Intermediate 37a (4 g, 1 eq.) was dissolved in 50 ml of anhydrous ethanol, under ice bath added with sodium borohydride (440 mg, 1 eq.), then stirred at room temperature for 1 h. Aqueous ammonium chloride solution was added to quench the reaction, and the mixture was evaporated to remove ethanol, added with water, extracted with ethyl acetate twice, rinsed with saturated brine once, dried over anhydrous sodium sulfate, and separated by column chromatography to give 4 g of intermediate 37. MS (ESI): 321(M-17).

Intermediate 38—2-(4-(4-chloro-3-(trifluoromethyl) phenoxy)-3,5-difluorophenyl)ethan-1-ol

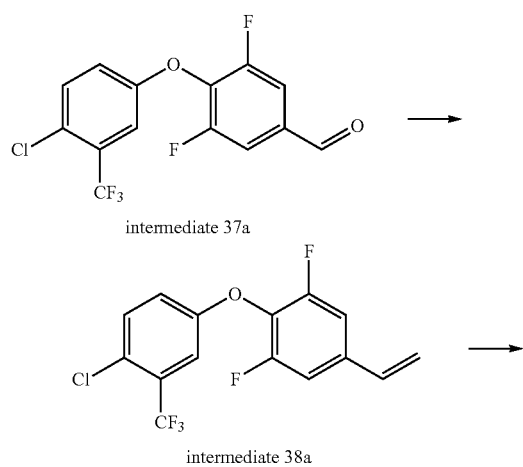

intermediate 37a intermediate 38a

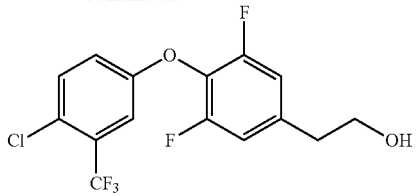

intermediate 38

Sodium hydride (950 mg, 4 eq.) was placed in a flask, under ice bath, added with ultra dry tetrahydrofuran and methyltriphenylphosphonium bromide (2.54 g, 1.2 eq.) sequentially, and stirred under ice bath for 1 h. Then intermediate 35a (2 g, 1 eq.) was added, and stirred at room temperature for 2 h. After the reaction was complete, the mixture was directly mixed and separated by column chromatography to give 730 mg of intermediate 38a.

Intermediate 38a (730 mg, 1 eq.) was dissolved in ultra dry tetrahydrofuran, under nitrogen and ice bath, 1N borane tetrahydrofuran solution (2.2 ml, 1.2 eq.) was added, and stirred at room temperature for 1 h. Then under ice bath 2 ml of methanol was slowly added dropwise to quench excessive borane and sodium hydroxide (350 mg, 4 eq.) was added in batches followed by the addition of hydrogen peroxide (3.1 ml, 30% aqueous solution, 14 eq.). After the addition, the reaction was carried out at 60° C. for 2 h and sodium sulfite aqueous solution was added to quench the reaction. The mixture was extracted with ethyl acetate three times, rinsed with saturated brine once, dried over anhydrous sodium sulfate, filtered, evaporated to dryness, and separated by column chromatography to give 600 g of intermediate 38. 348(M-17).

The following intermediates were prepared by referring to the preparation method of intermediate 37.

| number | intermediate name | structural formula | raw materials |
|---|---|---|---|
| 39 | (4-(4-chloro-3-(trifluoromethyl)phenoxy)-3-fluorophenyl)methanol | | 4-chloro-3-(trifluoromethyl) phenol, 4,5-difluorobenzaldehyde, sodium borohydride |
| 40 | 2-(4-chloro-3-(trifluoromethyl)phenoxy)-4-(hydroxymethyl)benzonitrile | | 4-chloro-3-(trifluoromethyl) phenol, 2-fluoro-5-cyanobenzaldehyde, sodium borohydride |
| 41 | (3,5-difluoro-4-(6-(trifluoromethyl)pyridinyl-3-oxy)phenyl)methanol | | 6-(trifluoromethyl) pyridin-3-ol, 3,4,5-trifluorobenzaldehyde, sodium borohydride |
| 42 | (3,4,5-trifluorophenyl)methanol | | 3,4,5-trifluorobenzaldehyde, sodium borohydride |

-continued

| number | intermediate name | structural formula | raw materials |
|---|---|---|---|
| 43 | (3,5-difluoro-4-(2-(trifluoromethyl)pyridinyl-4-oxy)phenyl)methanol | | 2-(trifluoromethyl) pyridin-4-ol, 2,4,5-trifluorobenzaldehyde, sodium borohydride |
| 44 | (4-(6-chloropyridinyl-3-oxy)-3,5-difluorophenyl)methanol | | 6-chloropyridin-3-ol, 3,4,5-trifluorobenzaldehyde, sodium borohydride |
| 45 | (3-chloro-4-(4-chloro-3-(trifluoromethyl)phenoxy)phenyl)methanol | | 4-chloro-3-(trifluoromethyl)phenol, 3-chloro-4-fluorobenzaldehyde, sodium borohydride |
| 46 | (4-(4-chloro-3-(trifluoromethyl)phenoxy)-3-methylphenyl)methanol | | 4-chloro-3-(trifluoromethyl)phenol, 4-fluoro-3-methylbenzaldehyde, sodium borohydride |
| 47 | (3,5-difluoro-4-(4-fluoro-3-(trifluoromethyl)phenoxy)phenyl)methanol | | 4-fluoro-3-(trifluoromethyl)phenol, 3,4,5-trifluorobenzaldehyde, sodium borohydride |
| 48 | (3-fluoro-4-((2-(trifluoromethyl)pyridin-4-yl)oxy)phenyl)methanol | | 2-(trifluoromethyl)pyridin-4-ol, 3,4-difluorobenzaldehyde, sodium borohydride |
| 49 | 5-(hydroxymethyl)-2-((5-(trifluoromethyl)pyridin-3-yl)oxy)benzonitrile | | 5-(trifluoromethyl) pyridin-3-ol, 2-fluoro-5-cyanobenzaldehyde, sodium borohydride |
| 50 | (3,5-difluoro-4-((5-(trifluoromethyl)pyridin-3-yl)oxy)phenyl)methanol | | 5-trifluoromethyl) pyridin-3-ol, 3,4,5-trifluorobenzaldehyde, sodium borohydride |
| 51 | 4-(2,6-difluoro-4-(hydroxymethyl)phenoxy)-2-(trifluoromethyl)benzonitrile | | 4-hydroxyl-2-(trifluoromethyl)benzonitrile, 3,4,5-trifluorobenzaldehyde, sodium borohydride |

-continued

| number | intermediate name | structural formula | raw materials |
|---|---|---|---|
| 52 | 4-(2-fluoro-4-(hydroxymethyl)phenoxy)-2-(trifluoromethyl)benzonitrile | | 4-hydroxy-2-(trifluoromethyl)benzonitrile, 3,4-difluorobenzaldehyde, sodium borohydride |
| 53 | 4-(2-cyano-4-(hydroxymethyl)phenoxy)-2-(trifluoromethyl)benzonitrile | | 4-hydroxyl-2-(trifluoromethyl)benzonitrile, 2-fluoro-5-cyanobenzaldehyde, sodium borohydride |
| 54 | 2-(4-fluoro-3-(trifluoromethyl)phenoxy)-5-(hydroxymethyl)benzonitrile | | 4-fluoro-3-(trifluoromethyl)phenol, 2-fluoro-5-cyanobenzaldehyde, sodium borohydride |
| 55 | 5-(hydroxymethyl)-2-((6-(trifluoromethyl)pyridin-3-yl)oxy)benzonitrile | | 6-(trifluoromethyl)pyridin-3-ol, 2-fluoro-5-cyanobenzaldehyde, sodium borohydride |

Intermediate 56—4-((4-(4-chloro-3-(trifluoromethyl)phenoxy)-3,5-difluorobenzyl)oxy)-6-methoxypyrimidin-2(1H)-one

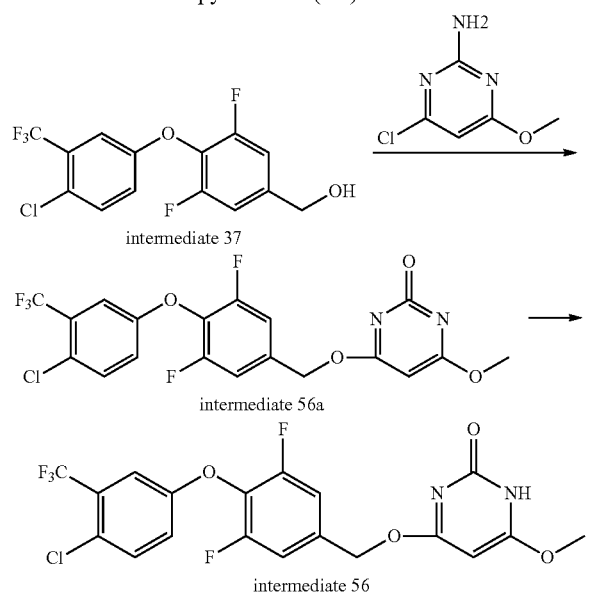

Intermediate 37 (1.1 g, 1.1 eq.) was dissolved in tetrahydrofuran, and under ice bath added with sodium hydride (352 mg, 60%, 3 eq.). The mixture was stirred under ice bath for 30 min, added with 4-chloro-6-methoxypyrimidine-2-amine (467 mg, 1 eq.), then reacted at 70° C. overnight. After the reaction was complete, under ice bath aqueous ammonium chloride solution was added to quench the reaction. The mixture was extracted with ethyl acetate three times, dried over anhydrous sodium sulfate, filtered, evaporated to dryness, and separated by column chromatography to give 440 mg of intermediate 56a as white solid. MS (ESI): 462(M+H).

Intermediate 56a (200 mg, 1 eq.) was dissolved in glacial acetic acid, and sodium nitrite (60 mg, 2 eq.) was added in batches and reacted at room temperature overnight. After completion of the reaction, the solvent was distilled off. Dichloromethane was added and the mixture was washed twice with aqueous sodium bicarbonate, dried over anhydrous sodium sulfate, filtered, evaporated to dryness, and 150 mg of product was separated by column chromatography. MS (ESI): 463(M+H).

The following intermediates were prepared by referring to the preparation method of intermediate 56.

| number | intermediate name | structure formula | raw materials |
|---|---|---|---|
| 57 | 4-((4-(4-chloro-3-(trifluoromethyl)phenoxy)benzyl)oxy)-6-methoxypyrimidin-2(1H)-one | | intermediate 34, 4-chloro-6-methoxypyrimidine-2-amine, sodium hydride, sodium nitrite, glacial acetic acid |

| number | intermediate name | structure formula | raw materials |
|---|---|---|---|
| 58 | 4-((4-(4-chloro-3-(trifluoromethyl)phenoxy)-3-fluorobenzyl)oxy)-6-methoxypyrimidin-2(1H)-one | 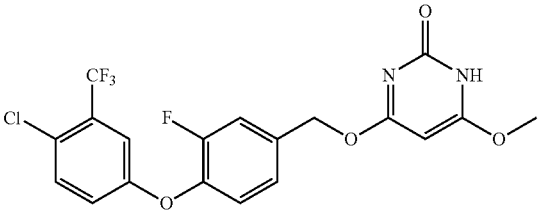 [SMILES: COc1cc(OCc2ccc(Oc3ccc(Cl)c(C(F)(F)F)c3)c(F)c2)nc(=O)[nH]1] | intermediate 39, 4-chloro-6-methoxypryimidine-2-amine, sodium hydride, sodium nitrite, glacial acetic acid |
| 59 | 2-(4-chloro-3-(trifluoromethyl)phenoxy)-5-(((6-methoxy-2-oxo-1,2-dihydropyrimidin-4-yl)oxy)methyl)benzonitrile | 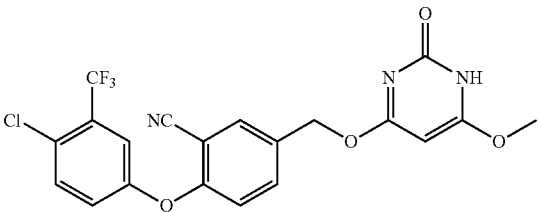 [SMILES: COc1cc(OCc2ccc(Oc3ccc(Cl)c(C(F)(F)F)c3)c(C#N)c2)nc(=O)[nH]1] | intermediate 40, 4-chloro-6-methoxypryimidine-2-amine, sodium hydride, sodium nitrite, glacial acetic acid |
| 60 | 4-((3-fluoro-4-((2-(trifluoromethyl)pyridin-4-yl)oxy)benzyl)oxy)-6-methoxypryimidin-2(1H)-one | 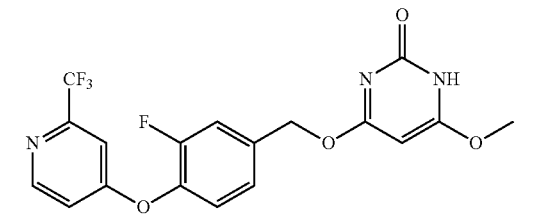 [SMILES: COc1cc(OCc2ccc(Oc3ccnc(C(F)(F)F)c3)c(F)c2)nc(=O)[nH]1] | intermediate 48, 4-chloro-6-methoxypryimidine-2-amine, sodium hydride, sodium nitrite, glacial acetic acid |
| 61 | 4-((3,5-difluoro-4-((2-(trifluoromethyl)pyridin-4-yl)oxy)benzyl)oxy)-6-methoxypyridin-2(1H)-one | 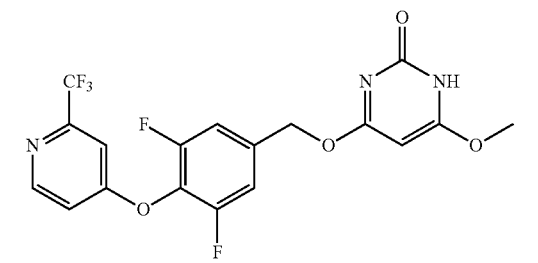 [SMILES: COc1cc(OCc2cc(F)c(Oc3ccnc(C(F)(F)F)c3)c(F)c2)nc(=O)[nH]1] | intermediate 43, 4-chloro-6-methoxypryimidine-2-amine, sodium hydride, sodium nitrite, glacial acetic acid |
| 62 | 4-((3,5-difluoro-4-((6-(trifluoromethyl)pyridin-3-yl)oxy)benzyl)oxy)-6-methoxypyrimidin-2(1H)-one | 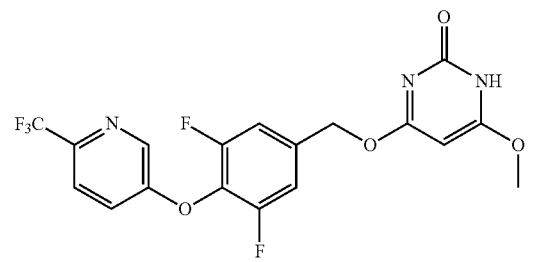 [SMILES: COc1cc(OCc2cc(F)c(Oc3ccc(C(F)(F)F)nc3)c(F)c2)nc(=O)[nH]1] | intermediate 41, 4-chloro-6-methoxypryimidine-2-amine, sodium hydride, sodium nitrite, glacial acetic acid |
| 63 | 5-(((6-methoxy-2-oxo-1,2-dihydropyrimidin-4-yl)oxy)methyl)-2-((5-(trifluoromethyl)pyridin-3-yl)oxy)benzonitrile | 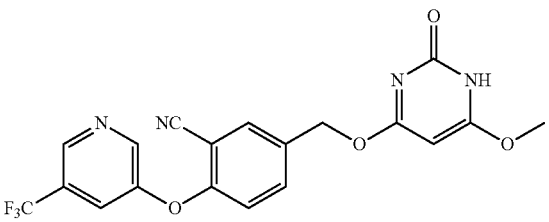 | intermediate 49, 4-chloro-6-methoxypryimidine-2-amine, sodium hydride, sodium nitrite, glacial acetic acid |

-continued

| number | intermediate name | structure formula | raw materials |
|---|---|---|---|
| 64 | 4-((3,5-difluoro-4-((5-(trifluoromethyl)pyridin-3-yl)oxy)benzyl)oxy)-6-methoxypyrimidin-2(1H)-one | | intermediate 50, 4-chloro-6-methoxypryimidine-2-amine, sodium hydride, sodium nitrite, glacial acetic acid |
| 65 | 4-(2,6-difluoro-4-(((6-methoxy-2-oxo-1,2-dihydropyrimidin-4-yl)oxy)methyl)phenoxy)-2-(trifluoromethyl)benzonitrile | | intermediate 51, 4-chloro-6-methoxypryimidine-2-amine, sodium hydride, sodium nitrite, glacial acetic acid |
| 66 | 4-(2-fluoro-4-(((6-methoxy-2-oxo-1,2-dihydropyrimidin-4-yl)oxy)methyl)phenoxy)-2-(trifluoromethyl)benzonitrile | | intermediate 52, 4-chloro-6-methoxypryimidine-2-amine, sodium hydride, sodium nitrite, glacial acetic acid |
| 67 | 4-(2-cyano-4-(((6-methoxy-2-oxo-1,2-dihydropyrimidin-4-yl)oxy)methyl)phenoxy)-2-(trifluoromethyl)benzonitrile | | intermediate 53, 4-chloro-6-methoxypryimidine-2-amine, sodium hydride, sodium nitrite, glacial acetic acid |
| 68 | 2-(4-fluoro-3-(trifluoromethyl)phenoxy)-5-(((6-methoxy-2-oxo-1,2,-dihydropyrimidin-4-yl)oxy)methyl)benzonitrile | | intermediate 54, 4-chloro-6-methoxypryimidine-2-amine, sodium hydride, sodium nitrite, glacial acetic acid |

Intermediate 69—1-methyl-1H-pyrazole-4-carbaldehyde

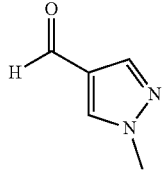

N-methylpyrazole (1.0 g, 1 eq.) was dissolved in N,N-dimethylformamide (2.8 ml, 3 eq.), phosphorus oxychloride (1.3 ml, 1.2 eq.) was added dropwise at 90° C. over about 1 h. The mixture was reacted for another 2 h and then cooled. The reaction liquid was poured into iced water and adjusted with 10% aqueous sodium hydroxide solution to pH 4~5, extracted four times with dichloromethane, rinsed with water twice, and separated by column chromatography to give 600 mg product.

Intermediate 70—(1-methyl-1H-pyrazol-4-yl)methanol

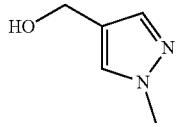

Intermediate 69 (600 mg, 1 eq.) was dissolved in tetrahydrofuran, and lithium aluminum hydride (210 mg, 1 eq.) was added under ice bath and the mixture was reacted at room temperature for 2 h. After completion of the reaction, 210 µl of water, 210 µl of 10% aqueous sodium hydroxide solution, and 630 µl of water were successively added, followed by addition of anhydrous magnesium sulfate. The mixture was stirred for a while, filtered and evaporated to dryness to give 400 mg of an oil. MS (ESI): 113(M+H).

Intermediate 71—4-(chloromethyl)-1-methyl-1H-pyrazole

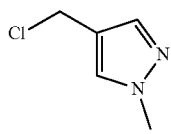

Intermediate 70 (160 mg, 1 eq.) was dissolved in redistilled dichloromethane, and dichlorosulfoxide (310 µl, 3 eq.) was added under ice bath. The mixture was reacted for 1 h, evaporated to remove solvent. The product was directly used in the next step without purification.

Intermediate 72—4-((4-(4-chloro-3-(trifluoromethyl)phenoxy)-3,5-difluorobenzyl)oxy)-6-methyl-pyrimidine-2-amine

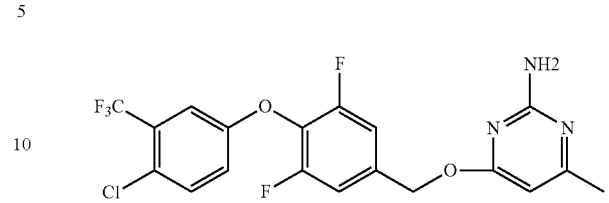

Intermediate 37 (1.1 g, 1.1 eq.) was dissolved in tetrahydrofuran, and sodium hydride (352 mg, 60%, 3 eq.) was added under ice bath. The mixture was stirred under ice bath for 30 min, 4-chloro-6-methylpyrimidine-2-amine (420 mg, 1 eq.) was added and then the mixture was reacted at room temperature overnight. After completion of the reaction, under ice bath aqueous ammonium chloride solution was added to quench the reaction. The mixture was extracted with ethyl acetate three times, dried over anhydrous sodium sulfate, filtered, evaporated to dryness, and separated by column chromatography to give 440 mg of white solid. MS (ESI): 446(M+H).

Intermediate 73—4-((4-(4-chloro-3-(trifluoromethyl)phenoxy)-3,5-difluorobenzyl)oxy)-6-methyl-pyrimidin-2(1H)-one

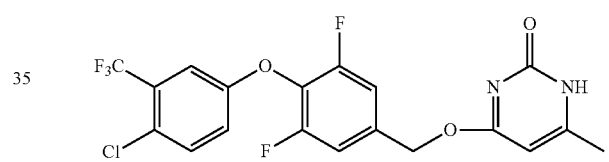

Intermediate 72 (200 mg, 1 eq.) was dissolved in glacial acetic acid, sodium nitrite (62 mg, 2 eq.) was added in batches, and the mixture was reacted at room temperature overnight. After completion of the reaction, the mixture was evaporated to remove solvent, dichloromethane was added and the mixture was rinsed with aqueous sodium bicarbonate solution twice, dried over anhydrous sodium sulfate, filtered, evaporated to dryness, and separated by column chromatography to give 150 mg produce. MS (ESI): 447 (M+H).

Intermediate 74—4-((4-(4-chloro-3-(trifluoromethyl)phenoxy)-3-fluorobenzyl)oxy)-6-methylpyrimidine-2-amine

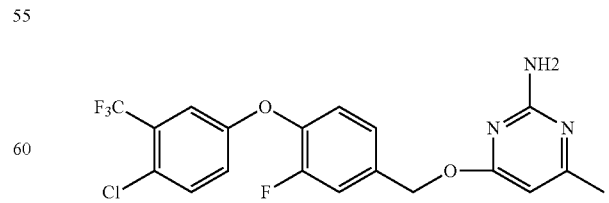

Intermediate 39 and 4-chloro-6-methoxypyrimidine-2-amine were used as raw materials. Reference was made to the preparation method of Intermediate 72. MS (ESI): 428 (M+H).

Intermediate 75—4-((4-(4-chloro-3-(trifluoromethyl)phenoxy)-3,5-difluorobenzyl)oxy)-6-methylpyrimidin-2(1H)-one

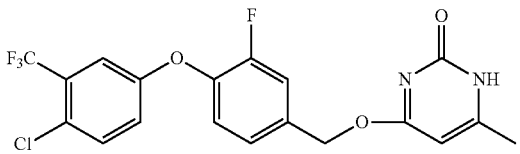 [SMILES: Cc1cc(OCc2ccc(Oc3ccc(Cl)c(C(F)(F)F)c3)c(F)c2)nc(=O)[nH]1]

Starting from intermediate 74 as a starting material, Reference was made to the preparation method of intermediate 73. MS (ESI): 429 (M+H).

Example 1

4-(4-(4-chloro-3-(trifluoromethyl)phenoxy)-3,5-difluorobenzyl)oxy)-1-methyl-6-(pyrrolidinyl)pyrimidin-2(1H)-one

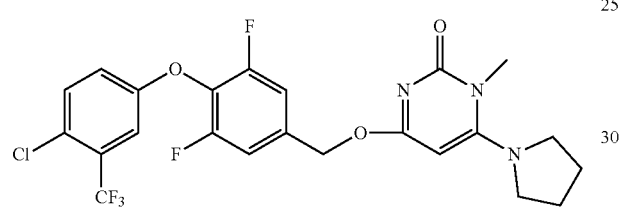

Intermediate 4 (19 mg, 1 eq.), intermediate 37 (30 mg, 1 eq.) and sodium hydride (11 mg, 3 eq.) were mixed in 2 ml of N,N-dimethylformamide, stirred at room temperature for 30 min, added with water to quench the reaction. The mixture was extracted three times with ethyl acetate, rinsed three times with saturated brine, dried over anhydrous sodium sulfate, separated by column chromatography to give 20 mg target product. $^1$H NMR (400 MHz, Chloroform-d) δ 7.43 (d, J=8.8 Hz, 1H), 7.32 (d, J=3.0 Hz, 1H), 7.15-7.08 (m, 2H), 7.03 (dd, J=8.8, 2.9 Hz, 1H), 5.42 (s, 2H), 5.35 (s, 1H), 3.51 (s, 3H), 3.41-3.34 (m, 4H), 2.07-1.98 (m, 4H). MS (ESI): 516 (M+H).

Example 2

4-((4-(4-chloro-3-(trifluoromethyl)phenoxy)benzyl)(methyl)amino)-1-methyl-6-morpholinopyrimidin-2(1H)-one

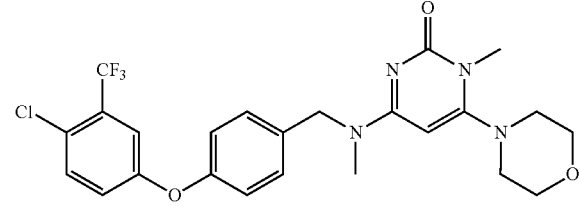 [SMILES: CN(Cc1ccc(Oc2ccc(Cl)c(C(F)(F)F)c2)cc1)c1cc(N2CCOCC2)n(C)c(=O)n1]

Intermediate 5 (25 mg, 1 eq.), intermediate 33 (34 mg, 1 eq.) and triethylamine (18 ul, 1.2 eq.) were mixed in N,N-dimethylformamide. The mixture was reacted at room temperature overnight, then added with water to quench the reaction. The mixture was extracted with ethyl acetate three times, rinsed with saturated brine twice, dried over anhydrous sodium sulfate, filtered, evaporated to remove solvent, and separated by column chromatography to give 18 mg of white solid. $^1$H NMR (400 MHz, Chloroform-d) δ 7.45 (d, J=8.8 Hz, 1H), 7.32 (d, J=2.9 Hz, 1H), 7.27 (d, J=8.3 Hz, 2H), 7.08 (dd, J=8.6, 2.6 Hz, 1H), 6.98 (d, J=8.3 Hz, 2H), 5.27 (s, 1H), 4.89 (s, 2H), 3.86 (s, 4H), 3.46 (s, 3H), 2.99 (s, 4H). MS (ESI): 509 (M+H).

Example 3

4-((4-(4-chloro-3-(trifluoromethyl)phenoxy)benzyl)amino)-1-methyl-6-morpholinopyrimidin-2(1H)-one

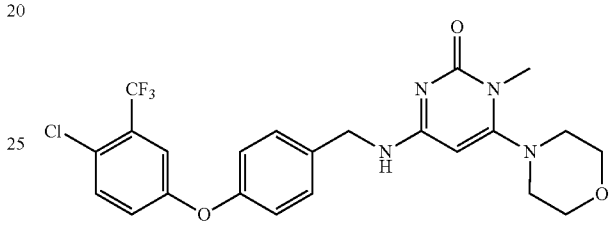

Intermediate 5 and intermediate 35 were used as raw materials. Reference was made to the preparation method of Example 2. $^1$H NMR (400 MHz, Chloroform-d) δ 7.45 (d, J=8.8 Hz, 1H), 7.36 (d, J=8.5 Hz, 2H), 7.32 (d, J=2.8 Hz, 1H), 7.08 (dd, J=8.7, 2.9 Hz, 1H), 7.00 (d, J=8.5 Hz, 2H), 5.12 (s, 1H), 4.67 (s, 2H), 3.88-3.81 (m, 4H), 3.44 (s, 3H), 3.01-2.92 (m, 4H). MS (ESI): 495 (M+H).

Example 4

4-((4-(4-chloro-3-(trifluoromethyl)phenoxy)benzyl)mercapto)-1-methyl-6-morpholinopyrimidin-2(1H)-one

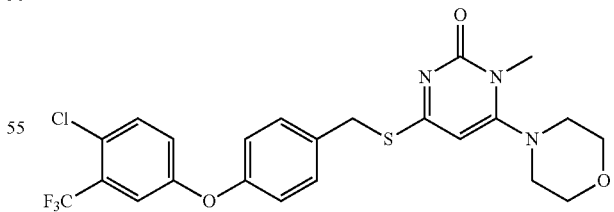

Intermediate 5 and intermediate 36 were used as raw materials. Reference was made to the preparation method of Example 1. $^1$H NMR (400 MHz, Chloroform-d) δ 7.44-7.38 (m, 3H), 7.31 (d, J=2.6 Hz, 1H), 7.05 (dd, J=8.8, 2.3 Hz, 1H), 6.93 (d, J=8.3 Hz, 2H), 5.74 (s, 1H), 4.47 (s, 2H), 3.87-3.81 (m, 4H), 3.48 (s, 3H), 3.05-2.98 (m, 4H). MS (ESI): 512 (M+H).

Example 5

4-(4-(4-chloro-3-(trifluoromethyl)phenoxy)-3,5-difluorophenethyloxy)-1-methyl-6-morpholinopyrimidin-2(1H)-one

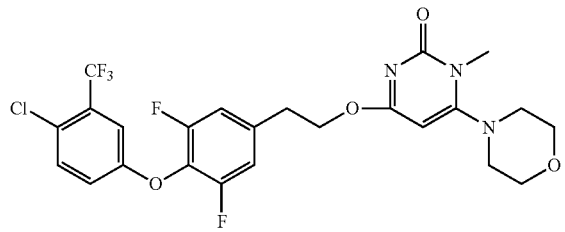 [SMILES: Cn1c(N2CCOCC2)cc(OCCc2cc(F)c(Oc3ccc(Cl)c(C(F)(F)F)c3)c(F)c2)nc1=O]

Intermediate 5 and intermediate 38 were used as raw materials. Reference was made to the preparation method of Example 1. $^1$H NMR (400 MHz, Chloroform-d) δ 7.44 (d, J=8.7 Hz, 1H), 7.30 (d, J=3.1 Hz, 1H), 7.03 (dd, J=8.8, 2.8 Hz, 1H), 6.99-6.93 (m, 2H), 5.40 (s, 1H), 4.62 (t, J=6.4 Hz, 2H), 3.90-3.85 (m, 4H), 3.49 (s, 3H), 3.07 (t, J=6.4 Hz, 2H), 3.05-3.01 (m, 4H), MS (ESI): 546 (M+H).

Example 6

4-(4-(4-chloro-3-(trifluoromethyl)phenoxy-3,5-difluorobenzyl)oxy)-1-methyl-6-morpholinopyrimidin-2(1H)-one

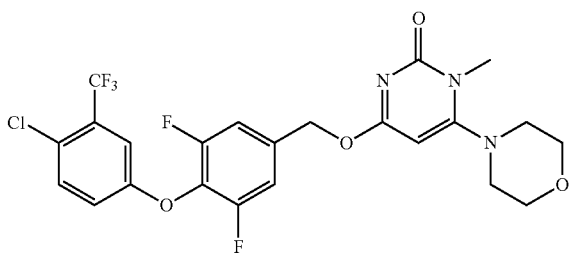 [SMILES: Cn1c(N2CCOCC2)cc(OCc2cc(F)c(Oc3ccc(Cl)c(C(F)(F)F)c3)c(F)c2)nc1=O]

Intermediate 5 and intermediate 37 were used as raw materials.
Reference was made to the preparation method of Example 1. $^1$H NMR (400 MHz, Chloroform-d) δ 7.44 (d, J=8.8 Hz, 1H), 7.32 (d, J=3.0 Hz, 1H), 7.16-7.09 (m, 2H), 7.04 (dd, J=8.8, 3.0 Hz, 1H), 5.50 (s, 1H), 5.43 (s, 2H), 3.91-3.85 (m, 4H), 3.51 (s, 3H), 3.08-3.03 (m, 4H). MS (ESI): 532 (M+H).

Example 7

4-(4-(4-chloro-3-(trifluoromethyl)phenoxy)-3,5-difluorobenzyl)oxy)-1-methyl-6-(piperidyl)pyrimidin-2(1H)-one

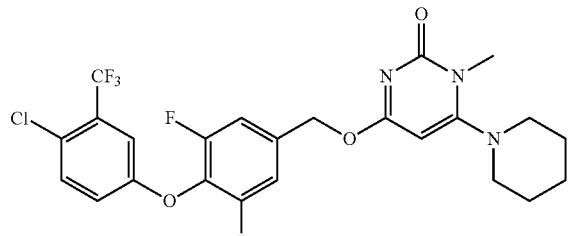

Intermediate 8 and intermediate 37 were used as raw materials. Reference was made to the preparation method of Example 1. $^1$H NMR (400 MHz, Chloroform-d) δ 7.43 (d, J=8.8 Hz, 1H), 7.32 (d, J=2.9 Hz, 1H), 7.15-7.08 (m, 2H), 7.03 (dd, J=8.8, 2.9 Hz, 1H), 5.47 (s, 1H), 5.42 (s, 2H), 3.47 (s, 3H), 3.03-2.94 (m, 4H), 1.80-1.72 (m, 4H), 1.71-1.65 (m, 2H). MS (ESI): 530 (M+H).

Example 8

4-(4-(4-chloro-3-(trifluoromethyl)phenoxy)-3,5-difluorobenzyl)oxy)-1-methyl-6-thiomorpholinopyrimidin-2(1H)-one

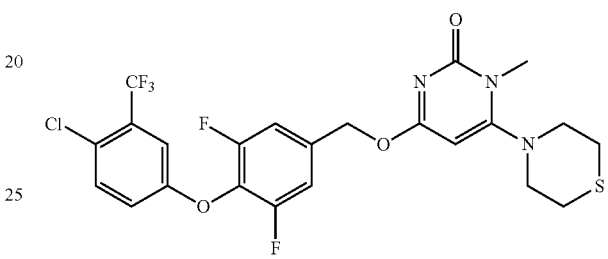

Intermediate 9 and intermediate 37 were used as raw materials. Reference was made to the preparation method of Example 1. $^1$H NMR (400 MHz, Chloroform-d) δ 7.44 (d, J=8.8 Hz, 1H), 7.31 (d, J=2.8 Hz, 1H), 7.12 (d, J=8.1 Hz, 2H), 7.03 (dd, J=8.8, 2.8 Hz, 1H), 5.50 (s, 1H), 5.42 (s, 2H), 3.47 (s, 3H), 3.35-324 (m, 4H), 2.88-2.77 (m, 4H). MS (ESI): 548 (M+H).

Example 9

4-(4-(4-chloro-3-(trifluoromethyl)phenoxy)-3,5-difluorobenzyl)oxy)-6-(4-methoxypiperidyl)-1-methylpyrimidin-2(1H)-one

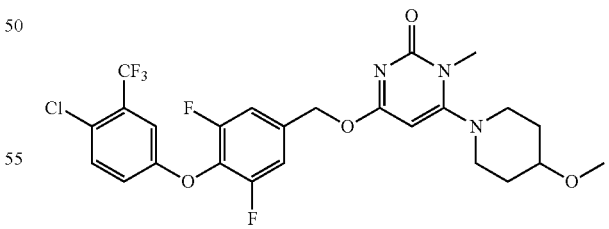

Intermediate 10 and intermediate 37 were used as raw materials. Reference was made to the preparation method of Example 1. $^1$H NMR (400 MHz, Chloroform-d) δ 7.44 (d, J=8.8 Hz, 1H), 7.32 (d, J=3.0 Hz, 1H), 7.12 (d, J=8.1 Hz, 2H), 7.03 (dd, J=8.8, 3.0 Hz, 1H), 5.49 (s, 1H), 5.42 (s, 2H), 3.50-3.48 (m, 1H), 3.48 (s, 3H), 3.40 (s, 3H), 3.28-3.17 (m, 2H), 2.93-2.85 (m, J=8.3, 2H), 2.06-1.96 (m, 2H), 1.87-1.76 (m, 1H). MS (ESI): 560 (M+H).

Example 10

4-(4-(4-chloro-3-(trifluoromethyl)phenoxy)-3,5-difluorobenzyl)oxy)-6-(cyclopropyl(methyl)amino)-1-methylpyrimidin-2(1H)-one

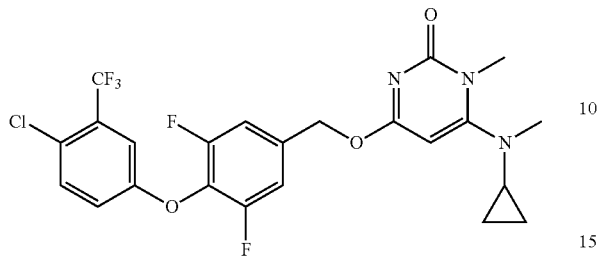

Intermediate 11 and intermediate 37 were used as raw materials. Reference was made to the preparation method of Example 1. $^1$H NMR (300 MHz, Chloroform-d) δ 7.41 (d, J=8.8 Hz, 1H), 7.29 (d, J=2.9 Hz, 1H), 7.10 (d, J=8.2 Hz, 2H), 7.01 (dd, J=8.8, 2.9 Hz, 1H), 5.60 (s, 1H), 5.39 (s, 2H), 3.41 (s, 3H), 2.88 (s, 3H), 2.54 (tt, J=6.7, 3.7 Hz, 1H), 0.85-0.79 (m, 2H), 0.60-0.52 (m, 2H). MS (ESI): 516 (M+H).

Example 11

4-(4-(4-chloro-3-(trifluoromethyl)phenoxy)-3,5-difluorobenzyl)oxy)-6-(dimethylamino)-1-methylpyrimidin-2(1H)-one

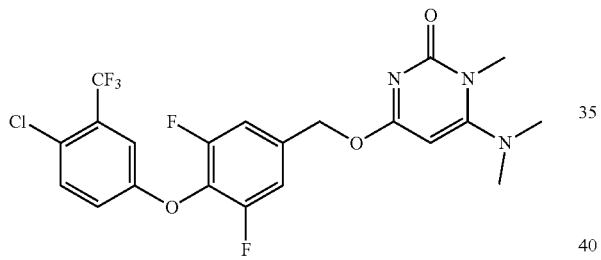

Intermediate 12 and intermediate 37 were used as raw materials. Reference was made to the preparation method of Example 1. $^1$H NMR (400 MHz, Chloroform-d) δ 7.44 (d, J=8.8 Hz, 1H), 7.32 (d, J=3.0 Hz, 1H), 7.15-7.09 (m, 2H), 7.03 (dd, J=8.8, 3.0 Hz, 1H), 5.45 (s, 1H), 5.42 (s, 2H), 3.49 (s, 3H), 2.85 (s, 6H). MS (ESI): 490 (M+H).

Example 12

4-(4-(4-chloro-3-(trifluoromethyl)phenoxy)-3,5-difluorobenzyl)oxy)-6-(diethylamino)-1-methylpyrimidin-2(1H)-one

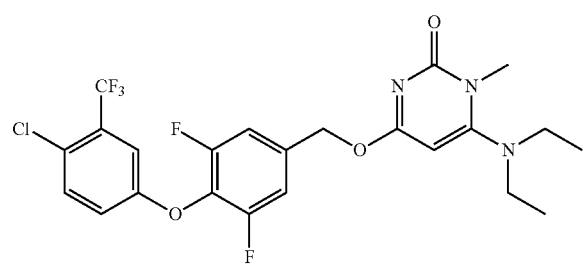 [SMILES: CCN(CC)c1cc(OCc2cc(F)c(Oc3ccc(Cl)c(C(F)(F)F)c3)c(F)c2)nc(=O)n1C]

Intermediate 13 and intermediate 37 were used as raw materials. Reference was made to the preparation method of Example 1. $^1$H NMR (300 MHz, Chloroform-d) δ 7.41 (d, J=8.8 Hz, 1H), 7.29 (d, J=2.9 Hz, 1H), 7.10 (d, J=8.2 Hz, 2H), 7.01 (dd, J=8.8, 2.9 Hz, 1H), 5.49 (s, 1H), 5.39 (s, 2H), 3.45 (s, 3H), 3.11 (q, J=7.0 Hz, 4H), 1.14 (t, J=7.0 Hz, 6H). MS (ESI): 518 (M+H).

Example 13

1-methyl-6-(4-phenylpiperazinyl)-4-(3,4,5-trifluorobenzyl)oxy)pyrimidin-2(1H)-one

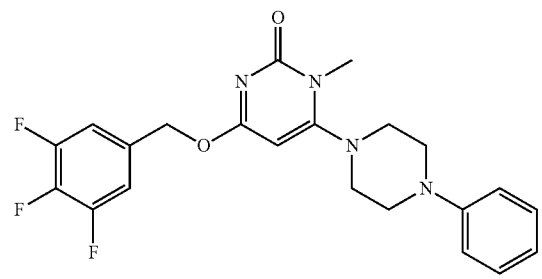 [SMILES: Cn1c(N2CCN(c3ccccc3)CC2)cc(OCc2cc(F)c(F)c(F)c2)nc1=O]

Intermediate 14 and intermediate 42 were used as raw materials. Reference was made to the preparation method of Example 1. $^1$H NMR (300 MHz, Chloroform-d) δ 7.35-7.27 (m, 2H), 7.11-7.01 (m, 2H), 7.00-6.92 (m, 3H), 5.50 (s, 1H), 5.34 (s, 2H), 3.50 (s, 3H), 3.38-3.30 (m, 4H), 3.23-3.14 (m, 4H). MS (ESI): 430 (M+H).

Example 14

4-(4-(4-chloro-3-(trifluoromethyl)phenoxy)-3,5-difluorobenzyl)oxy)-1-methyl-6-(4-methylpiperidinyl)pyrimidin-2(1H)-one

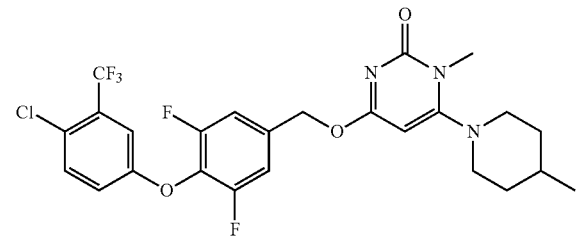 [SMILES: CC1CCN(c2cc(OCc3cc(F)c(Oc4ccc(Cl)c(C(F)(F)F)c4)c(F)c3)nc(=O)n2C)CC1]

Intermediate 13 and intermediate 35 were used as raw materials. Reference was made to the preparation method of Example 1. $^1$H NMR (400 MHz, Chloroform-d) δ 7.43 (d, J=8.8 Hz, 1H), 7.32 (d, J=3.0 Hz, 1H), 7.14-7.08 (m, 2H), 7.03 (dd, J=8.8, 3.0 Hz, 1H), 5.47 (s, 1H), 5.42 (s, 2H), 3.47 (s, 3H), 3.30 (d, J=12.4 Hz, 2H), 2.72 (td, J=12.1, 2.1 Hz, 2H), 1.85-1.77 (m, 2H), 1.43-1.32 (m, 3H), 1.04 (d, J=6.5 Hz, 3H). MS (ESI): 544 (M+H).

Example 15

4-(4-(4-chloro-3-(trifluoromethyl)phenoxy)-3,5-difluorobenzyl)oxy)-1-methyl-6-(4-methylpiperazinyl)pyrimidin-2(1H)-one

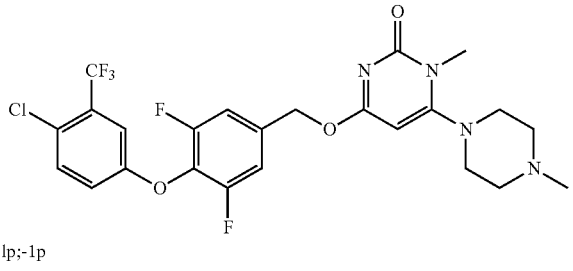

lp;-1p

Intermediate 16 and intermediate 37 were used as raw materials. Reference was made to the preparation method of Example 1. $^1$H NMR (400 MHz, Chloroform-d) δ 7.43 (d, J=8.8 Hz, 1H), 7.32 (d, J=3.0 Hz, 1H), 7.15-7.08 (m, 2H), 7.03 (dd, J=8.8, 3.0 Hz, 1H), 5.55 (s, 1H), 5.42 (s, 2H), 3.48 (s, 3H), 3.30 (s, 4H), 2.94 (s, 4H), 2.63 (s, 3H). MS (ESI): 545 (M+H).

Example 16

4-(4-(4-chloro-3-(trifluoromethyl)phenoxy)-3,5-difluorobenzyl)oxy)-6-(3,3-difluoropyrrolidinyl)-1-methylpyrimidin-2(1H)-one

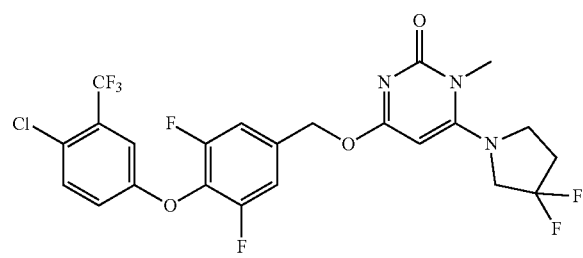 [SMILES: Cn1c(N2CCC(F)(F)C2)cc(OCc2cc(F)c(Oc3ccc(Cl)c(C(F)(F)F)c3)c(F)c2)nc1=O]

Intermediate 18 and intermediate 37 were used as raw materials. Reference was made to the preparation method of Example 1. $^1$H NMR (400 MHz, Chloroform-d) δ 7.44 (d, J=8.8 Hz, 1H), 7.31 (d, J=2.9 Hz, 1H), 7.12 (d, J=8.2 Hz, 2H), 7.03 (dd, J=8.8, 2.9 Hz, 1H), 5.42 (s, 3H), 3.66 (t, J=12.4 Hz, 2H), 3.54 (t, J=6.9 Hz, 2H), 3.51 (s, 3H), 2.57-2.46 (m, 2H). MS (ESI): 552 (M+H).

Example 17

4-(4-(4-chloro-3-(trifluoromethyl)phenoxy)-3,5-difluorobenzyl)oxy)-6-(4,4-difluoropiperidyl)-1-methylpyrimidin-2(1H)-one

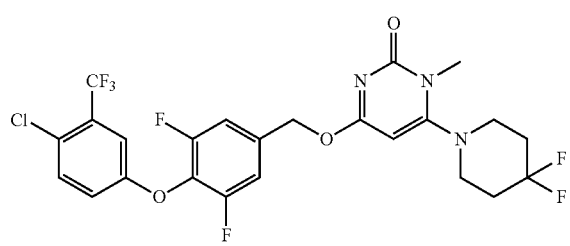 [SMILES: Cn1c(N2CCC(F)(F)CC2)cc(OCc2cc(F)c(Oc3ccc(Cl)c(C(F)(F)F)c3)c(F)c2)nc1=O]

Intermediate 19 and intermediate 37 were used as raw materials. Reference was made to the preparation method of Example 1. $^1$H NMR (400 MHz, Chloroform-d) δ 7.44 (d, J=8.8 Hz, 1H), 7.31 (d, J=3.0 Hz, 1H), 7.15-7.08 (m, 2H), 7.04 (dd, J=8.9, 3.0 Hz, 1H), 5.53 (s, 1H), 5.42 (s, 2H), 3.50 (s, 3H), 3.17 (t, J=5.7 Hz, 4H), 2.26-2.14 (m, 4H). MS (ESI): 566 (M+H).

Example 18

4-((4-(4-chloro-3-(trifluoromethyl)phenoxy)-3,5-difluorobenzyl)oxy)-6((2-methoxyethyl)(methyl)amino)-1-methylpyrimidin-2(1H)-one

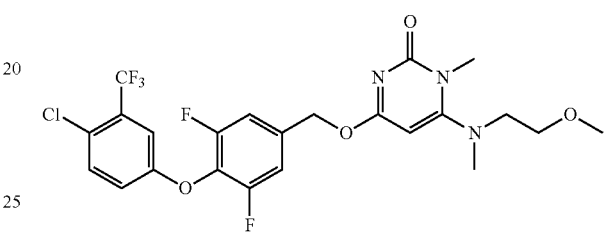

Intermediate 20 and intermediate 37 were used as raw materials. Reference was made to the preparation method of Example 1. $^1$H NMR (400 MHz, Chloroform-d) δ 7.44 (d, J=8.8 Hz, 1H), 7.32 (d, J=3.0 Hz, 1H), 7.15-7.09 (m, 2H), 7.03 (dd, J=8.8, 2.9 Hz, 1H), 5.51 (s, 1H), 5.42 (s, 2H), 3.60 (t, J=5.3 Hz, 2H), 3.49 (s, 3H), 3.37 (s, 3H), 3.28 (t, J=5.3 Hz, 2H), 2.88 (s, 3H). MS (ESI): 534 (M+H).

Example 19

4-((4-(4-chloro-3-(trifluoromethyl)phenoxy)-3,5-difluorobenzyl)oxy)-1-methyl-6-phenylpyrimidin-2(1H)-one

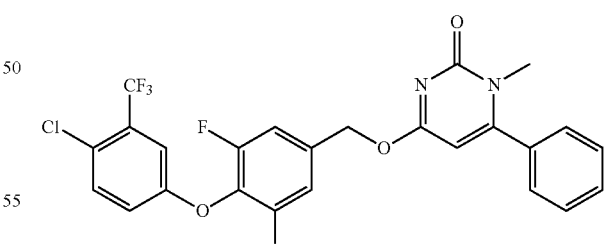

Intermediate 23 and intermediate 37 were used as raw materials. Reference was made to the preparation method of Example 1. $^1$H NMR (400 MHz, Chloroform-d) δ 7.57-7.51 (m, 3H), 7.46-7.37 (m, 3H), 7.32 (d, J=3.0 Hz, 1H), 7.18-7.12 (m, 2H), 7.04 (dd, J=8.7, 3.1 Hz, 1H), 5.94 (s, 1H), 5.49 (s, 2H), 3.39 (s, 3H). MS (ESI): 523 (M+H).

Example 20

4-((4-(4-chloro-3-(trifluoromethyl)phenoxy)-3,5-difluorobenzyl)oxy)-6-(4-methoxyphenyl)-1-methyl-pyrimidin-2(1H)-one

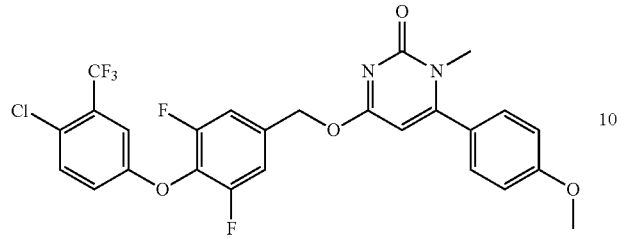

Intermediate 24 and intermediate 37 were used as raw materials. Reference was made to the preparation method of Example 1. $^1$H NMR (400 MHz, Chloroform-d) δ7.44 (d, J=8.8 Hz, 1H), 7.35-7.31 (m, 3H), 7.17-7.11 (m, 2H), 7.06-7.01 (m, 3H), 5.92 (s, 1H), 5.48 (s, 2H), 3.90 (s, 3H), 3.41 (s, 3H). MS (ESI): 553 (M+H).

Example 21

4-((4-(4-chloro-3-(trifluoromethyl)phenoxy)-3,5-difluorobenzyl)oxy)-1-methyl-6-(1-methyl-1H-pyrazolyl-4)pyrimidin-2(1H)-one

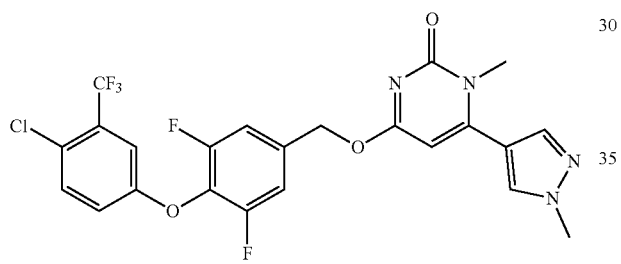

Intermediate 25 and intermediate 37 were used as raw materials. Reference was made to the preparation method of Example 1. $^1$H NMR (400 MHz, Chloroform-d) δ 7.71 (s, 1H), 7.67 (s, 1H), 7.44 (d, J=8.8 Hz, 1H), 7.32 (d, J=3.0 Hz, 1H), 7.17-7.09 (m, 2H), 7.04 (dd, J=8.9, 3.0 Hz, 1H), 5.97 (s, 1H), 5.46 (s, 2H), 4.03 (s, 3H), 3.61 (s, 3H). MS (ESI): 527 (M+H).

Example 22

4-(3,5-difluoro-4-(6-(trifluoromethyl)pyridin-3-yl)oxy)benzyl)oxy)-6-(dimethylamino)-1-methylpyrimidin-2(1H)-one

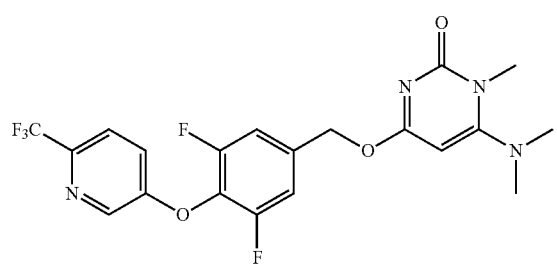

Intermediate 12 and intermediate 41 were used as raw materials. Reference was made to the preparation method of Example 1. $^1$H NMR (400 MHz, Chloroform-d) δ 8.51 (d, J=2.8 Hz, 1H), 7.65 (d, J=8.7 Hz, 1H), 7.31 (dd, J=8.7, 2.8 Hz, 1H), 7.18-7.11 (m, 2H), 5.45 (s, 1H), 5.43 (s, 2H), 3.49 (s, 3H), 2.85 (s, 6H). MS (ESI): 457 (M+H).

Example 23

2-(4-chloro-3-(trifluoromethyl)phenoxy)-5-(((6-((2-methoxyethyl)(methyl)amino)-1-2-oxo-1,2-tetrahydropyrimidin-4-yl)oxy)methyl)benzonitrile

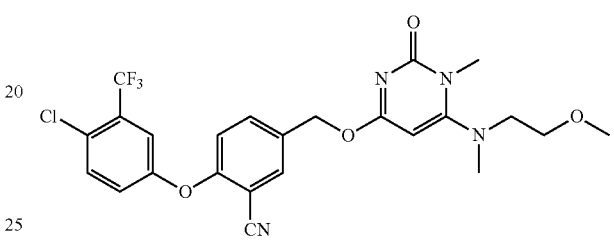

Intermediate 20 and intermediate 40 were used as raw materials. Reference was made to the preparation method of Example 1. $^1$H NMR (400 MHz, Chloroform-d) δ 7.78 (d, J=2.0 Hz, 1H), 7.61 (dd, J=8.6, 2.2 Hz, 1H), 7.55 (d, J=8.7 Hz, 1H), 7.43 (d, J=2.9 Hz, 1H), 7.28 (s, 1H), 7.19 (dd, J=8.7, 2.9 Hz, 1H), 6.93 (d, J=8.6 Hz, 1H), 5.48 (s, 1H), 5.42 (s, 2H), 3.60 (t, J=5.3 Hz, 2H), 3.48 (s, 3H), 3.36 (s, 3H), 3.27 (t, J=5.3 Hz, 2H), 2.87 (s, 3H). MS (ESI): 523 (M+H).

Example 24

4-((4-(4-chloro-3-(trifluoromethyl)phenoxy)benzyl)oxy)-1-methyl-6-morpholinopyrimidin-2(1H)-one

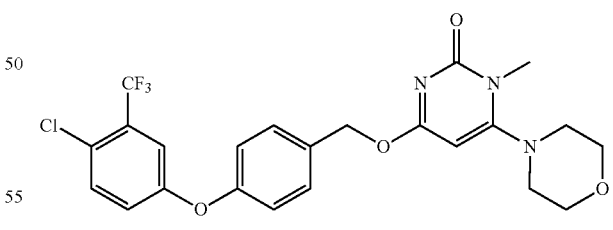

Intermediate 5 and intermediate 34 were used as raw materials. Reference was made to the preparation method of Example 1. $^1$H NMR (400 MHz, Chloroform-d) δ 7.49-7.42 (m, 3H), 7.35 (d, J=2.5 Hz, 1H), 7.10 (dd, J=8.7, 2.4 Hz, 1H), 7.03 (d, J=8.3 Hz, 2H), 5.47 (s, 1H), 5.41 (s, 2H), 3.89-3.83 (m, 4H), 3.50 (s, 3H), 3.05-2.99 (m, 4H). MS (ESI): 496 (M+H).

Example 25

4-(4-(4-chloro-3-(trifluoromethyl)phenoxy)-3-fluorobenzyl)oxy)-1-methyl-6-morpholinopyrimidin-2(1H)-one

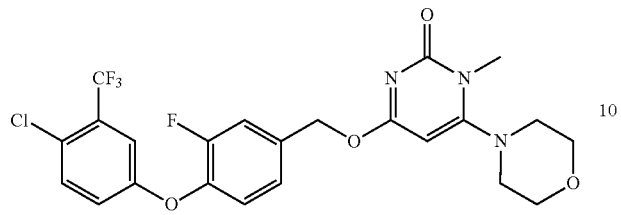

Intermediate 5 and intermediate 39 were used as raw materials. Reference was made to the preparation method of Example 1. $^1$H NMR (400 MHz, Chloroform-d) δ 7.44 (d, J=8.8 Hz, 1H), 7.34-7.29 (m, 2H), 7.23 (d, J=8.3 Hz, 1H), 7.12 (t, J=8.2 Hz, 1H), 7.05 (dd, J=8.8, 3.0 Hz, 1H), 5.49 (s, 1H), 5.42 (s, 2H), 3.89-3.85 (m, 4H), 3.50 (s, 3H), 3.07-3.02 (m, 4H). MS (ESI): 514 (M+H).

Example 26

4-(3,5-difluoro-4-(6-(trifluoromethyl)pyridin-3-yl)oxy)benzyl)oxy)-1-methyl-6-morpholinopyrimidin-2(1H)-one

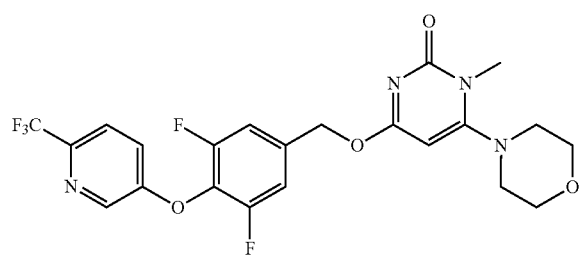

Intermediate 5 and intermediate 41 were used as raw materials. Reference was made to the preparation method of Example 1. $^1$H NMR (400 MHz, Chloroform-d) δ 8.51 (d, J=2.8 Hz, 1H), 7.65 (d, J=8.7 Hz, 1H), 7.32 (dd, J=8.7, 2.8 Hz, 1H), 7.18-7.11 (m, 2H), 5.50 (s, 1H), 5.44 (s, 2H), 3.92-3.84 (m, 4H), 3.51 (s, 3H), 3.09-3.02 (4, 5H). MS (ESI): 499 (M+H).

Example 27

2-(4-chloro-3-(trifluoromethyl)phenoxy)-5-((1-methyl-6-morpholinyl-2-oxo-1,2-dihydropyrimidin-4-oxy)methyl)benzonitrile

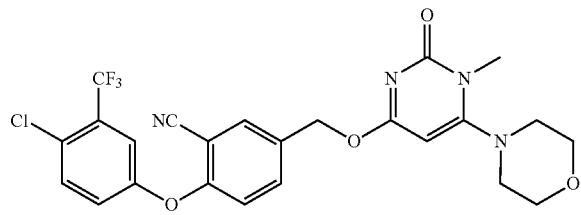

Intermediate 5 and intermediate 40 were used as raw materials. Reference was made to the preparation method of Example 1. $^1$H NMR (400 MHz, Chloroform-d) δ 7.78 (d, J=2.2 Hz, 1H), 7.62 (dd, J=8.7, 2.2 Hz, 1H), 7.55 (d, J=8.7 Hz, 1H), 7.43 (d, J=2.8 Hz, 1H), 7.20 (dd, J=8.7, 2.8 Hz, 1H), 6.93 (d, J=8.7 Hz, 1H), 5.48 (s, 1H), 5.43 (s, 2H), 3.90-3.84 (m, 4H), 3.50 (s, 3H), 3.08-3.02 (m, 4H). MS (ESI): 521 (M+H).

Example 28

1-methyl-6-morpholinyl-4-(3,4,5-trifluorobenzyl)oxy)pyrimidin-2(1H)-one

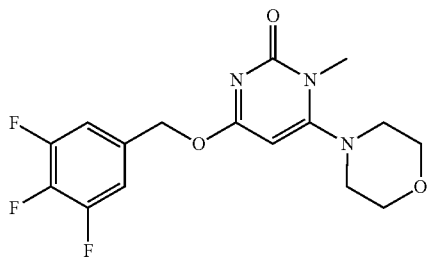

Intermediate 5 and intermediate 42 were used as raw materials. Reference was made to the preparation method of Example 1. $^1$H NMR (400 MHz, Chloroform-d) δ 7.09-7.02 (m, 2H), 5.47 (s, 1H), 5.35 (s, 2H), 3.90-3.83 (m, 4H), 3.49 (s, 3H), 3.08-3.01 (m, 4H). MS (ESI): 356 (M+H).

Example 29

4-(3,5-difluoro-4-(2-(trifluoromethyl)pyridin-4-yl)oxybenzyl)oxy)-1-methyl-6-morpholinopyrimidin-2(1H)-one

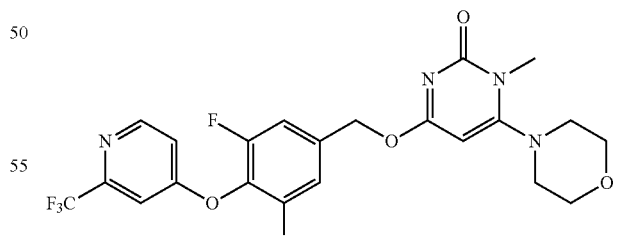

Intermediate 5 and intermediate 43 were used as raw materials. Reference was made to the preparation method of Example 1. $^1$H NMR (400 MHz, Chloroform-d) δ 8.63 (d, J=5.7 Hz, 1H), 7.28 (d, J=2.3 Hz, 1H), 7.17 (d, J=8.1 Hz, 2H), 7.01 (dd, J=5.7, 2.3 Hz, 1H), 5.51 (s, 1H), 5.45 (s, 2H), 3.91-3.86 (m, 4H), 3.51 (s, 3H), 3.09-3.03 (m, 4H). MS (ESI): 499 (M+H).

Example 30

4-(4-(6-chloropyridin-3-yl)oxy)-3,5-difluorobenzyl)oxy)-1-methyl-6-morpholinopyrimidin-2(1H)-one

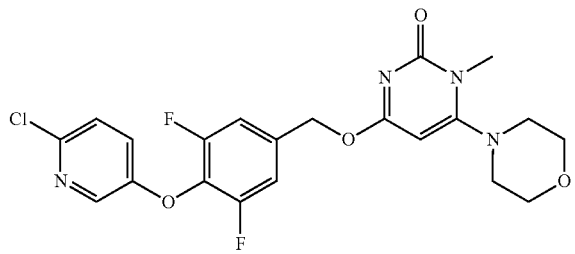

4-((4-((6-chloropyridin-3-yl)oxy)-3,5-difluorobenzyl)oxy)-1-methyl-6-morpholinopyrimidin-2(1H)-one Intermediate 5 and intermediate 44 were used as raw materials. Reference was made to the preparation method of Example 1. $^1$H NMR (400 MHz, Chloroform-d) δ 8.16 (d, J=2.8 Hz, 1H), 7.27 (s, 1H), 7.25 (d, J=2.8 Hz, 1H), 7.12 (d, J=8.2 Hz, 2H), 5.50 (s, 1H), 5.42 (s, 2H), 3.90-3.86 (m, 4H), 3.50 (s, 3H), 3.11-3.01 (m, 4H). MS (ESI): 465 (M+H).

Example 31

4-((3-chloro-4-(4-chloro-3-(trifluoromethyl)phenoxy)benzyl)oxy)-1-methyl-6-morpholinopyrimidin-2(1H)-one

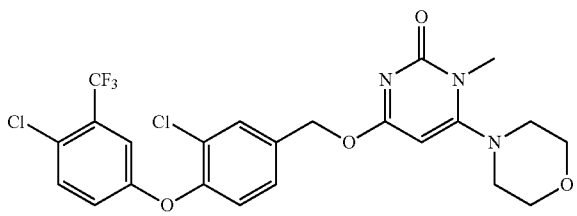

Intermediate 5 and intermediate 45 were used as raw materials. Reference was made to the preparation method of Example 1. $^1$H NMR (400 MHz, Chloroform-d) δ 7.58 (s, 1H), 7.45 (d, J=8.8 Hz, 1H), 7.36 (d, J=8.2 Hz, 1H), 7.30 (d, J=2.6 Hz, 1H), 7.06 (d, J=8.4 Hz, 1H), 7.01 (dd, J=8.7, 2.6 Hz, 1H), 5.49 (s, 1H), 5.42 (s, 2H), 3.91-3.85 (m, 4H), 3.50 (s, 3H), 3.07-3.01 (m, 4H). MS (ESI): 530 (M+H).

Example 32

4-((4-(4-chloro-3-(trifluoromethyl)phenoxy)-3-methylbenzyl)oxy)-1-methyl-6-morpholinopyrimidin-2(1H)-one

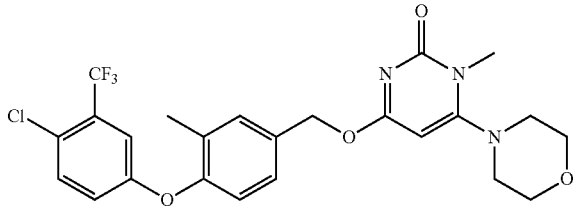

Intermediate 5 and intermediate 46 were used as raw materials. Reference was made to the preparation method of Example 1. $^1$H NMR (400 MHz, Methanol-d$_4$) δ 7.56 (d, J=8.8 Hz, 1H), 7.46-7.43 (m, 1H), 7.36 (dd, J=8.2, 1.8 Hz, 1H), 7.26 (d, J=2.9 Hz, 1H), 7.08 (dd, J=8.9, 2.9 Hz, 1H), 6.99 (d, J=8.3 Hz, 1H), 5.70 (s, 1H), 5.37 (s, 2H), 3.87-3.82 (m, 4H), 3.48 (s, 3H), 3.12-3.07 (m, 4H). MS (ESI): 510 (M+H).

Example 33

4-((3,5-difluoro-4-(4-fluoro-3-(trifluoromethyl)phenoxy)benzyl)oxy)-1-methyl-6-morpholinopyrimidin-2(1H)-one

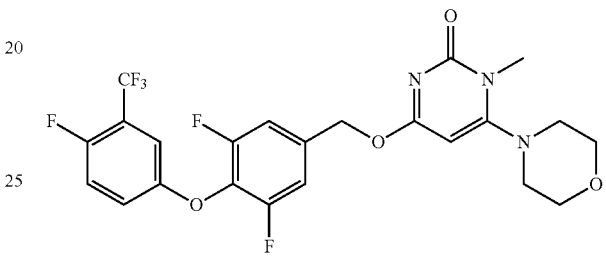

Intermediate 5 and intermediate 47 were used as raw materials. Reference was made to the preparation method of Example 1. $^1$H NMR (400 MHz, Chloroform-d) δ7.20 (dt, J=6.4, 3.2 Hz, 1H), 7.17-7.08 (m, 4H), 5.50 (s, 1H), 5.42 (s, 2H), 3.92-3.85 (m, 4H), 3.51 (s, 3H), 3.09-3.01 (m, 4H). MS (ESI): 516 (M+H).

Example 34

4-(4-(4-chloro-3-(trifluoromethyl)phenoxy-3,5-difluorobenzyl)oxy)-1-ethyl-6-morpholinopyrimidin-2(1H)-one

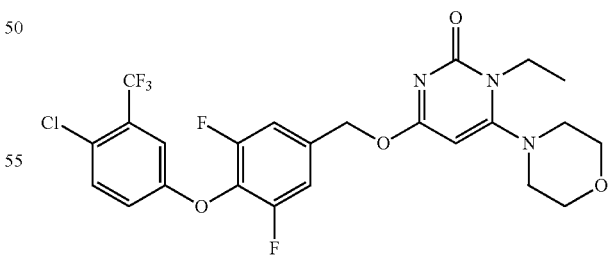

Intermediate 6 and intermediate 37 were used as raw materials. Reference was made to the preparation method of Example 1. $^1$H NMR (400 MHz, Chloroform-d) δ 7.44 (d, J=8.8 Hz, 1H), 7.32 (d, J=2.9 Hz, 1H), 7.12 (d, J=8.1 Hz, 2H), 7.04 (dd, J=8.8, 3.0 Hz, 1H), 5.54 (s, 1H), 5.42 (s, 2H), 4.05 (q, J=6.9 Hz, 2H), 3.90-3.84 (m, 4H), 3.07-2.99 (m, 4H), 1.37 (t, J=6.9 Hz, 3H). MS (ESI): 546 (M+H).

Example 35

4-(4-(4-chloro-3-(trifluoromethyl)phenoxy-3,5-difluorobenzyl)oxy)-1-propyl-6-morpholinopyrimidin-2(1H)-one

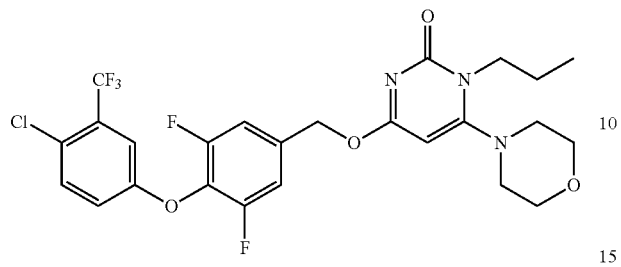

Intermediate 7 and intermediate 37 were used as raw materials. Reference was made to the preparation method of Example 1. $^1$H NMR (400 MHz, Chloroform-d) δ 7.44 (d, J=8.8 Hz, 1H), 7.32 (d, J=3.0 Hz, 1H), 7.12 (d, J=8.1 Hz, 2H), 7.04 (dd, J=8.8, 3.0 Hz, 1H), 5.54 (s, 1H), 5.41 (s, 2H), 3.97-3.91 (m, 2H), 3.90-3.85 (m, 4H), 3.04-2.98 (m, 4H), 1.80 (dt, J=14.8, 7.4 Hz, 2H), 0.94 (t, J=7.4 Hz, 3H). MS (ESI): 560 (M+H).

Example 36

4-((4-(4-chloro-3-(trifluoromethyl)phenoxy)-3-fluorobenzyl)oxy)-1-methyl-6-(pyrrolidin-1-yl)pyrimidin-2(1H)-one

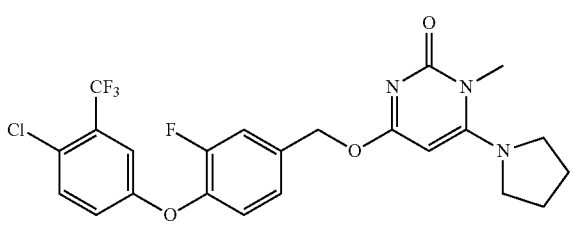

Intermediate 4 and intermediate 39 were used as raw materials. Reference was made to the preparation method of Example 1. $^1$H NMR (400 MHz, Chloroform-d) δ 7.43 (d, J=8.8 Hz, 1H), 7.31 (dd, J=11.4, 2.3 Hz, 2H), 7.22 (d, J=8.9 Hz, 1H), 7.10 (t, J=8.2 Hz, 1H), 7.04 (dd, J=8.8, 2.9 Hz, 1H), 5.42 (s, 2H), 5.34 (s, 1H), 3.51 (s, 3H), 3.38-3.33 (m, 4H), 2.04-1.98 (m, 4H). MS (ESI): 498 (M+H).

Example 37

4-((4-(4-chloro-3-(trifluoromethyl)phenoxy)-3,5-difluorobenzyl)oxy)-6-(4-fluoropiperidin-1-yl)-1-methylpyrimidin-2(1H)-one

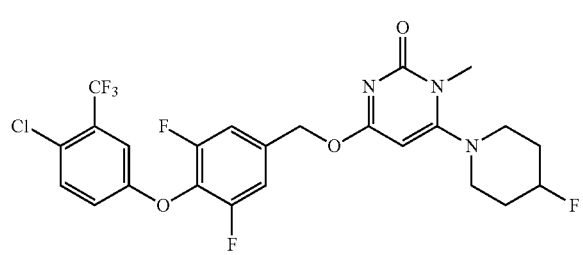

Intermediate 22 and intermediate 37 were used as raw materials. Reference was made to the preparation method of Example 1. $^1$H NMR (400 MHz, Chloroform-d) δ 7.44 (d, J=8.8 Hz, 1H), 7.32 (d, J=2.9 Hz, 1H), 7.13 (t, J=6.9 Hz, 2H), 7.03 (dd, J=8.8, 2.8 Hz, 1H), 5.52 (s, 1H), 5.42 (s, 2H), 5.04-4.83 (m, 1H), 3.49 (s, 3H), 3.18 (td, J=10.7, 9.2, 3.1 Hz, 2H), 3.09-2.99 (m, 2H), 2.13-1.94 (m, 4H). MS (ESI): 548 (M+H).

Example 38

4-((4-(4-chloro-3-(trifluoromethyl)phenoxy)-3-fluorobenzyl)oxy)-6-(4,4-difluoropiperidin-1-yl)-1-methylpyrimidin-2(1H)-one

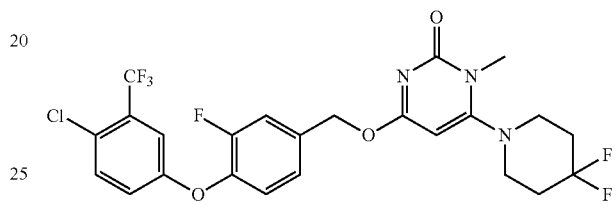

Intermediate 19 and intermediate 39 were used as raw materials. Reference was made to the preparation method of Example 1. $^1$H NMR (400 MHz, Chloroform-d) δ 7.44 (d, J=8.8 Hz, 1H), 7.31 (dd, J=10.0, 2.3 Hz, 2H), 7.22 (d, J=8.3 Hz, 1H), 7.11 (t, J=8.2 Hz, 1H), 7.05 (dd, J=8.8, 2.9 Hz, 1H), 5.51 (s, 1H), 5.42 (s, 2H), 3.49 (s, 3H), 3.19-3.12 (m, 4H), 2.19 (tt, J=12.8, 6.2 Hz, 4H). MS (ESI): 548 (M+H).

Example 39

2-(4-chloro-3-(trifluoromethyl)phenoxy)-5-(((1-methyl-2-oxo-6-(pyrrolidin-1-yl)-1,2-dihydropyrimidin-4-yl)oxy)methyl)benzonitrile

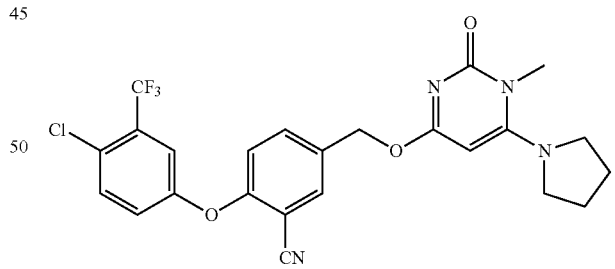

Intermediate 4 and intermediate 40 were used as raw materials. Reference was made to the preparation method of Example 1. $^1$H NMR (400 MHz, Chloroform-d) δ 7.75 (d, J=2.0 Hz, 1H), 7.60 (dd, J=8.7, 2.1 Hz, 1H), 7.53 (d, J=8.7 Hz, 1H), 7.41 (d, J=2.8 Hz, 1H), 7.18 (dd, J=8.7, 2.8 Hz, 1H), 6.91 (d, J=8.6 Hz, 1H), 5.41 (s, 2H), 5.33 (s, 1H), 3.49 (s, 3H), 3.39-3.33 (m, 4H), 2.04-1.98 (m, 4H). MS (ESI): 505 (M+H).

The compounds in the following examples were prepared by referring to the preparation method of example 1.

| example | compound name | structural formula | Raw materials | MS (ESI) |
|---|---|---|---|---|
| 40 | 2-(4-chloro-3-(trifluoromethyl)phenoxy)-5-(((1-methyl-2-oxo-6-(piperidin-1-yl)-1,2-dihydropyrimidin-4-yl)oxy)methyl)benzonitrile | | intermediate 8, intermediate 40 | 519 (M + H) |
| 41 | 4-((3-fluoro-4-((2-(trifluoromethyl)pyridin-4-yl)oxy)benzyl)oxy)-1-methyl-6-morpholinopyrimidin-2(1H)-one | | intermediate 5, intermediate 48 | 481 (M + H) |
| 42 | 5-(((1-methyl-6-morpholinyl-2-oxo-1,2-dihydropyrimidin-4-yl)oxy)methyl)-2-((5-trifluoromethyl)pyridin-3-yl)oxy)benzonitrile | | intermediate 5, intermediate 49 | 488 (M + H) |
| 43 | 4-((3,5-difluoro-4-((5-(trifluoromethyl)pyridin-3-yl)oxy)benzyl)oxy)-1-methyl-6-morpholinopyrimindin-2(1H)-one | | intermediate 5, intermediate 50 | 499 (M + H) |
| 44 | 4-(2,6-difluoro-4-((1-methyl-6-morpholinyl-2-oxo-1,2-dihydropyrimidin-4-yl)oxy)methyl)phenoxy)-2-(trifluoromethyl)benzonitrile | | intermediate 5, intermediate 51 | 523 (M + H) |
| 45 | 4-(2-fluoro-4-(((1-methyl-6-morpholinyl-2-oxo-1,2-dihydropyrimidin-4-yl)oxy)methyl)phenoxy)-2-(trifluoromethyl)benzonitrile | | intermediate 5, intermediate 52 | 505 (M + H) |

-continued

| example | compound name | structural formula | Raw materials | MS (ESI) |
|---|---|---|---|---|
| 46 | 4-(2-cyano-4-(((1-methyl-6-morpholinyl-2-oxo-1,2-dihydropyrimidin-4-yl)oxy)methyl)phenoxy)-2-(trifluoromethyl)benzonitrile) | | intermediate 5, intermediate 53 | 512 (M + H) |
| 47 | 2-(4-fluoro-3-(trifluoromethyl)phenoxy)-5-(((1-methyl-6-morpholinyl-2-oxo-1,2-dihydropyrimidin-4-yl)oxy)methyl)benzonitrile | | intermediate 5, intermediate 54 | 505 (M + H) |
| 48 | 5-(((1-methyl-6-morpholinyl-2-oxo-1,2-dihydropyrimidin-4-yl)oxy)methyl)-2-((6-(trifluoromethyl)pyridin-3-yl)oxy)benzonitrile | | intermediate 5, intermediate 55 | 488 (M + H) |
| 49 | 4-((4-(4-chloro-3-(trifluoromethyl)phenoxy)-3-fluorobenzyl)oxy)-1-methyl-6-(piperidin-1-yl)pyrimidin-2(1H)-one | | intermediate 8, intermediate 39 | 512 (M + H) |
| 50 | 4-((4-(4-chloro-3-(trifluoromethyl)phenoxy)-3-fluorobenzyl)oxy)-6-(4-methoxypiperidin-1-yl)-1-methylpyrimidin-2(1H)-one | | intermediate 10, intermediate 39 | 542 (M + H) |
| 51 | 4-((4-(4-chloro-3-(trifluoromethyl)phenoxy)-3-fluorobenzyl)oxy)-1-methyl-6-(4-methylpiperazin-3-yl)pyrimidin-2(1H)-one | | intermediate 16, intermediate 39 | 527 (M + H) |

-continued

| example | compound name | structural formula | Raw materials | MS (ESI) |
|---|---|---|---|---|
| 52 | 4-((4-(4-chloro-3-(trifluoromethyl)phenoxy)-3,5-difluorobenzyl)oxy)-6-(4-cyclopropylpiperazin-1-yl)-1-methylpyrimidin-2(1H)-one | | intermediate 17, intermediate 37 | 571 (M + H) |
| 53 | 4-((4-(4-chloro-3-(trifluoromethyl)phenoxy)-3-fluorobenzyl)oxy)-6-(3,3-difluoropyrrolidin-1-yl)-1-methylpyrimidin-2(1H)-one | | intermediate 18, intermediate 39 | 534 (M + H) |
| 54 | (S)-4-((4-(4-chloro-3-(trifluoromethyl)phenoxy)-3,5-difluorobenzyl)oxy)-1-methyl-6-(3-methylmorpholinyl)pyrimidin-2(1H)-one | | intermediate 21, intermediate 37 | 546 (M + H) |
| 55 | (S)-4-((4-(4-chloro-3-(trifluoromethyl)phenoxy)-3-fluorobenzyl)oxy)-1-methyl-6-(3-methylmorpholinyl)pyrimidin-2(1H)-one | | intermediate 21, intermediate 39 | 528 (M + H) |
| 56 | 4-((4-(4-chloro-3-(trifluoromethyl)phenoxy)-3-fluorobenzyl)oxy)-6-(4-fluoropiperidin-1-yl)-1-methylpyrimidin-2(1H)-one | | intermediate 22, intermediate 39 | 530 (M + H) |
| 57 | 4-((4-(4-chloro-3-(trifluoromethyl)phenoxy)-3-fluorophenyl)oxy)-1-methyl-6-(1-methyl-1H-pyrazol-4-yl) pyrimidin-2(1H)-one | | intermediate 25, intermediate 39 | 509 (M + H) |

-continued

| example | compound name | structural formula | Raw materials | MS (ESI) |
|---|---|---|---|---|
| 58 | 4-((4-(4-chloro-3-(trifluoromethyl)phenoxy)-3-fluorobenzyl)oxy)-1-methyl-6-(thien-3-yl)pyrimidin-2(1H)-one | | intermediate 26, intermediate 39 | 511 (M + H) |
| 59 | 4-((4-(4-chloro-3-(trifluoromethyl)phenoxy)-3-fluorobenzyl)oxy)-1-methyl-6-(pyridin-4-yl)pyrimidin-2(1H)-one | | intermediate 27, intermediate 39 | 506 (M + H) |
| 60 | 4-((4-(4-chloro-3-(trifluoromethyl)phenoxy)-3-fluorobenzyl)oxy)-1-methyl-6-(pyridin-3-yl)pyrimidin-2(1H)-one | | intermediate 28, intermediate 39 | 506 (M + H) |
| 61 | 6-((4-(4-chloro-3-(trifluoromethyl)phenoxy)-3-fluorobenzyl)oxy)-3-methyl-[4,5'-dipyrimidin]-2(3H)-one | | intermediate 29, intermediate 39 | 507 (M + H) |
| 62 | 6-((4-(4-chloro-3-(trifluoromethyl)phenoxy)-3-fluorobenzyl)oxy)-2'-methoxy-3-methyl-[4,5'-dipyrimidin]-2(3H)-one | | intermediate 30, intermediate 39 | 537 (M + H) |
| 63 | 4-((4-(4-chloro-3-(trifluoromethyl)phenoxy)-3-fluorobenzyl)oxy)-6-(4-fluorophenyl)-1-methylpyrimidin-2(1H)-one | | intermediate 31, intermediate 39 | 523 (M + H) |

| example | compound name | structural formula | Raw materials | MS (ESI) |
|---|---|---|---|---|
| 64 | 4-((4-(4-chloro-3-(trifluoromethyl)phenoxy)-3-fluorobenzyl)oxy)-1-methyl-6-(4-trifluoromethyl)phenyl)pyrimidin-2(1H)-one | | intermediate 32, intermediate 39 | 573 (M + H) |

Example 65

4-((4-(4-chloro-3-(trifluoromethyl)phenoxy)-3,5-difluorobenzyl)oxy)-6-methoxy-1-methylpyrimidin-2(1H)-one

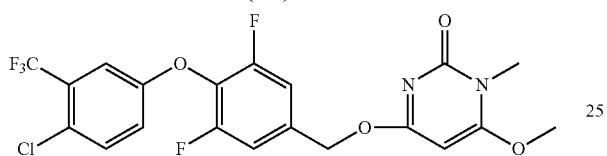

Intermediate 65 (34 mg, 1 eq.), methyl iodide (25 ul, 5 eq.) and potassium carbonate (23 mg, 2 eq.) were mixed in acetone, and the mixture was reacted at room temperature overnight, evaporated to remove solvent, and separated by column chromatography to give 25 mg of white solid.

1H NMR (400 MHz, Chloroform-d) δ 7.44 (d, J=8.8 Hz, 1H), 7.32 (d, J=2.9 Hz, 1H), 7.16-7.09 (m, 2H), 7.04 (dd, J=8.9, 3.0 Hz, 1H), 5.44 (s, 2H), 5.40 (s, 1H), 3.98 (s, 3H), 3.44 (s, 3H). MS (ESI): 477 (M+H).

Example 66

4-((4-(4-chloro-3-(trifluoromethyl)phenoxy)-3-fluorobenzyl)oxy)-6-methoxy-1-methylpyrimidin-2(1H)-one

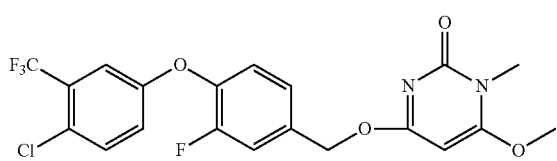

Intermediate 58 and methyl iodide were used as raw materials. Reference was made to the preparation method of Example 65. ¹H NMR (400 MHz, Chloroform-d) δ 7.43 (d, J=8.8 Hz, 1H), 7.32-7.28 (m, 2H), 7.21 (d, J=9.0 Hz, 1H), 7.10 (t, J=8.2 Hz, 1H), 7.04 (dd, J=8.8, 2.9 Hz, 1H), 5.42 (s, 2H), 5.37 (s, 1H), 3.95 (s, 3H), 3.42 (s, 3H). MS (ESI): 459 (M+H).

Example 67

2-(4-chloro-3-(trifluoromethyl)phenoxy)-5-(((6-methoxy-1-methyl-2-oxo-1,2-dihydropyrimidin-4-yl)oxy)methyl)benzonitrile

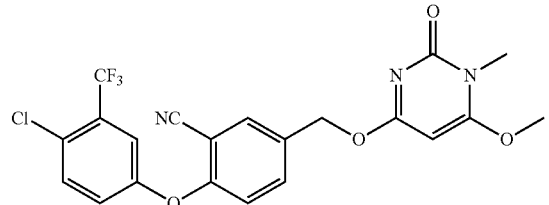

Intermediate 59 and methyl iodide were used as raw materials. Reference was made to the preparation method of Example 65. ¹H NMR (400 MHz, Chloroform-d) δ 7.76 (d, J=2.0 Hz, 1H), 7.60 (dd, J=8.7, 2.1 Hz, 1H), 7.54 (d, J=8.7 Hz, 1H), 7.41 (d, J=2.9 Hz, 1H), 7.19 (dd, J=8.7, 2.8 Hz, 1H), 6.92 (d, J=8.6 Hz, 1H), 5.42 (s, 2H), 5.36 (s, 1H), 3.96 (s, 3H), 3.42 (s, 3H). MS (ESI): 466 (M+H).

The compounds in the following examples were prepared by referring to the preparation method of example 65.

| example | compound name | structure formula | raw materials | MS (ESI) |
|---|---|---|---|---|
| 68 | 4-((3-fluoro-4-((2-(trifluoromethyl)pyridin-4-yl)oxy)benzyl)oxy)-6-methoxy-1-methylpyrimidin-2(1H)-one | | intermediate 60 | 426 (M + H) |

-continued

| example | compound name | structure formula | raw materials | MS (ESI) |
|---|---|---|---|---|
| 69 | 4-((3,5-difluoro-4-((2-(trifluoromethyl)pyridin-4-yl)oxy)benzyl)oxy)-6-methoxy-1-methylpyrimidin-2(1H)-one | | intermediate 61 | 443 (M + H) |
| 70 | 4-((3,5-difluoro-4-((6-(trifluoromethyl)pyridin-3-yl)oxy)benzyl)oxy)-6-methoxy-1-methylpyrimidin-2(1H)-one | | intermediate 62 | 443 (M + H) |
| 71 | 4-((4-(4-chloro-3-(trifluoromethyl)phenoxy)benzyl)oxy)-6-methoxy-1-methylpyrimidin-2(1H)-one | | intermediate 57 | 441 (M + H) |
| 72 | 5-(((6-methoxy-1-methyl-2-oxo-1,2-dihydropyrimidin-4-yl)oxy)methyl)-2-((5-(trifluoromethyl)pyridin-3-yl)oxy)benzonitrile | | intermediate 63 | 433 (M + H) |
| 73 | 4-((3,5-difluoro-4-((5-(trifluoromethyl)pyridin-3-yl)oxy)benzyl)oxy)-6-methoxy-1-methylpyrimidin-2(1H)-one | | intermediate 64 | 444 (M + H) |
| 74 | 4-((2,6-difluoro-4-(((6-methoxy-1-methyl-2-oxo-1,2-dihydropyrimidin-4-yl)oxy)methyl)phenoxy)-2-(trifluoromethyl)benzonitrile | | intermediate 65 | 468 (M + H) |

| example | compound name | structure formula | raw materials | MS (ESI) |
|---|---|---|---|---|
| 75 | 4-(2-fluoro-4-(((6-methoxy-1-methyl-2-oxo-1,2-dihydropyrimtdin-4-yl)oxy)methyl)phenoxy)-2-(trifluoromethyl)benzonitrile | | intermediate 66 | 450 (M + H) |
| 76 | 4-(2-cyano-4-(((6-methoxy-1-methyl-2-oxo-1,2-dihydropyrimidin-4-yl)oxy)methyl)phenoxy)-2-(trifluoromethyl)benzonitrile | | intermediate 67 | 457 (M + H) |
| 77 | 2-(4-fluoro-3-(trifluoromethyl)phenoxy)-5-(((6-methoxy-1-methyl-2-oxo-1,2-dihydropyrimidin-4-yl)oxy)methyl)benzonitrile | | intermediate 68 | 450 (M + H) |

Example 78

4-((4-(4-chloro-3-(trifluoromethyl)phenoxy)-3,5-difluorobenzyl)oxy)-6-(1,1-dioxomercaptomorpholino)-1-methylpyrimidin-2(1H)-one

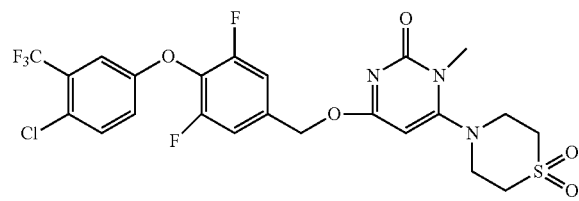

The compound of Example 8 (30 mg, 1 eq.) and m-chloroperoxybenzoic acid (40 mg, 70%, 3 eq.) were mixed in dichloromethane and stirred at room temperature for 2 h. Saturated aqueous sodium bicarbonate solution was added to quench the reaction and the mixture was extracted with dichloromethane, rinsed with saturated brine, dried over anhydrous sodium sulfate, filtered, evaporated to dryness, and separated by column chromatography to give 20 mg product. $^1$H NMR (400 MHz, Chloroform-d) δ 7.44 (d, J=8.8 Hz, 1H), 7.31 (d, J=3.0 Hz, 1H), 7.15-7.09 (m, 2H), 7.04 (dd, J=8.8, 2.9 Hz, H1H), 5.58 (s, 1H), 5.43 (s, 2H), 3.61-3.54 (m, 4H), 3.52 (s, 3H), 3.31-3.23 (m, 4H). MS (ESI): 580 (M+H).

Example 79

4-(6-((4-(4-chloro-3-(trifluoromethyl)phenoxy)-3,5-difluorobenzyl)oxy)-3-methyl-2-oxo-2,3-dihydropyrimidin-4-yl)-1-methylpiperazine tartrate

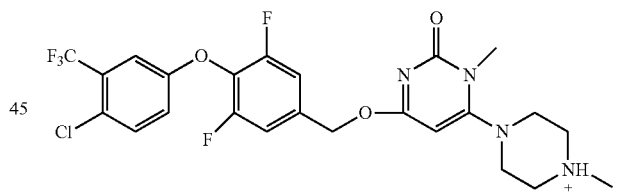

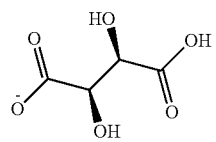

Example 15 (24 mg, 1 eq.) and tartaric acid (6.6 mg, 1 eq.) were mixed in anhydrous methanol and stirred for 30 min. The raw materials were completely dissolved and the mixture was evaporated to remove solvent to give the salt product. $^1$H NMR (400 MHz, Chloroform-d) δ 7.44 (d, J=8.5 Hz, 1H), 7.32 (s, 2H), 7.12 (d, J=8.1 Hz, 2H), 7.04 (d, J=9.4 Hz, 1H), 5.59 (s, 1H), 5.43 (s, 2H), 5.37 (s, 1H), 3.50 (d, J=11.8 Hz, 9H), 3.18 (s, 4H), 2.80 (s, 3H). MS (ESI): 545 (M+H).

Example 80

4-((4-(4-chloro-3-(trifluoromethyl)phenoxy)-3,5-difluorobenzyl)oxy)-1,6-dimethylpyrimidin-2(1H)-one

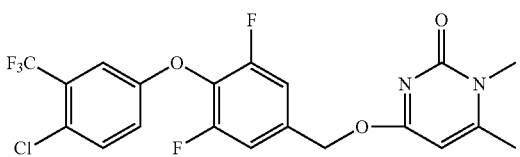

Intermediate 73 (35 mg, 1 eq.), methyl iodide (25 ul, 5 eq.) and potassium carbonate (23 mg, 2 eq.) were mixed in acetone, and the mixture was reacted at room temperature overnight, evaporated to remove solvent, and separated by column chromatography to give 25 mg of white solid. $^1$H NMR (400 MHz, Chloroform-d) δ 7.44 (d, J=8.8 Hz, 1H), 7.32 (d, J=3.0 Hz, 1H), 7.15-7.08 (m, 2H), 7.03 (dd, J=8.8, 2.9 Hz, 1H), 5.87 (s, 1H), 5.42 (s, 2H), 3.53 (s, 3H), 2.37 (s, 3H). MS (ESI): 461 (M+H).

Example 81

4-((4-(4-chloro-3-(trifluoromethyl)phenoxy)-3,5-difluorobenzyl)oxy)-1-ethyl-6-methylpyrimidin-2(1H)-one

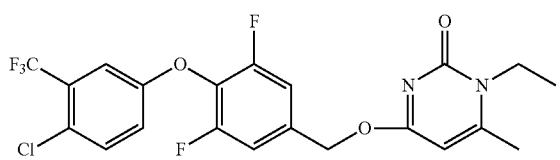

Intermediate 73 and ethyl iodide were used as raw materials. Reference was made to the preparation method of Example 80. $^1$H NMR (400 MHz, Chloroform-d) δ 7.44 (d, J=8.7 Hz, 1H), 7.32 (d, J=2.8 Hz, 1H), 7.15-7.07 (m, 2H), 7.06-7.00 (m, 1H), 5.84 (s, 1H), 5.41 (s, 2H), 4.06 (q, J=7.0 Hz, 2H), 2.40 (s, 3H), 1.35 (t, J=7.1 Hz, 3H). MS (ESI): 510 (M+H). MS (ESI): 475 (M+H).

Example 82

4-((4-(4-chloro-3-(trifluoromethyl)phenoxy)-3,5-difluorobenzyl)oxy)-6-methyl-1-((1-methyl-1H-pyrazol-4-yl)methyl)pyrimidin-2(1H)-one

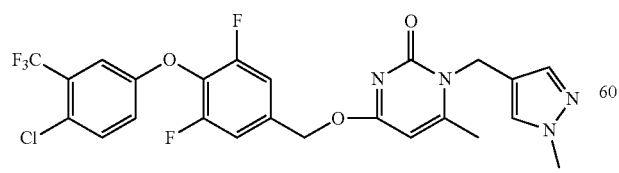

Intermediate 73 (45 mg, 1 eq.), intermediate 71 (39 mg, 3 eq.) and cesium carbonate (197 mg, 6 eq.) were mixed in N, N-dimethylformamide and reacted at 110° C. under microwave for 60 min. The mixture was added with water, extracted with ethyl acetate three times, rinsed with water twice, dried over anhydrous sodium sulfate, filtered, evaporated to dryness, and separated by column chromatography to give 10 mg of white solid. $^1$H NMR (400 MHz, Chloroform-d) δ 7.44 (dd, J=14.5, 8.6 Hz, 3H), 7.31 (d, J=2.7 Hz, 1H), 7.18 (d, J=8.3 Hz, 2H), 7.01 (dd, J=8.9, 2.7 Hz, 1H), 5.67 (s, 1H), 5.12 (s, 2H), 4.92 (s, 2H), 3.90 (s, 3H), 2.37 (s, 3H). MS (ESI): 541 (M+H).

Example 83

4-((4-(4-chloro-3-(trifluoromethyl)phenoxy)-3-fluorobenzyl)oxy)-6-methyl-1-(pyridin-3-ylmethyl)pyrimidin-2(1H)-one

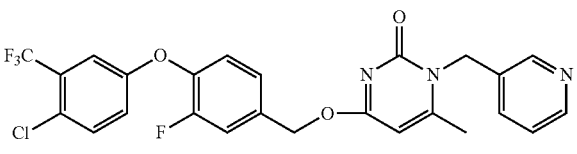

Intermediate 75 and 3-(chloromethyl)pyridine hydrochloride were used as raw materials. Reference was made to the preparation method of Example 82. $^1$H NMR (400 MHz, Chloroform-d) δ 8.56 (dd, J=5.0, 1.5 Hz, 1H), 8.54 (d, J=1.9 Hz, 1H), 7.66 (dt, J=8.2, 1.8 Hz, 1H), 7.43 (d, J=8.8 Hz, 1H), 7.33-7.27 (m, 3H), 7.22 (d, J=8.6 Hz, 1H), 7.10 (t, J=8.1 Hz, 1H), 7.04 (dd, J=8.9, 2.8 Hz, 1H), 5.85 (s, 1H), 5.43 (s, 2H), 5.27 (s, 2H), 2.30 (s, 3H). MS (ESI): 538 (M+H).

PHARMACOLOGY EXAMPLES

Example 1: In Vitro Inhibitory Activity Assay

Reagents 1) reaction buffer
0.1M Tris-HCl, 1 mM EGTA, PH 7.2
2) thioester analogs of phosphatidylcholine (2-thio-PAF, Cayman, Lot 60945)
Anhydrous ethanol was used as solvent to make a 25 mg/ml mother liquor. The solution was aliquoted, stored at −80° C. and diluted 900 times before use (about 50 μM of concentration)
3) DTNB (5,5'-dithio-bis-(2-nitrobenzoic acid), Sigma, Lot D8130)
The solution was prepared just before use. Triple distilled water was used to make a concentration of 1.1 mg/ml, and an appropriate amount of 0.1M NaOH was added until DTNB was just dissolved.
4) Compound was dissolved in DMSO to a suitable concentration.

Experiment Principle

Lp-PLA$_2$ activity was determined by using 2-thio-PAF as substrate. The thiol group produced upon the hydrolysis of 2-thio-PAF can react with DTNB to generate a yellow substance. The optical density at 414 nm can be detected to reflect Lp-PLA$_2$ activity.

1.1 Determination of the Inhibitory Activity of the Compounds on Lp-PLA$_2$ (Rabbit Serum as the Source of Enzyme) (In Vitro)

1.1.1 Experiment Methods

1) The corresponding reagents were added according to Table 1 and mixed uniformly by shaking.

TABLE 1

The list of the reaction system

| | blank well | sample well | control well |
|---|---|---|---|
| reaction buffer | 30 μL | 20 μL | 20 μL |
| rabbit serum (source of the enzyme) | | 10 μL | 10 μL |
| DMSO | 10 μL | | 10 μL |
| sample (in DMSO) | | 10 L | |

2) 10 μL of DTNB was added to each well.
3) 150 μL of 2-thio-PAF was added to each well and shaken for 15 s on a microplate reader to mix the liquid in the well uniformly. The detection was carried out at 414 nM over 10 minutes, once per minute and the slope was measured. The inhibitory ratio was calculated according to the following formula:

inhibitory ratio=1−(the slope of the sample well−the slope of the blank well)/(the slope of the control well−the slope of the blank well)×100%

1.1.2 The Experimental Results are Shown in Table 2

TABLE 2

The inhibitory activity of part of the compounds at various concentrations on Lp-PLA$_2$ (rabbit serum as the source of enzyme)

| | Inhibitory ratio, % | | |
|---|---|---|---|
| Compound | 1 μM | 100 nM | 10 nM |
| Example 1 | 99.06 | 83.61 | 32.25 |
| Example 5 | 97.29 | 93.75 | 49.17 |
| Example 6 | 96.60 | 91.15 | 70.08 |
| Example 7 | 90.30 | 81.95 | 41.89 |
| Example 8 | 91.04 | 87.99 | 58.06 |
| Example 9 | 95.17 | 92.65 | 74.51 |
| Example 10 | 96.96 | 88.23 | 45.33 |
| Example 11 | 100 | 83.5 | 29.52 |
| Example 15 | 96.03 | 96.58 | 46.16 |
| Example 16 | 96.38 | 77.43 | 13.22 |
| Example 17 | 93.90 | 82.5 | 34.54 |
| Example 18 | NT | 80.62 | 40.59 |
| Example 19 | NT | 59.67 | — |
| Example 20 | NT | 54.17 | — |
| Example 21 | NT | 65.39 | 33.18 |
| Example 24 | NT | 63.59 | 35.91 |
| Example 25 | 96.57 | 92.07 | 47.54 |
| Example 26 | 93.45 | 57.30 | — |
| Example 27 | 94.46 | 88.82 | 34.43 |
| Example 29 | 97.09 | 83.46 | 22.58 |
| Example 34 | 95.62 | 54.15 | — |
| Example 65 | 95.08 | 77.36 | 32.32 |

"—" indicates no inhibitory activity;
"NT" indicates no test.

All the compounds listed in Table 2 had a Lp-PLA$_2$ inhibitory ratios of greater than 50% at the concentration of 100 nM, wherein the compounds in example 6 and example 9 showed the best activity in vitro in rabbit serum and their Lp-PLA$_2$ inhibitory ratios reached 70% at the concentration of 10 nM.

1.2 Determination of the Inhibitory Activity of the Compounds on Lp-PLA$_2$ (Human Recombinant Enzyme as the Source of Enzyme) (In Vitro)

1.2.1 Experiment Methods

1) The corresponding reagents were added according to Table 3 and mixed uniformly by shaking.

TABLE 3

The list of the reaction system

| | blank well | sample well | control well |
|---|---|---|---|
| reaction buffer | 30 μL | 20 μL | 20 μL |
| human recombinant enzyme (the source of enzyme) | | 10 μL | 10 μL |
| DMSO | 10 μL | | 10 μL |
| sample (in DMSO) | | 10 L | |

2) 10 μL of DTNB was added to each well.
3) 150 μL of 2-thio-PAF was added to each well and shaken for 15 s on a microplate reader to mix the liquid in the well uniformly. The detection was carried out at 414 nM over 10 minutes, once per minute and the slope was measured. The inhibitory ratio was calculated according to the following formula:

inhibitory ratio=1−(the slope of the sample well−the slope of the blank well)/(the slope of the control well−the slope of the blank well)×100%

1.2.2 The Experimental Results are Shown in Table 4

TABLE 4

The inhibitory activity of part of the compounds on Lp-PLA$_2$ (human recombinant enzyme as the source of enzyme)

| | inhibitory ratio, % | |
|---|---|---|
| compound number | 100 nM | 10 nM |
| Example 1 | 84.91 | 48.52 |
| Example 5 | 100 | 92.43 |
| Example 6 | 100 | 89.13 |
| Example 7 | 94.15 | 57.14 |
| Example 8 | 95.67 | 66.63 |
| Example 9 | 96.55 | 83.11 |
| Example 10 | 100 | 86.23 |
| Example 11 | 93.17 | 79.14 |
| Example 15 | 100 | 77.03 |
| Example 16 | 92.41 | 55.33 |
| Example 17 | 96.03 | 63.92 |
| Example 18 | 80.1 | 91.95 |
| Example 19 | 89.74 | 53.63 |
| Example 20 | 90.40 | 46.94 |
| Example 21 | 90.06 | 82.83 |
| Example 24 | 95.55 | 89.77 |
| Example 25 | 100 | 89.21 |
| Example 27 | 100 | 90.65 |
| Example 31 | 91.46 | 49.16 |
| Example 32 | 84.47 | 43.85 |

TABLE 4-continued

The inhibitory activity of part of the compounds on Lp-PLA$_2$ (human recombinant enzyme as the source of enzyme)

| compound number | inhibitory ratio, % | |
|---|---|---|
| | 100 nM | 10 nM |
| Example 33 | 92.86 | 78.84 |
| Example 34 | 95.62 | 53.88 |
| Example 65 | 97.13 | 75.36 |

"—" indicates no inhibitory activity;
"NT" indicates no test.

All the compounds listed in Table 4 had a Lp-PLA$_2$ inhibitory ratio of greater than 50% at a concentration of 10 nM, wherein the compounds in examples 5, 6, 10, 18, 24, 25 and 27 showed the best activity in vitro in human recombinant enzymes, and their Lp-PLA$_2$ inhibitory ratios reached about 90% at the concentration of 10 nM.

1.3 Determination of the Inhibitory Activity of the Compounds on Lp-PLA$_2$ (Rat Serum as the Source of Enzyme (In Vitro)

1.3.1 Experiment Methods

1) The corresponding reagents were added according to Table 5 and mixed uniformly by shaking.

TABLE 5

The list of the reaction system

| | blank well | sample well | control well |
|---|---|---|---|
| reaction buffer | 30 μL | 20 μL | 20 μL |
| rat serum (the source of enzyme) | | 10 μL | 10 μL |
| DMSO | 10 μL | | 10 μL |
| sample (in DMSO) | | 10 L | |

2) 10 μL of DTNB was added to each well.
3) 150 μL of 2-thio-PAF was added to each well and shaken for 15 s on a microplate reader to mix the liquid in the well uniformly. The detection was carried out at 414 nM over 10 minutes, once per minute and the slope was measured. The inhibitory ratio was calculated according to the following formula:

inhibitory ratio=1−(the slope of the sample well−the slope of the blank well)/(the slope of the control well−the slope of the blank well)×100%

1.3.2 The Experimental Results are Shown in Table 6

TABLE 6

The inhibitory activity of part of the compounds on Lp-PLA$_2$ (rat serum as the source of enzyme)

| control number | inhibitory ratio, % | | |
|---|---|---|---|
| | 1 μM | 100 nM | 10 nM |
| Example 1 | 100 | 64.69 | 11.84 |
| Example 5 | NT | 73.23 | 18.21 |
| Example 6 | NT | 86.85 | 38.66 |
| Example 8 | 77.05 | 67.55 | 18.97 |

TABLE 6-continued

The inhibitory activity of part of the compounds on Lp-PLA$_2$ (rat serum as the source of enzyme)

| control number | inhibitory ratio, % | | |
|---|---|---|---|
| | 1 μM | 100 nM | 10 nM |
| Example 9 | 89.94 | 83.24 | 42.03 |
| Example 10 | NT | 82.5 | 22.5 |
| Example 11 | 100 | 83.50 | 29.52 |
| Example 15 | NT | 78.94 | 23.09 |
| Example 16 | NT | 50.35 | 6.84 |
| Example 17 | NT | 50.55 | 13.86 |
| Example 18 | NT | 91.69 | 27.75 |
| Example 19 | NT | 18.06 | — |
| Example 20 | NT | 43.27 | — |
| Example 21 | NT | 82.48 | 27.65 |
| Example 24 | NT | 100 | 71.86 |
| Example 25 | NT | 100 | 60.04 |
| Example 27 | NT | 100 | 94.11 |
| Example 65 | 100 | 81.68 | 33.51 |

"—" indicates no inhibitory activity;
"NT" indicates no test.

All the compounds listed in Table 6, except the compounds of Example 19 and Example 20, had a Lp-PLA$_2$ inhibitory ratio of greater than 50% at the concentration of 10 nM, wherein the compound in example 27 showed the best activity in vitro in rat serum and its Lp-PLA$_2$ inhibitory ratio exceeded 90% at the concentration of 10 nM.

Example 2: In Vivo Inhibition Assay of Lp-PLA$_2$ Activity in SD Rats

2.1 Experimental Method

Each group had 5 SD rats and 50 mg/kg test agents was administrated orally to the rats. Darapladib was dissolved in ddH2O, and the other compounds were dissolved in sodium carboxymethyl cellulose (CMC sodium). Blood was collected from the orbits of the rats at 0 h before administration and at 1 h, 3 h, 5 h, 7 h and 24 h after administration and placed at room temperature for 30 minutes before centrifugation. Serum was collected and the Lp-PLA$_2$ activity in serum was measured.

2.2 Experimental Results

Figure 2:
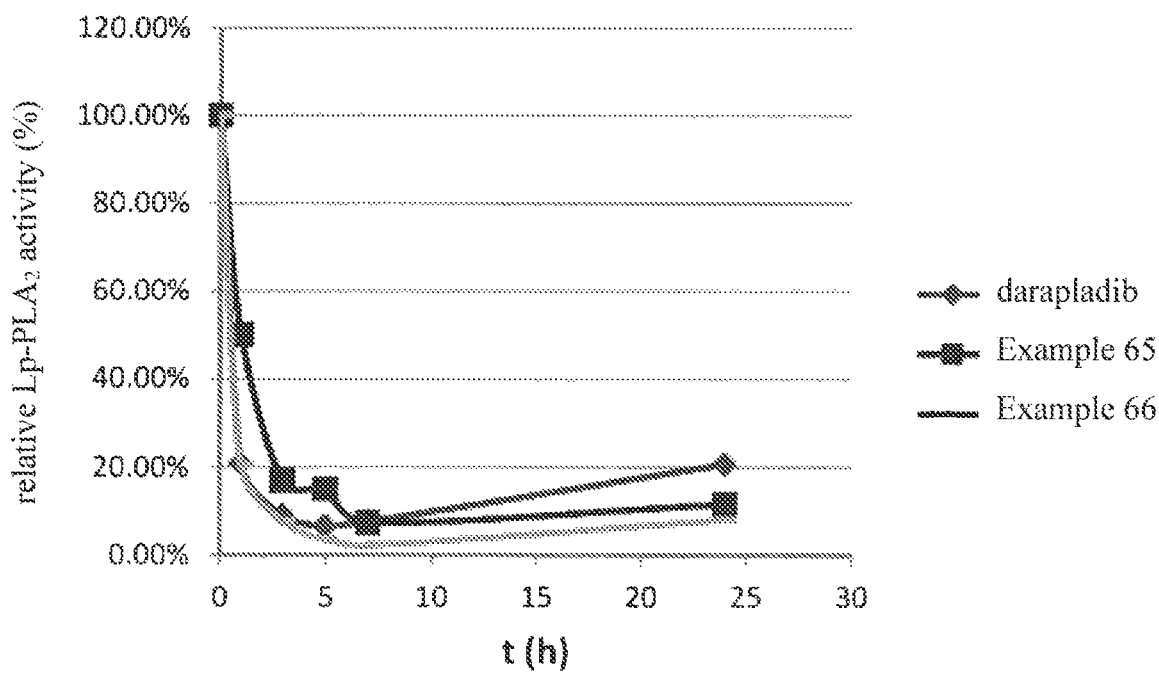
FIG. 2 shows the activity of Lp-PLA$_2$ in the serum of SD rats after single administration.

According to the results of the in vitro activity assays, part of the compounds was selected for an in vivo test of the Lp-PLA$_2$ inhibitory activity in SD rats. The experimental results were shown in FIG. 1 and FIG. 2.

The results showed that the selected compounds were able to significantly inhibit the activity of Lp-PLA$_2$ in serum of the SD rats after a single administration, wherein the compounds of example 27 (50 mg/kg), example 65 (50 mg/kg), and example 66 (50 mg/kg) showed in vivo activities comparable to darapladib (50 mg/kg), a Lp-PLA$_2$ inhibitor currently under Phase III clinical trials. The in vivo experimental results showed that the orally administered example compounds exhibited a remarkable Lp-PLA$_2$ inhibitory activity in rats, indicating that the example compounds have a promising prospect for development.

Example 3: In Vitro Assay of S9 Metabolic Stability

3.1. Reagents

3.1.1 The Preparation of Tris/HCl(0.1 M, pH 7.4) Buffer 12.12 g of TRIS (tris-hydroxymethyl aminomethane) was weighed, dissolved in 800 mL of water, and adjusted to pH 7.4 with HCl (2 M), and then the volume was adjusted to 1000 mL with water.

3.1.2 The Preparation of MgCl$_2$

MgCl$_2$ (100 mM) solution was prepared with 0.1 M Tris/HCl buffer, aliquoted and stored at −20° C. The incubation concentration of MgCl$_2$ was 5.0 mM.

3.1.3 The Preparation of NADPH

NADPH (10 mM) solution was prepared with 0.1 M Tris/HCl buffer, aliquoted and stored at −20° C. The incubation concentration of NADPH was 1.0 mM.

3.1.4 The Preparation of S9

Human S9 (purchased from Reid Liver Disease Research (Shanghai) Co., Ltd.) was diluted 10 times with 0.1 M Tris/HCl and rat S9 (purchased from Reid Liver Disease Research (Shanghai) Co., Ltd.) was diluted 5 times with 0.1 M Tris/HCl, so that the incubation concentrations of human and rat S9 were equivalent to the incubation concentrations of the liver microsomes in the corresponding species (both incubation concentrations of liver microsomes in human and rats are 0.33 mg/mL).

3.1.5 The Preparation of the Compounds to be Tested

The compound was dissolved in DMSO to obtain a stock solution at a concentration of 10 mM. The stock solution was diluted to 1 mM with DMSO and then diluted with 0.1% BSA-water to obtain a working solution at a concentration of 2 μM. In the incubation system, the working solution of 2 μM was diluted 20 times to a final concentration of 0.1 μM. The concentration of DMSO in the incubation system was <0.01%.

3.1.6 The Preparation of the Positive Control Compound 2 mM VIVID stock solution (purchased from Shanghai Beili Biotechnology Co., Ltd.) was diluted 50 times with the 2 μM working solution for the compounds to be tested. In the incubation system, the mixed working solution of VIVID and the compounds to be tested were diluted 20 times

3.2 Experimental Method

S9 was incubated in a 96-well plate and each incubation system was 450 μL. 0.1 M Tris buffer (pH 7.4), MgCl$_2$, S9 and +NADPH/−NADPH were pre-incubated at 37° C. for 10 min (600 rpm), and then the reaction was initiated by adding a compound to be tested. The same volume of glacial methanol was added to terminate the reaction after 0, 7, 17, 30 and 60 minutes, respectively.

3.3 The Experimental Results Were Shown in Table 7

TABLE 7

The metabolic stability of part of the compounds in human and rat S9

| Compound number | Tested species | Reductive coenzyme II (NADPH) | Half life (min) |
|---|---|---|---|
| Example 1 | human | addition | — |
| Example 1 | rat | addition | 1217 |
| Example 6 | human | addition | 563 |
| Example 6 | rat | addition | 149 |
| Example 11 | human | addition | 457 |
| Example 11 | rat | addition | 46 |
| Example 12 | human | addition | 233 |
| Example 12 | rat | addition | 90 |
| Example 17 | human | addition | — |
| Example 17 | rat | addition | 160 |
| Example 21 | human | addition | — |
| Example 21 | rat | addition | 11692 |
| Example 24 | human | addition | 592 |
| Example 24 | rat | addition | 285 |
| Example 25 | human | addition | 415 |
| Example 25 | rat | addition | 251 |
| Example 65 | human | addition | 425 |
| Example 65 | rat | addition | 161 |

"—" indicates that the compound was stable in the test system and its half-life was unable to be measured.

The experimental results show that all the compounds listed in table 7 have a good metabolism stability, and furthermore, the metabolism stabilities in human and rat were in a similar trend, which indicates a good species consistency. Some of the compounds such as the compounds in example 1, example 21, example 24, and example 25 showed a superior metabolism stability.

Example 4: Effect on Retinal Thickness of STZ-Induced Diabetic Rats

4.1 Experimental Purpose

The effect of the example compounds on retinopathy of STZ-induced diabetic rats was observed.

4.2 Test Medicaments

Test compound: The compounds of example 11 and example 27 were dissolved in 0.25% CMC-Na.
Positive control: Darapladib, dissolved in ultrapure water.

4.3 Test Animals

Varieties: commercially available SD rats; grade: SPF grade; gender: male; weight 180~220 g.

4.4 Grouping and Administration

The compounds of examples 11 and 27 and darapladib were administered orally to the two animal groups of administration at a dose of 25 mg/kg/day, and the administration period was 4 weeks.

4.5 Test Methods

4.5.1 Establishment of the Diabetic Rat Model

All SD rats were preconditioned for 3-5 days. Except for the normal control group, all the other rats were injected intraperitoneally with STZ. The specific method of model establishment was as follows: fasting rats (fasting for 16 h, free to drink water) were weighed and injected with 50 mg/kg of STZ through tail vein to build the diabetic rat model. STZ was prepared with 10 mM pH 4.6 sodium citrate buffer (freshly prepared on site, placed on ice, kept at low temperature to avoid STZ volatilization). 7 days after injection and after 10 h of fasting, the blood was collected from the rat submandibular vein and the blood glucose was measured.

The diabetic model was established when the blood glucose of the rats was more than 10 mmol/L.

4.5.2 Grouping and Administration

Twenty diabetic rats whose blood glucose values were more than 10 mmol/L and close to the average value were selected and grouped by stratified randomization into the following 4 groups according to the blood glucose value: model control group, the compound of example 11, the compound of example 27 and darapladib positive control group and each group had 5 rats. The rats were administrated once a day. Another 5 rats without injection of STZ were used as normal control group.

4.6 Observation Indexes

4.6.1 Determination of the Lp-PLA$_2$ Activity

The activity of LP-PLA$_2$ in serum was measured before administration, at 3 h and 24 h after administration on the first day, at 24 h after administration on the second day, at 2 weeks and at 4 weeks after administration.

4.6.2 Measurement of Retinal Thickness

The eyeballs of the rats were removed, frozen and sectioned and the thickness of each slice was 8 μm. The slice was stained with conventional hematoxylin/eosin and photographed with a 400-fold optical microscope (Eclipse 80i, Nikon). The thickness of the retina was analyzed using the software Image-Pro plus 6.0. Five points were selected in each photo.

4.7 Statistical Analysis

Statistical analysis was performed with the EXCEL 2007 software. All data were expressed as mean±standard error ($\bar{x}$ ±SEM). The experiment results were evaluated by Student T test.

4.8 Experimental Results

Figure 3:
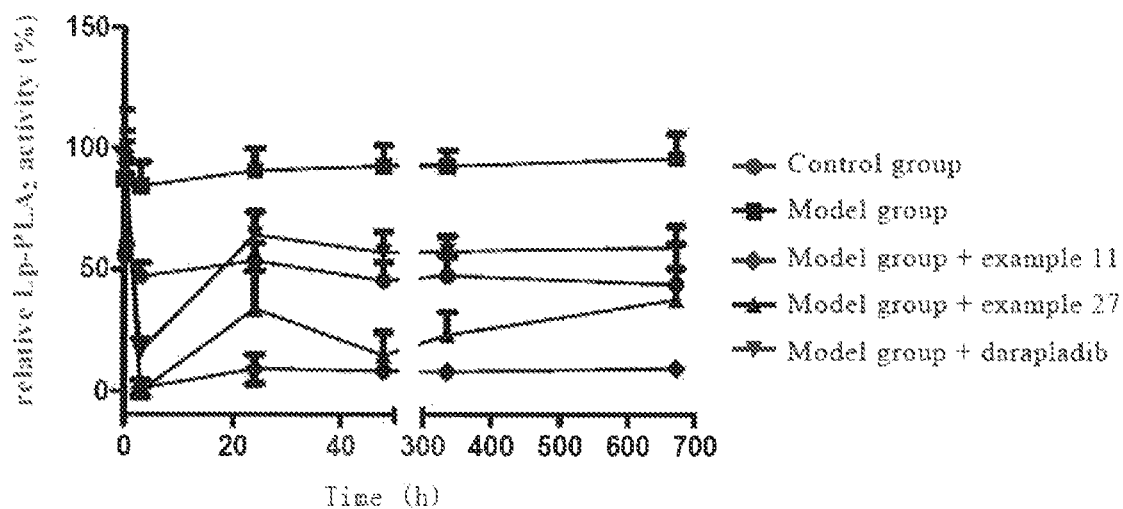
FIG. 3 shows the in vivo activity of Lp-PLA$_2$ in the serum of STZ-induced diabetic rats after long-term administration.

4.8.1 Effects of Compounds on Serum Lp-PLA$_2$ Activity in STZ-Induced Diabetic Rats It can be seen from FIG. 3 that the in vivo serum Lp-PLA$_2$ activity of the diabetic rats in the model control group was significantly higher compared with the normal control group. Compared with the model control group, the in vivo serum Lp-PLA$_2$ activity of the rats in groups of the example 11 compound, the example 27 compound and darapladib were all decreased significantly at 3 hours, 24 hours, 48 hours, 2 weeks and 4 weeks after administration. The experiment results showed that the compounds of example 11 and example 27 administered orally for a long term can continuously and effectively inhibit the activity of serum Lp-PLA$_2$ in rats.

Figure 4:
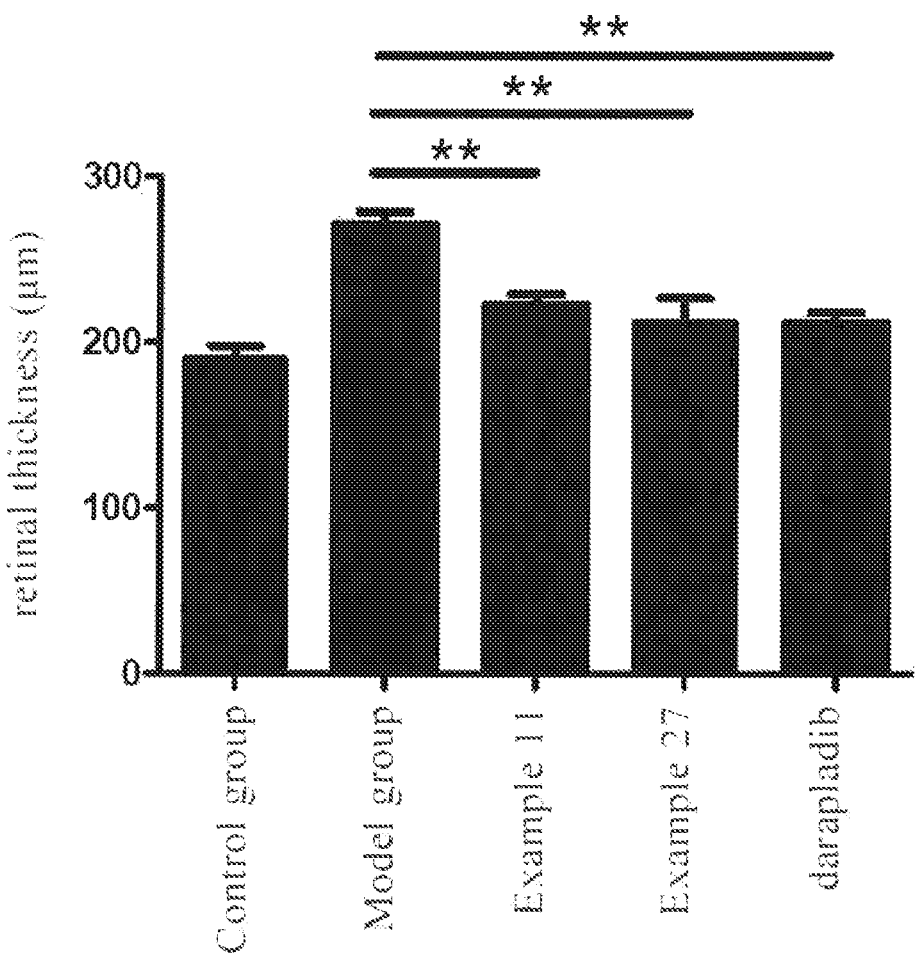
FIG. 4 shows the retinal thickness changes of STZ-induced diabetic rats after long-term administration.

4.8.2 Effects of Compounds on Retinal Thickness of STZ-Induced Diabetic Rats As can be seen from FIG. 4, compared with the normal control group, the thickness of the retina of the diabetic rats in model control group were significantly increased. Compared with the model control group, the retinal thickness of the rats in the example 11 compound group, the example 27 compound group and the darapladib group were significantly decreased. STZ-induced diabetic rats are considered to be an effective animal model of diabetic macular edema, wherein long-term hyperglycemia leads to dysfunction of the blood retinal barrier and increased barrier permeability, which in turn leads to the consequence that entrance of the fluid and protein from the peripheral blood into the retina cannot be strictly controlled, and once the fluid and protein of the peripheral blood accumulate in the retinal parenchyma, it will lead to edema of the retina, which is pathologically manifested as the increase of the retinal thickness. Thus, the experimental data showed that the compound of example 11 and the compound of example 27 have a promising prospect to be used for the treatment of diabetic macular edema.

Example 5: Effect of the Administration of the Example Compound on Spontaneous Type 2 Diabetes ZDF Rats

5.1 Experimental Purpose

The effect of long-term administration of the compound of example 11 on blood glucose and other biochemical indexes of spontaneous type 2 diabetic obese rats (ZDF) were observed.

5.2 Test Drug

Test compound: The compound of Example 11, dissolved in 0.25% CMC-Na.
Positive control: metformin, produced by China-US Shanghai Squibb Pharmaceutical Co., Ltd.; dissolved in ultra-pure water.

5.3 Test Animal

Varieties: ZDF rats, ZL rats; Grade: SPF grade; Age: 56-62 days; Gender: Male; Source: Beijing Weitong Lihua Experimental Animal Co., Ltd.

5.4 Reagents and Instruments

The kits for total cholesterol (TC), triglyceride (TG), high density lipoprotein cholesterol (HDL-C), low density lipoprotein cholesterol (LDL-C), blood glucose (GLU), aspartate transferase (AST), alanine aminotransferase (ALT), alkaline phosphatase (ALP), urea (BUN), creatinine (CREA) and the like were purchased from Shanghai Shenneng Desai Diagnostic Technology Co., Ltd. The reagents for glycosylated hemoglobin (HbA1c) assay was purchased from Trinity Biotech Corporation. Insulin ELISA Assay Kit was purchased from BertinPharma Corporation. Urine microalbumin (mALB) and other ELISA kits were purchased from Nanjing Jiancheng Bioengineering Institute.

5.5 Grouping and Administration

Two ZDF rat groups were orally administered with the compound of example 11 and metformin, respectively. The dose of the compound of example 11 was 25 mg/kg/day for the first 4 days and adjusted to 10 mg/kg/day afterwards. The dose of metformin was 300 mg/kg/day. Both were administered for a period of 6 weeks.

5.6 Test Methods

5.6.1 Animal Screening

Thirty male ZDF rats (56~62 days old) were fed with Purina #5008 feed (purchased from Nongbiao Purina Feed Co., Ltd.) and the other 6 ZL rats were fed with normal diet as normal control. After fed for 2 weeks, the empty body weights of the fasting rats (fasting for 10 h, free to drink water) were weighed. 0.3 mL blood was collected through tail vein and placed in EDTA anticoagulant tube for the determination of glycosylated hemoglobin (HbA1c). Another 0.5 mL blood was collected and centrifugated at 3000 rpm for 10 min to separate serum which then was determined by automatic biochemical analyzer Model 7020. The serum was separated and then blood glucose and blood lipid (GLU, TC, TG) and hepatorenal function (ALT, AST, ALP, BUN, CREA) were determined. The ZDF rats with blood glucose far from the mean value or having other abnormal indexes were removed and 18 ZDF rats with GLU close to the mean value were selected.

5.6.2 Grouping and Administration

Using the blood glucose value as the main indicator and also taking into account the glycosylated hemoglobin, insulin and other indicators, the 18 selected ZDF rats were evenly grouped by stratified randomization to the following groups: model control group, example 11 compound group, positive control group, 6 rats in each group. Rats in each group were given the corresponding drug or solvent by gavage through oral once a day in the morning for 6 continuous weeks. Another 6 ZL rats were taken as normal control group. During the period of administration, the model control group, the example 11 compound group and the positive control group were fed with Purina #5008 feed, and the normal control group was fed with normal feed.

5.6.3 Biochemical Testing

Every 2 weeks the rats were fasted but allowed free drinking for 10 h, the empty body weight was weighed and 0.5 mL blood was collected through the tail vein to determine the blood glucose levels. The levels of insulin, glycosylated hemoglobin and triglyceride were measured at the 4th week of administration and at the end of the administration. The levels of low density lipoprotein and high density lipoprotein were measured at the 6th week of administration. The urine samples were collected once before the end of the administration and 24 h (11:00 am to 11:00 am the next day) urine samples were collected to detect urinary albumin content in urine.

5.7 Statistical Analysis

Statistical analysis was performed with EXCEL 2007 software. All data were expressed as mean±standard error ($\bar{x}$ ±SEM). and the results were evaluated by Student T test.

5.8 Experimental Results

5.8.1 Blood Glucose Levels

Figure 5:
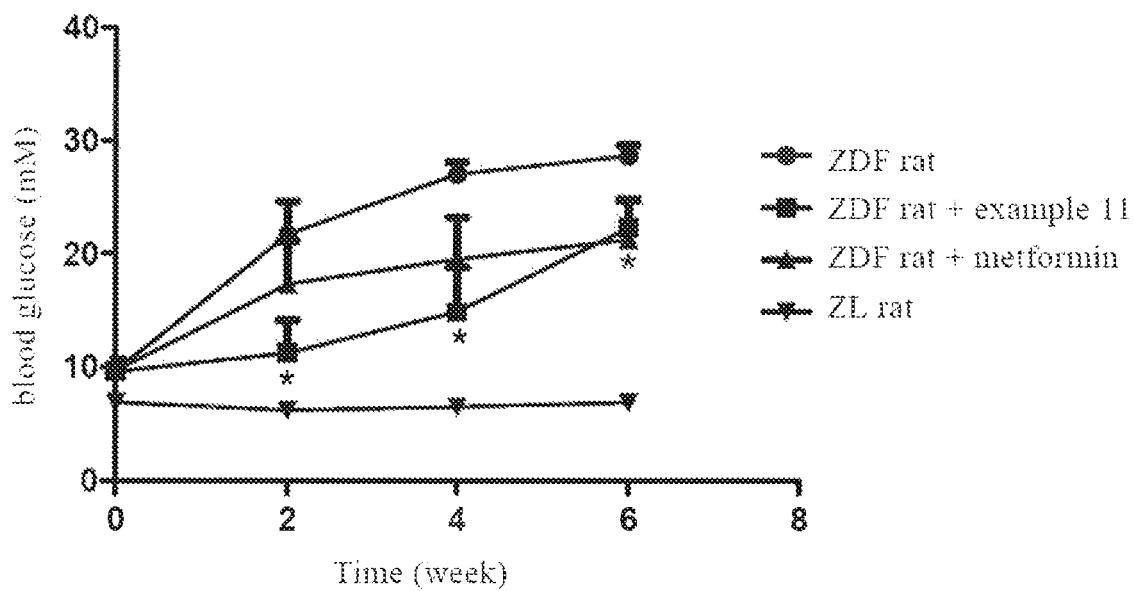
FIG. 5 shows the blood glucose changes of ZDF diabetic rats after long-term administration.

As can be seen from FIG. 5, compared with the normal control group, the blood glucose levels of the diabetic rats in the model control group were significantly increased. Compared with the model control group, the blood glucose level of the example 11 compound group was significantly decreased at 2 weeks, 4 weeks and 6 weeks after administration. The experimental results showed that long-term oral administration of the compound of example 11 was effective in significantly reducing blood glucose levels in ZDF rats.

5.8.2 Insulin Levels

Figure 6:
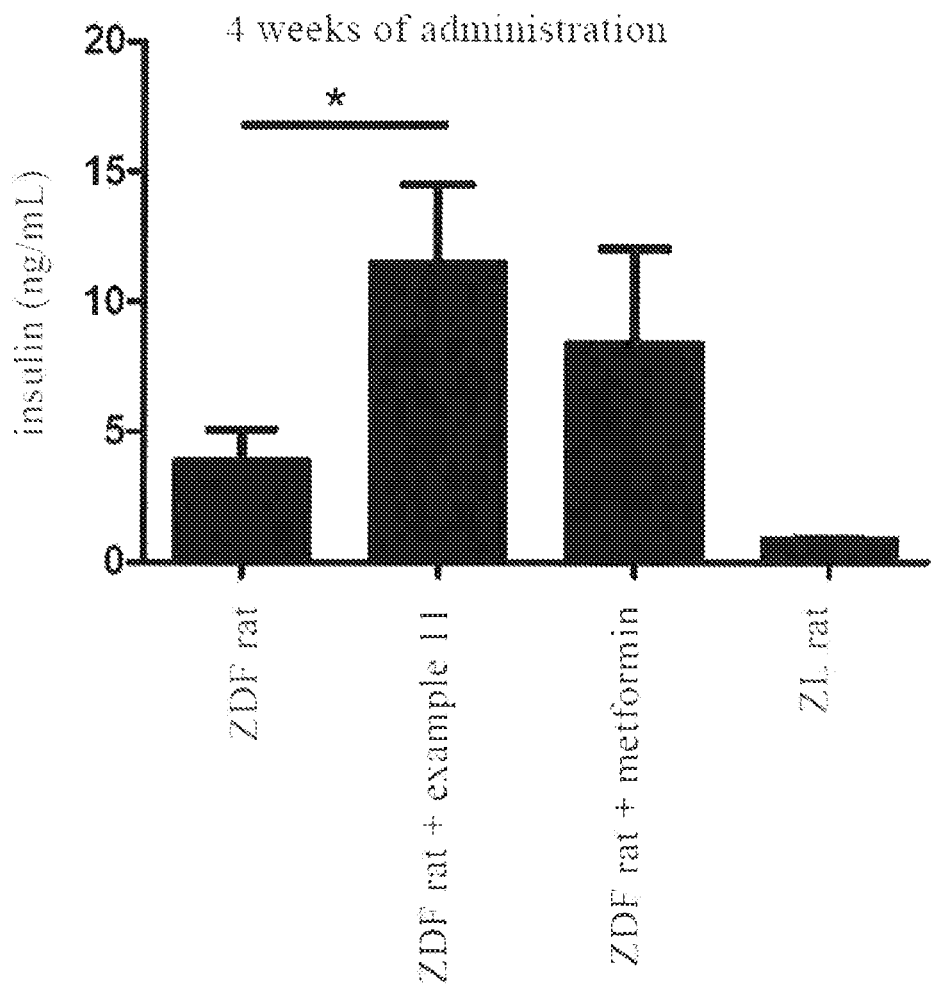
FIG. 6 shows the insulin levels changes of ZDF diabetic rats after 4 weeks of administration.
Figure 7:
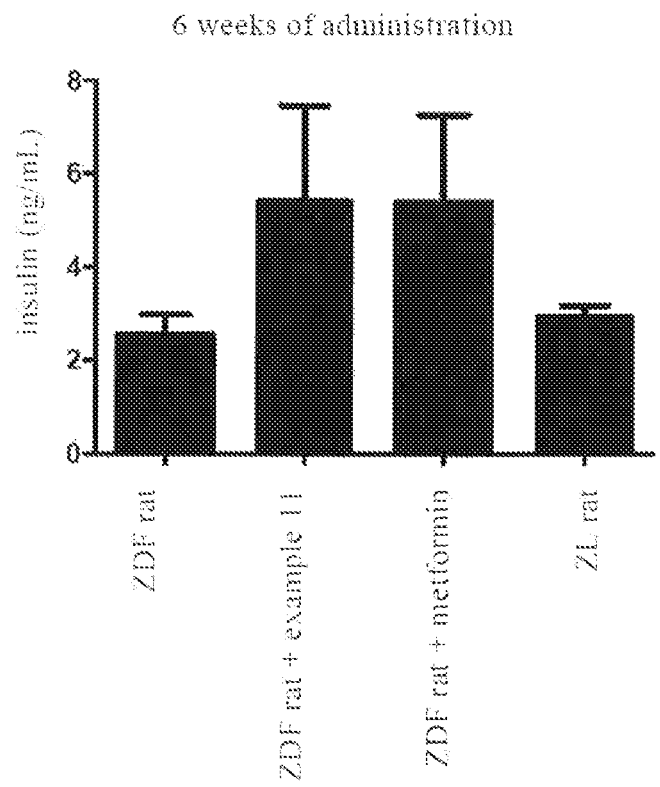
FIG. 7 shows the insulin levels changes of ZDF diabetic rats after 6 weeks of administration.

As can be seen from FIG. 6 and FIG. 7, compared with the model control group, the insulin level was significantly increased in the example 11 compound group at 4 weeks after the administration, and the insulin level was also remarkably increased at 6 weeks.

5.8.3 Glycosylated Hemoglobin

Figure 8:
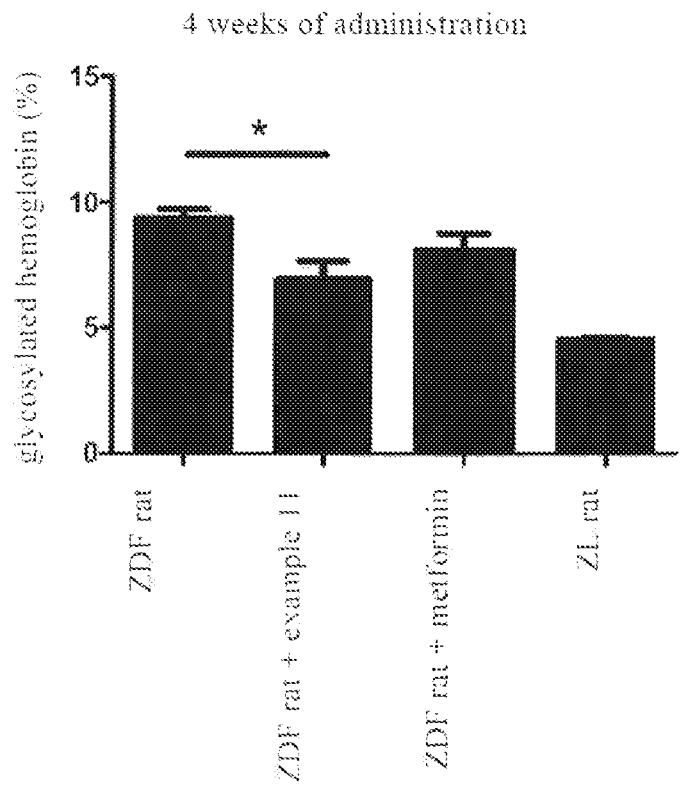
FIG. 8 shows the glycosylated hemoglobin level changes of ZDF diabetic rats after 4 weeks of administration.
Figure 9:
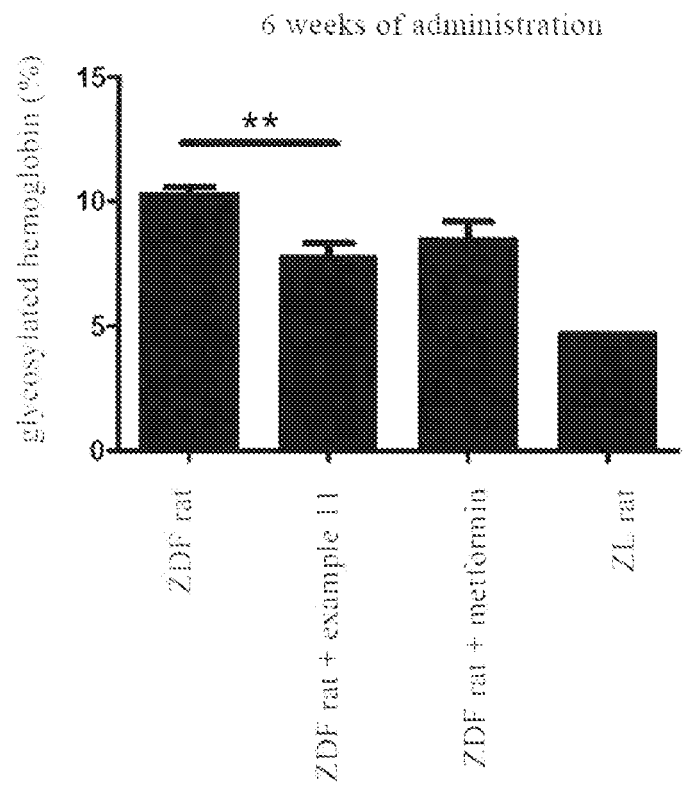
FIG. 9 shows the glycosylated hemoglobin level changes of ZDF diabetic rats after 6 weeks of administration.

As can be seen from FIG. 8 and FIG. 9, the Example 11 compound group had significantly reduced glycosylated hemoglobin levels at 4 weeks and 6 weeks after the administration compared to the model control group.

5.8.4 Triglyceride Levels

Figure 10:
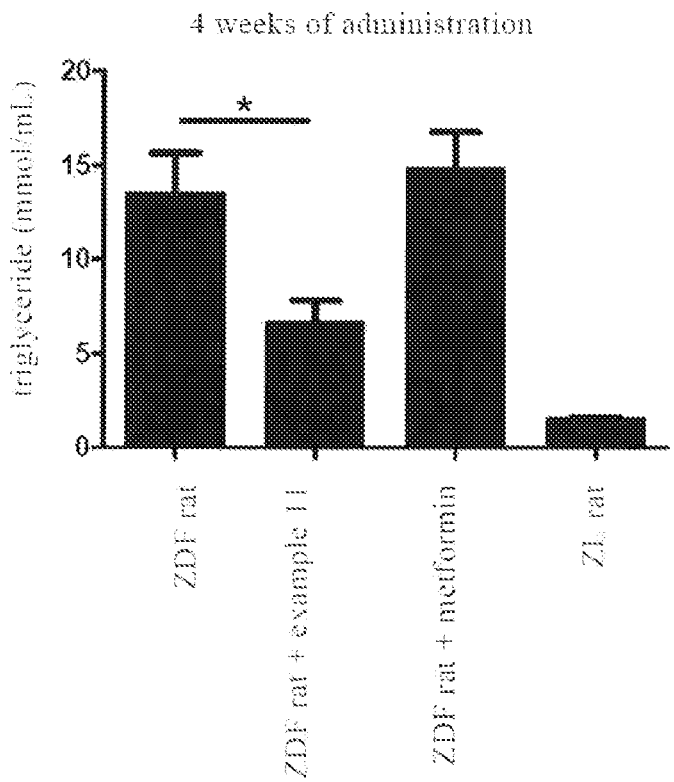
FIG. 10 shows the triglyceride level changes of ZDF diabetic rats after 4 weeks of administration.
Figure 11:
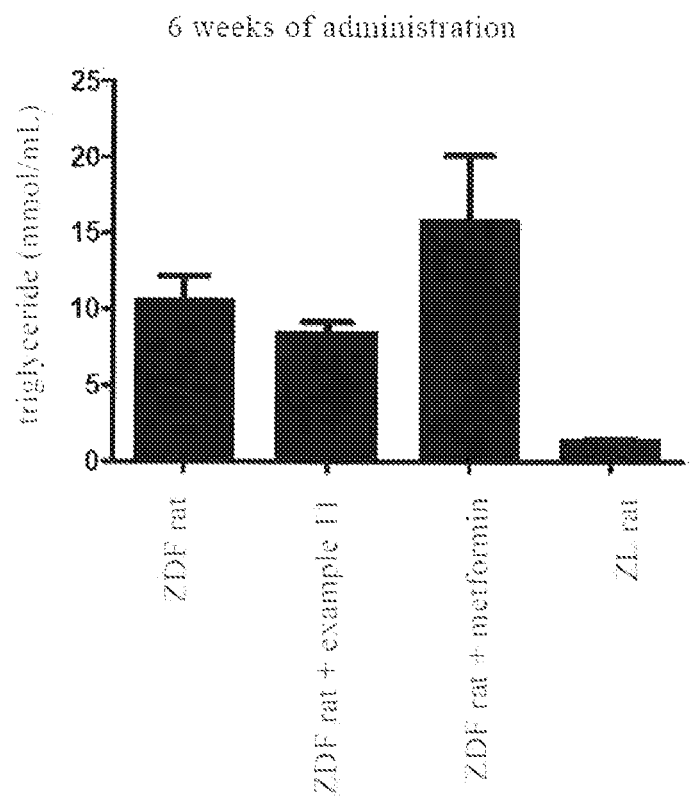
FIG. 11 shows the triglyceride level changes of ZDF diabetic rats after 6 weeks of administration.

As can be seen from FIG. 10 and FIG. 11, the triglyceride level of the example 11 compound group was significantly decreased compared with that of the model control group at 4 weeks after the administration.

5.8.5 Low Density Lipoprotein and High Density Lipoprotein

Figure 12:
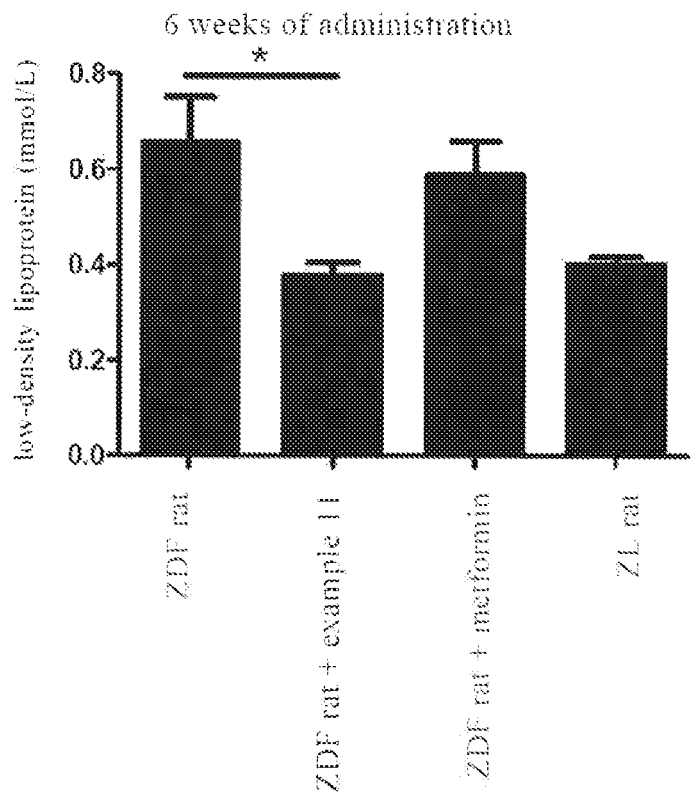
FIG. 12 shows the low-density lipoprotein level changes of ZDF diabetic rats after 6 weeks of administration.
Figure 13:
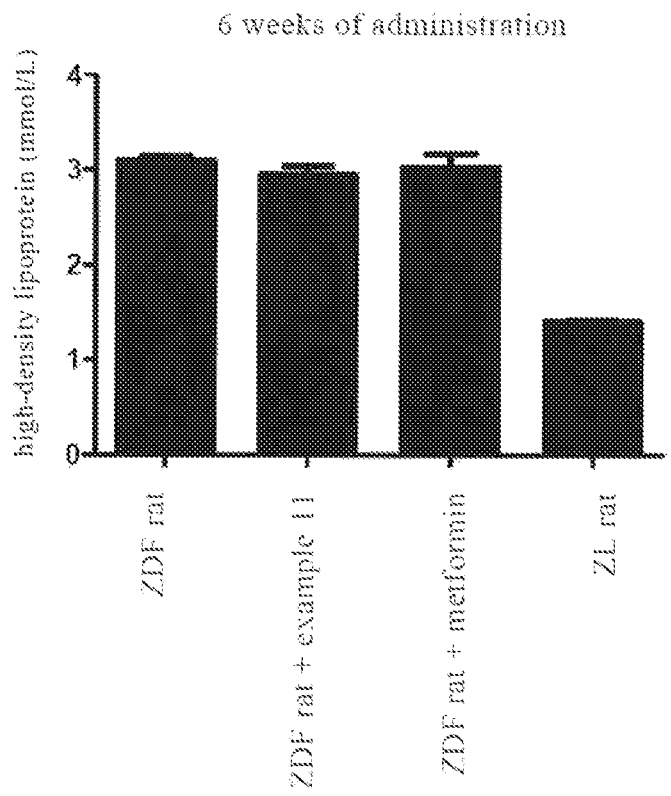
FIG. 13 shows the high-density lipoprotein level changes of ZDF diabetic rats after 6 weeks of administration.

As can be seen from FIG. 12, the level of low-density lipoprotein of the example compound group was significantly reduced compared with that of the model control group at 6 weeks after the administration. As can be seen from FIG. 13, there was no significant change in the high-density lipoprotein level in the example 11 compound group at 6 weeks after the administration compared with that in the model control group.

5.8.6 Urinary Albumin

Figure 14:
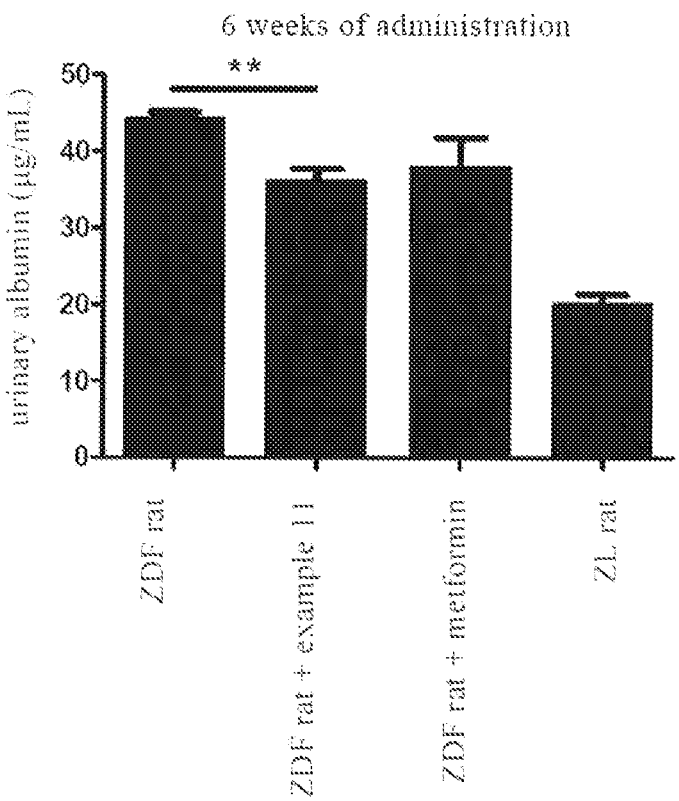
FIG. 14 shows the urinary albumin level changes in urine of ZDF diabetic rats after 6 weeks of administration.

As can be seen from FIG. 14, the urinary albumin levels in the urine of the example 11 compound group were significantly reduced at 6 weeks after the administration compared with that in the model control group.

5.9 Summary of Experimental Results

The experimental results demonstrate that tong-term administration of the example 11 compound can significantly reduce the level of blood glucose in spontaneous type 2 diabetic ZDF rats, significantly lower the level of glycosylated hemoglobin and up-regulate the level of insulin, indicating that the compound of example 11 has an excellent prospect for the treatment of diabetes.

In addition, long-term administration of the example 11 compound can significantly down-regulate the level of triglyceride and the level of low-density lipoprotein in spontaneous type 2 diabetic ZDF rats without significant effect on high density lipoprotein, indicating that the compound of example 11 has an excellent prospect for dyslipidemia, such as atherosclerosis.

Finally, long-term administration of the example 11 compound can significantly down-regulate urinary albumin level in the urine of spontaneous type 2 diabetic ZDF rats, indicating that the compound of example 11 has a promising prospect for kidney diseases, such as diabetic nephropathy.

All documents mentioned in the present invention are incorporated herein by reference, as if each document were individually recited for reference. It is also to be understood that those skilled in the art can make various changes or modifications to the present invention upon reading of the above teachings of the present invention, and these equivalents also fall within the scope of the appended claims.

What is claimed is:

1. A method of treating and/or alleviating diabetes and diabetic complications in a subject, comprising administering to the subject an effective amount of a compound of general formula I, a deuterated form, a stereoisomer or pharmaceutically acceptable salt thereof:

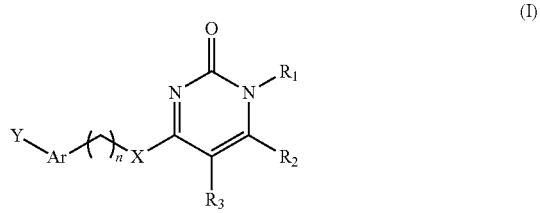

(I)

wherein, $R_1$ is selected from the group consisting of $C_1$-$C_6$ alkyl, —$(CH_2)_q$-(3-8 membered heteroaryl);
$R_2$ is $C_1$-$C_6$ alkyl, 3-8 membered heterocyclic radical, $C_1$-$C_6$ alkoxy, $C_6$-$C_{10}$ aryl, —$(CH_2)_m$-(3-8 membered heteroaryl) or —$NR_4R_5$;
$R_3$ is H;
X is O, S, or —$N(R_4)$—;
n is 1, 2, 3 or 4;
Ar is an phenyl ring optionally substituted with a group selected from the group consisting of: —CN, =O, $C_1$-$C_6$ alkyl, $C_6$-$C_{10}$ aryl, $C_1$-$C_6$ alkoxy, $C_3$-$C_8$ cycloalkyl, halogen, and halo-$C_1$-$C_6$ alkyl;
Y is absent, -A-($C_6$-$C_{10}$ aryl) or -A-(3-8 membered heteroaryl), wherein, A is O or S,
wherein,
said $C_1$-$C_6$ alkyl, $C_1$-$C_6$ alkoxy, 3-8 membered heteroaryl, 3-8 membered heterocyclic radical, $C_6$-$C_{10}$ aryl are optionally substituted with a group selected from the group consisting of: —CN, =O, $C_1$-$C_6$ alkyl, $C_6$-$C_{10}$ aryl, $C_1$-$C_6$ alkoxy, $C_3$-$C_8$ cycloalkyl, halogen, halo-$C_1$-$C_6$ alkyl;
each $R_4$ and each $R_5$ are independently selected from the group consisting of H, $C_1$-$C_6$ alkyl, —$(CH_2)_{m1}$—($C_1$-$C_6$ alkoxy), $C_3$-$C_8$ cycloalkyl;
m is 0, 1, 2, 3 or 4; and
m1 is independently 1, 2, 3 or 4.

2. The method according to claim 1, wherein said compound of general formula I has one or more of the following features:

(1) $R_1$ is $C_1$-$C_3$ alkyl;
(2) $R_3$ is H;
(3) n is 1 or 2; and
(4) X is O.

3. The method according to claim 1, wherein $R_2$ is $C_1$-$C_6$ alkyl, 3-8 membered heterocyclic radical, $C_1$-$C_6$ alkoxy, $C_6$-$C_{10}$ aryl, —$(CH_2)_m$-(3-8 membered heteroaryl) or —$NR_4R_5$, wherein,
said 3-8 membered heterocyclic radical, $C_1$-$C_6$ alkoxy, $C_6$-$C_{10}$ aryl, —$(CH_2)_m$-(3-8 membered heteroaryl) are optionally substituted with a group selected from the group consisting of: $C_1$-$C_6$ alkyl, $C_1$-$C_6$ alkoxy, $C_3$-$C_8$ cycloalkyl, halogen, said m is 0;
$R_4$ and $R_5$ are independently selected from the group consisting of H, $C_1$-$C_6$ alkyl, —$(CH_2)_{m1}$—($C_1$-$C_6$ alkoxy), $C_3$-$C_8$ cycloalkyl; wherein
m1 is 2 or 3.

4. The method according to claim 1, wherein said compound of general formula I has one or two of the following features:

(1) Ar is substituted or unsubstituted phenyl, wherein said substitution means that the phenyl has 1-4 substituents selected from the group consisting of: —CN, $C_1$-$C_6$ alkyl, halogen, hydroxyl, halo-$C_1$-$C_6$ alkyl, and halo-$C_1$-$C_6$ alkoxy;
(2) Y is -A-($C_6$-$C_{10}$ aryl) or -A-(5-6 membered heteroaryl), wherein, A is O or S; said $C_6$-$C_{10}$ aryl or 5-6 membered heteroaryl optionally has 1-3 substituents selected from the group consisting of: $C_1$-$C_4$ alkyl, —CN, halogen, halo-$C_1$-$C_6$ alkyl.

5. The method according to claim 1, wherein said compound of general formula I is:

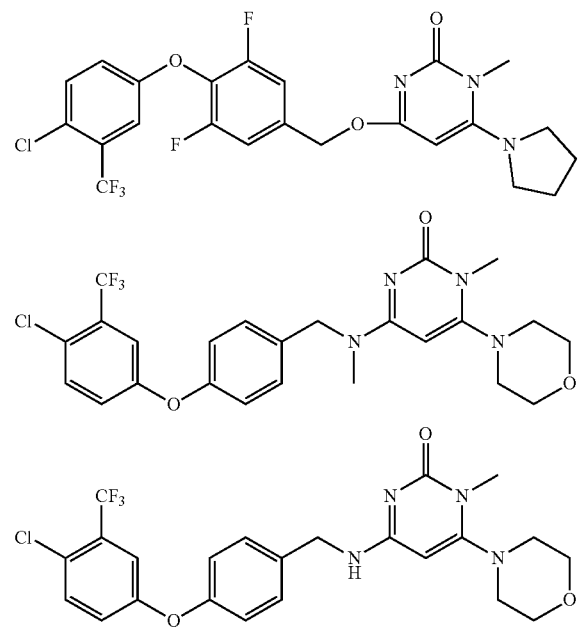

89
-continued
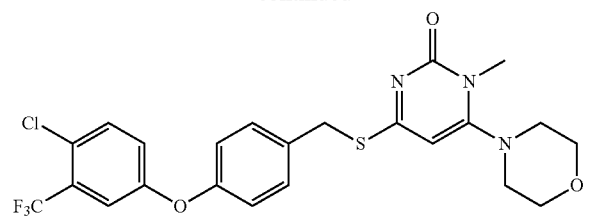
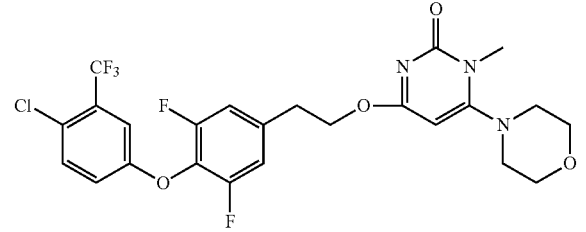
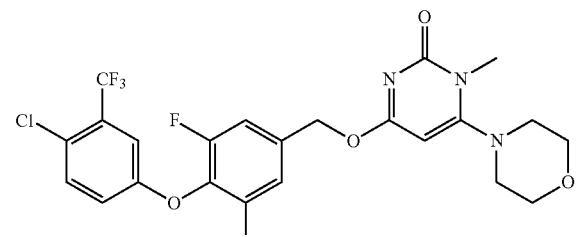
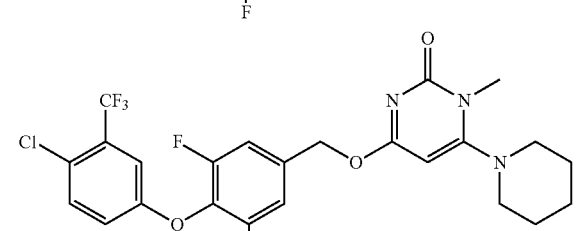
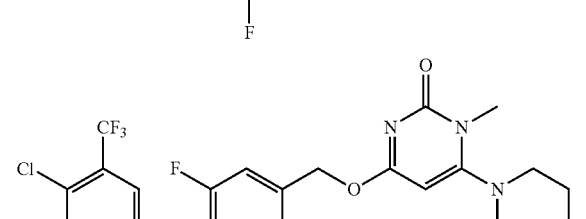
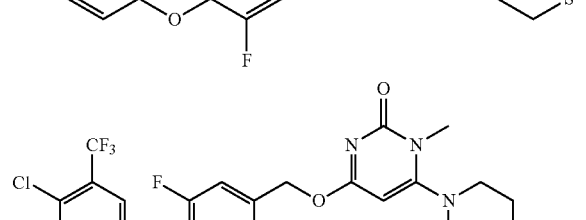
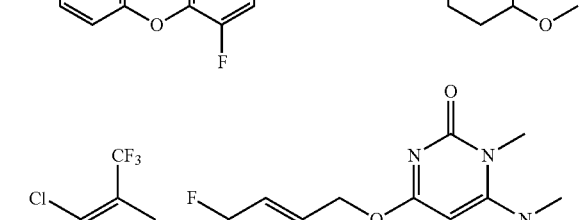
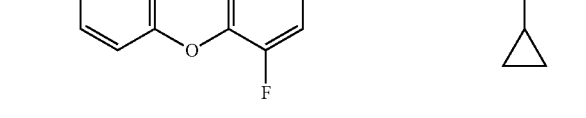
90
-continued
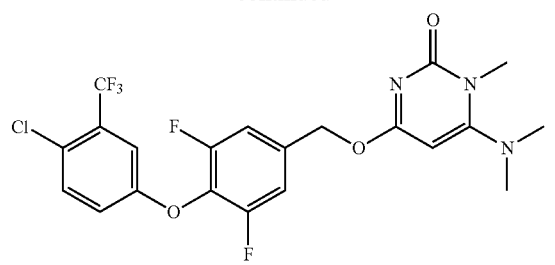
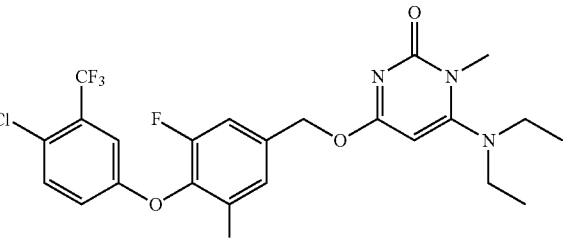
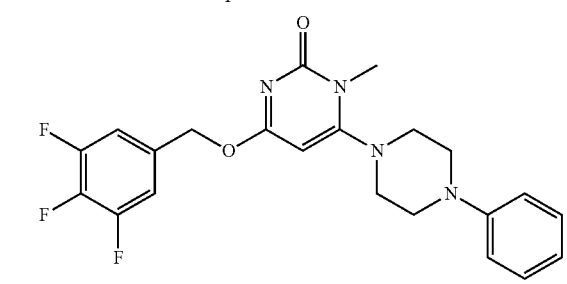
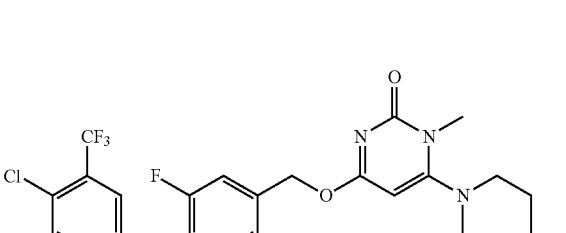
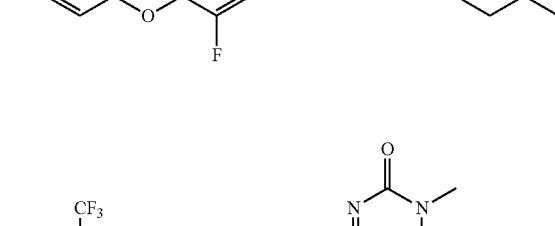
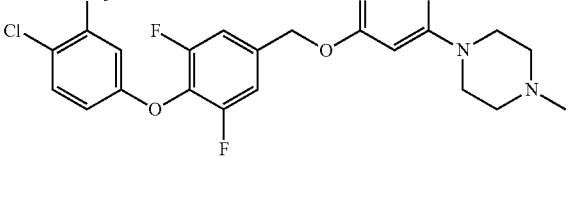
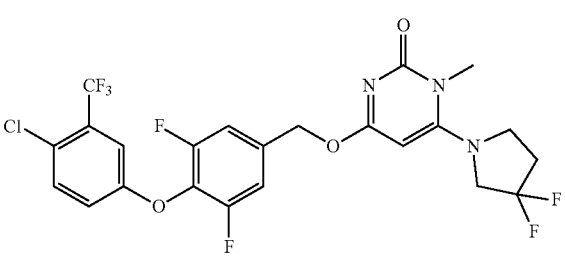

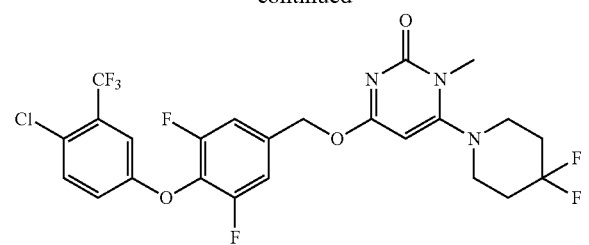
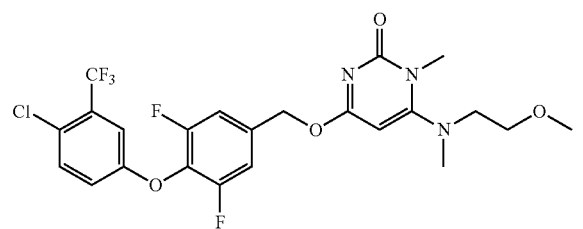 [SMILES: COCCN(C)c1cc(OCc2cc(F)c(Oc3ccc(Cl)c(C(F)(F)F)c3)c(F)c2)nc(=O)n1C]
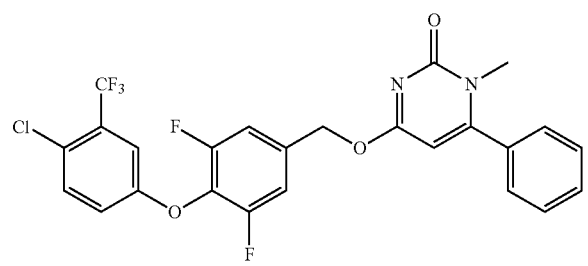 [SMILES: Cn1c(-c2ccccc2)cc(OCc2cc(F)c(Oc3ccc(Cl)c(C(F)(F)F)c3)c(F)c2)nc1=O]
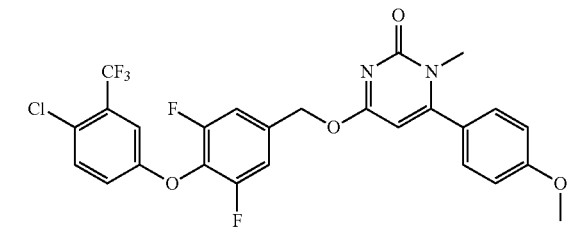 [SMILES: COc1ccc(-c2cc(OCc3cc(F)c(Oc4ccc(Cl)c(C(F)(F)F)c4)c(F)c3)nc(=O)n2C)cc1]
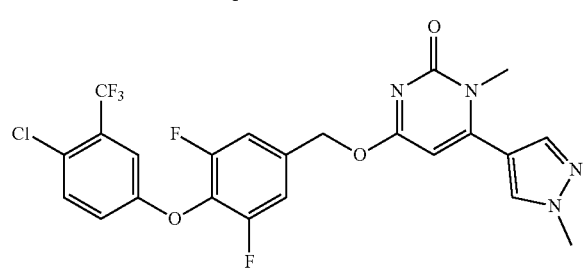
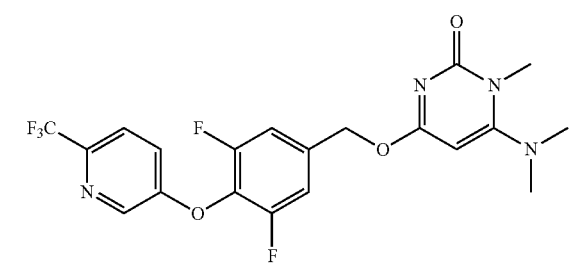 [SMILES: CN(C)c1cc(OCc2cc(F)c(Oc3ccc(C(F)(F)F)nc3)c(F)c2)nc(=O)n1C]
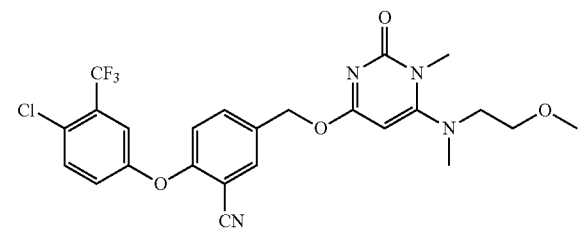 [SMILES: COCCN(C)c1cc(OCc2ccc(Oc3ccc(Cl)c(C(F)(F)F)c3)c(C#N)c2)nc(=O)n1C]
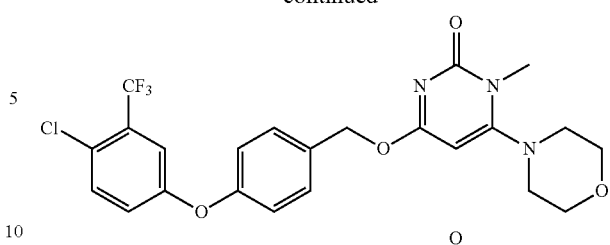
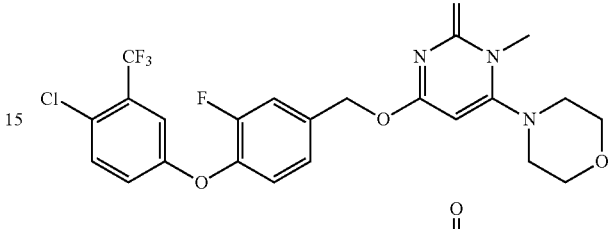
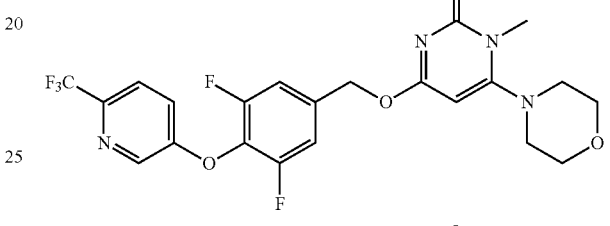
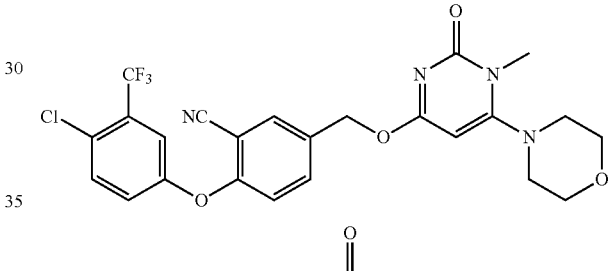
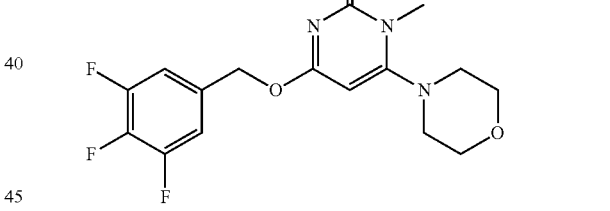
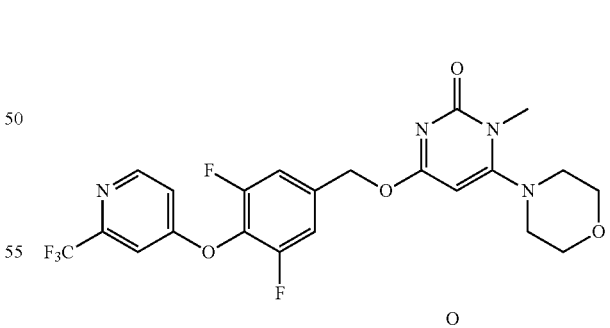
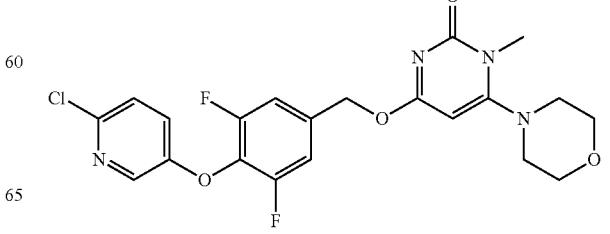

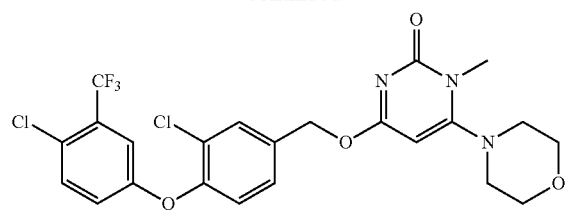 [SMILES: Cn1c(N2CCOCC2)cc(OCc2ccc(Oc3ccc(Cl)c(C(F)(F)F)c3)c(Cl)c2)nc1=O]
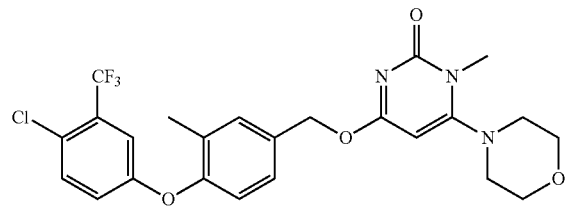 [SMILES: Cc1cc(COc2cc(N3CCOCC3)n(C)c(=O)n2)ccc1Oc1ccc(Cl)c(C(F)(F)F)c1]
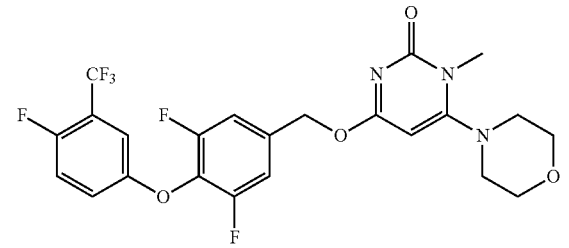 [SMILES: Cn1c(N2CCOCC2)cc(OCc2cc(F)c(Oc3ccc(F)c(C(F)(F)F)c3)c(F)c2)nc1=O]
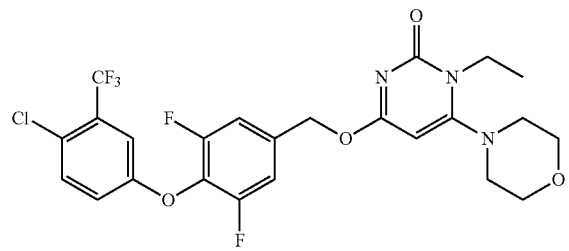 [SMILES: CCn1c(N2CCOCC2)cc(OCc2cc(F)c(Oc3ccc(Cl)c(C(F)(F)F)c3)c(F)c2)nc1=O]
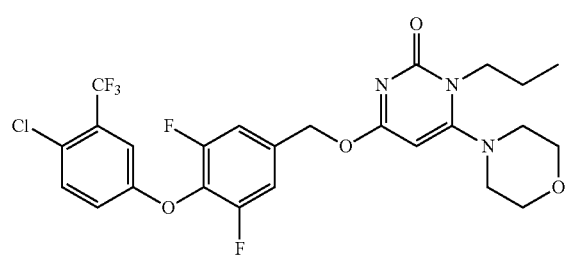 [SMILES: CCCn1c(N2CCOCC2)cc(OCc2cc(F)c(Oc3ccc(Cl)c(C(F)(F)F)c3)c(F)c2)nc1=O]
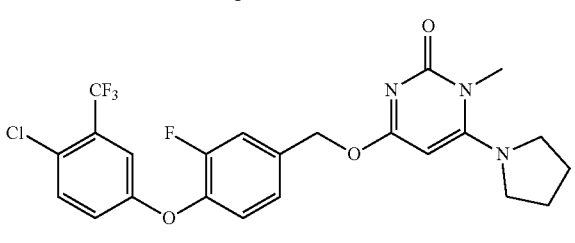
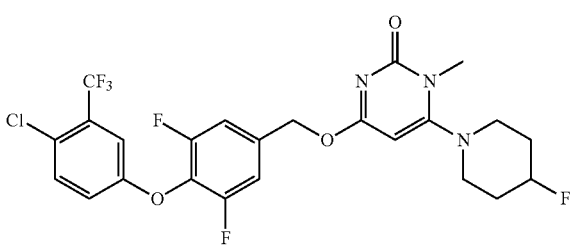 [SMILES: Cn1c(N2CCC(F)CC2)cc(OCc2cc(F)c(Oc3ccc(Cl)c(C(F)(F)F)c3)c(F)c2)nc1=O]
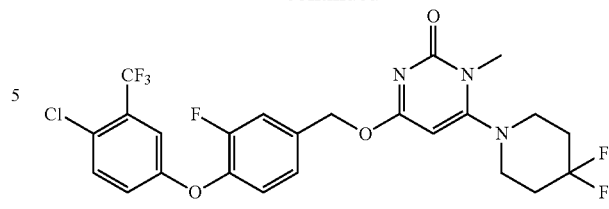
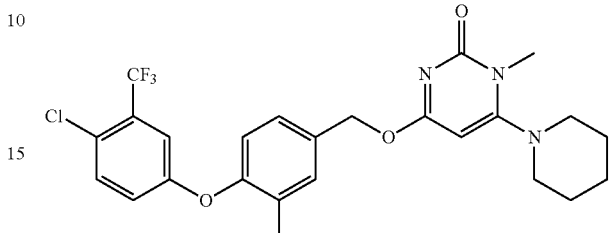
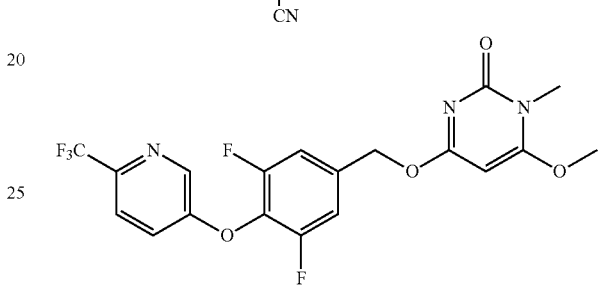
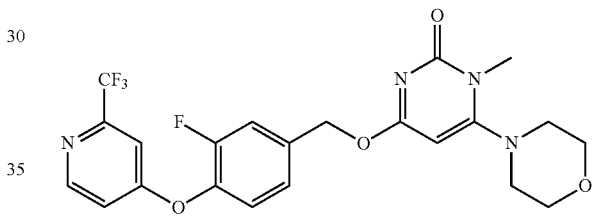
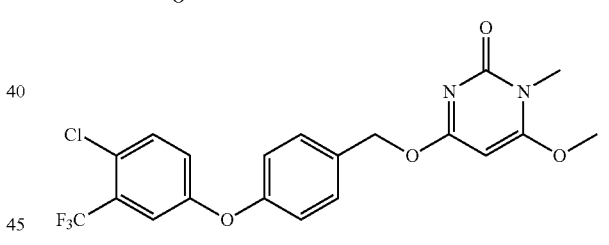
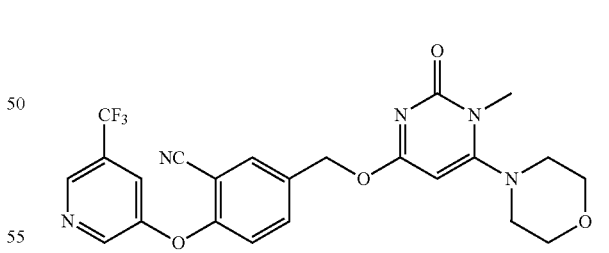
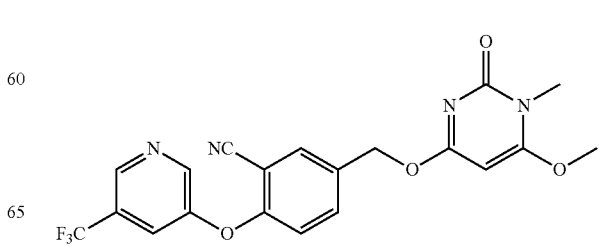

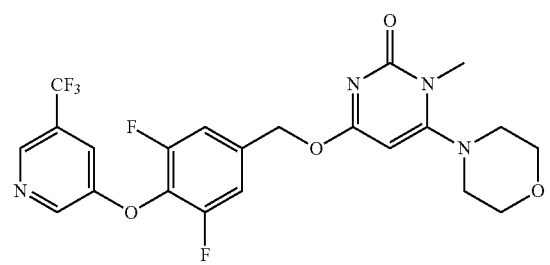 [SMILES: Cn1c(N2CCOCC2)cc(OCc2cc(F)c(Oc3cncc(C(F)(F)F)c3)c(F)c2)nc1=O]
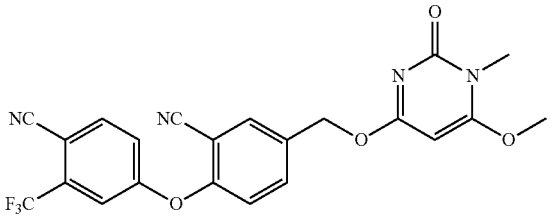
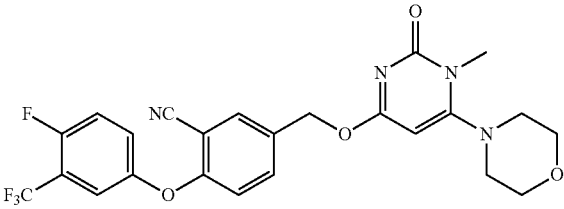 [SMILES: Cn1c(N2CCOCC2)cc(OCc2ccc(Oc3ccc(F)c(C(F)(F)F)c3)c(C#N)c2)nc1=O]
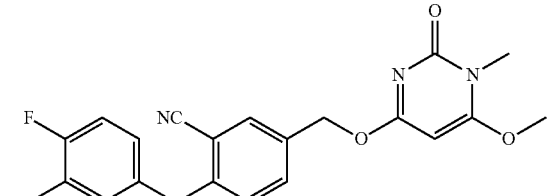
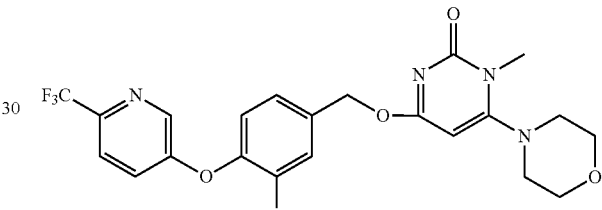
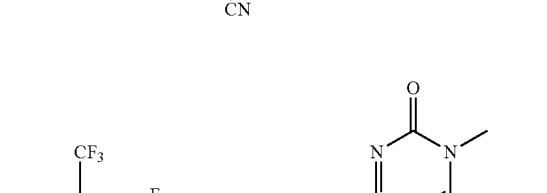
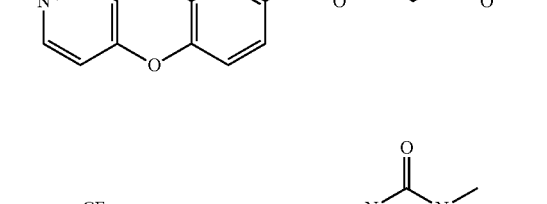
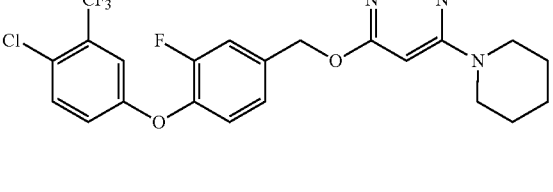
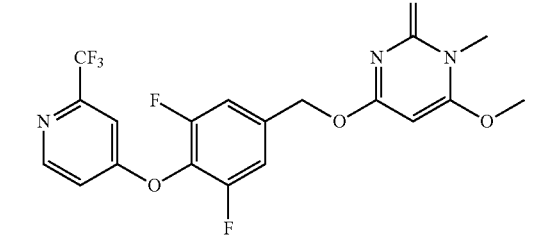

97
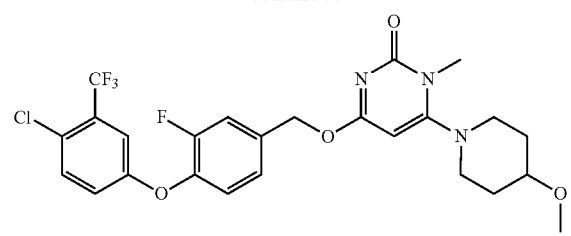 [SMILES: COC1CCN(c2cc(OCc3ccc(Oc4ccc(Cl)c(C(F)(F)F)c4)c(F)c3)nc(=O)n2C)CC1]
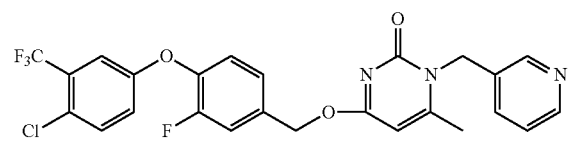
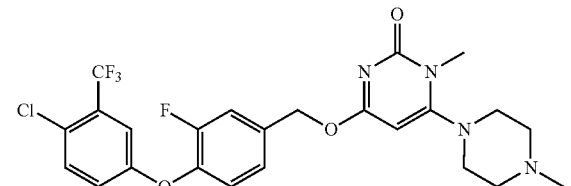
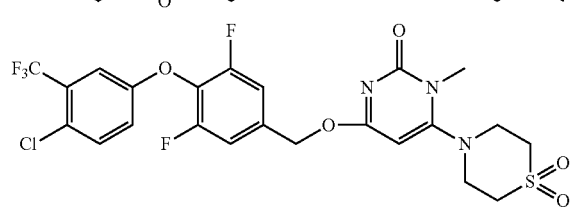
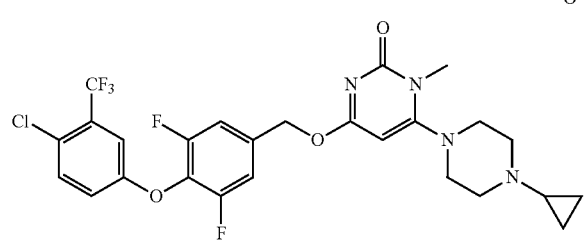
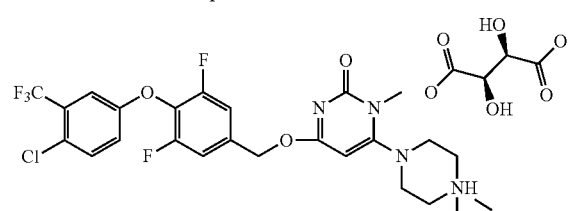
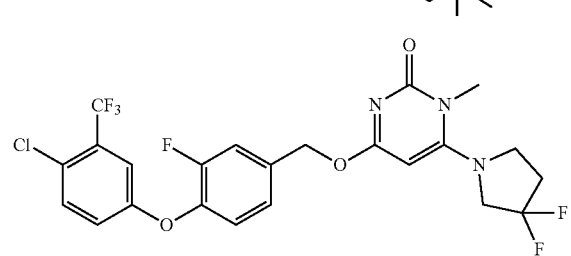
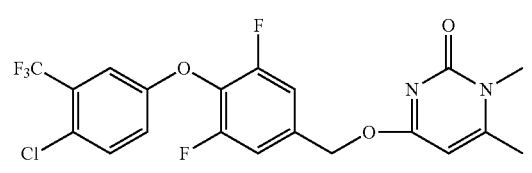
98
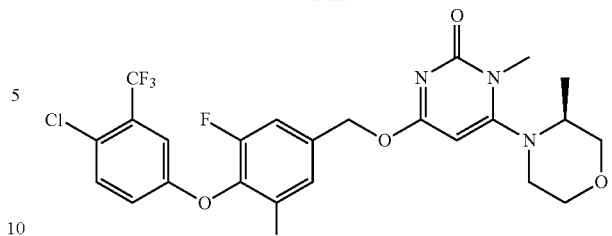
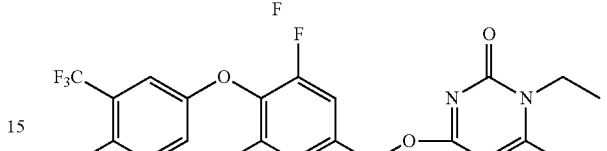
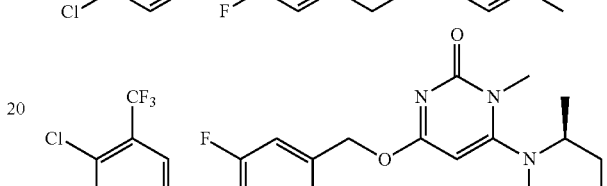
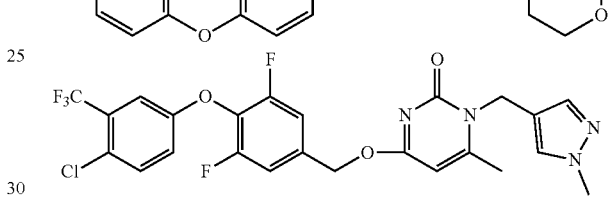
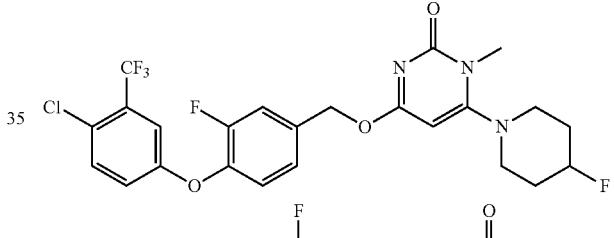
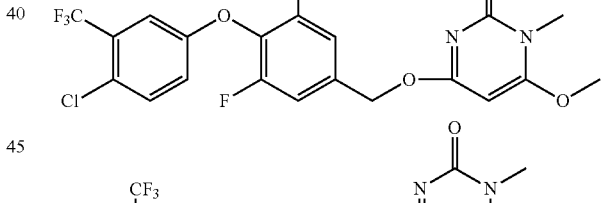
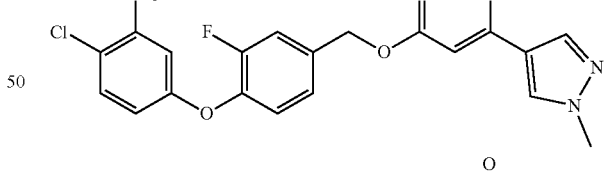
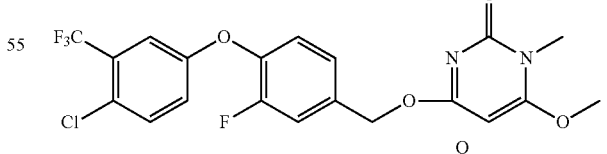
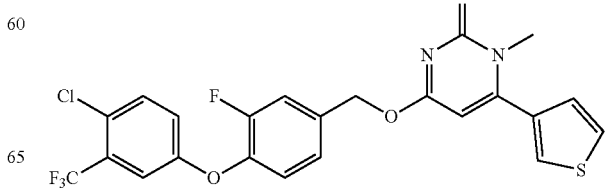

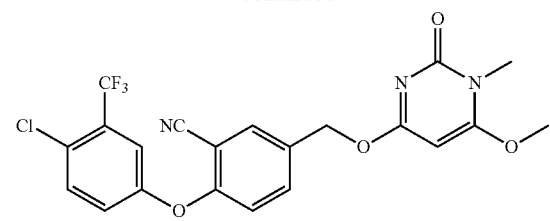
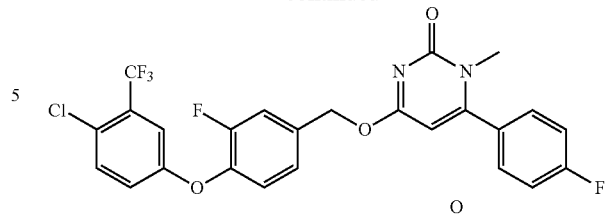
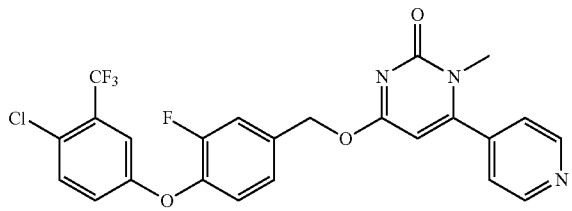 [SMILES: Cn1c(-c2ccncc2)cc(OCc2ccc(Oc3ccc(Cl)c(C(F)(F)F)c3)c(F)c2)nc1=O]
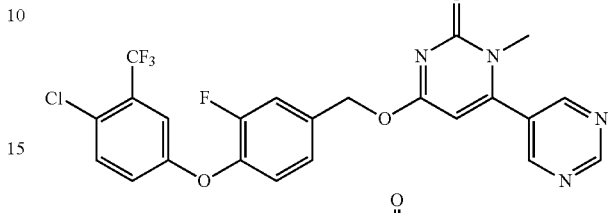
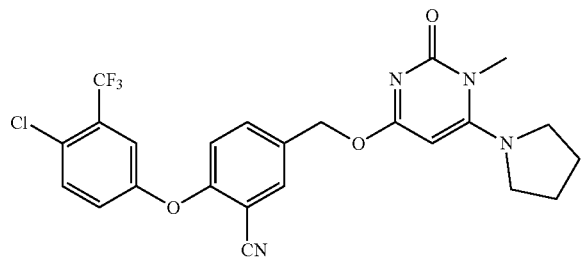
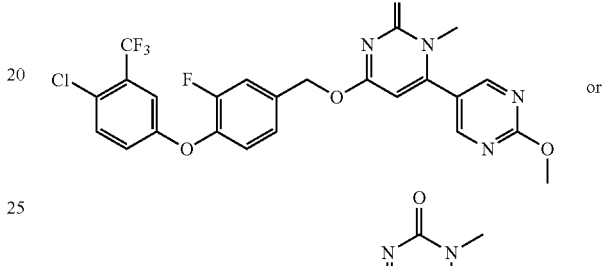
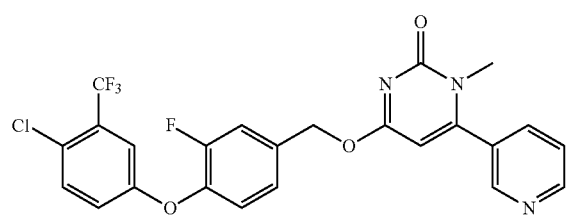 [SMILES: Cn1c(-c2cccnc2)cc(OCc2ccc(Oc3ccc(Cl)c(C(F)(F)F)c3)c(F)c2)nc1=O]
6. The method according to claim 1, wherein the said diabetic complication is diabetic eye disease.
7. The method according to claim 1, wherein the said diabetic complication is diabetic kidney disease.
8. The method according to claim 1, wherein the said diabetic eye disease is diabetic macular edema.
* * * * *